United States Patent
Gross et al.

(10) Patent No.: US 11,410,750 B2
(45) Date of Patent: Aug. 9, 2022

(54) METHYLATION MARKERS AND TARGETED METHYLATION PROBE PANEL

(71) Applicant: GRAIL, LLC, Menlo Park, CA (US)

(72) Inventors: Samuel S. Gross, Menlo Park, CA (US); Oliver Claude Venn, Menlo Park, CA (US); Seyedmehdi Shojaee, Menlo Park, CA (US); John Beausang, Menlo Park, CA (US); Arash Jamshidi, Menlo Park, CA (US)

(73) Assignee: GRAIL, LLC, Menlo Park, CA (US)

( * ) Notice: Subject to any disclaimer, the term of this patent is extended or adjusted under 35 U.S.C. 154(b) by 0 days.

(21) Appl. No.: 17/214,190

(22) Filed: Mar. 26, 2021

(65) Prior Publication Data

US 2021/0238694 A1    Aug. 5, 2021

Related U.S. Application Data

(63) Continuation of application No. PCT/US2019/053509, filed on Sep. 27, 2019, which
(Continued)

(51) Int. Cl.
| | |
|---|---|
| *G16B 40/00* | (2019.01) |
| *G16B 30/10* | (2019.01) |
| *G16B 5/00* | (2019.01) |
| *G16B 20/20* | (2019.01) |
| *G16B 40/20* | (2019.01) |
| G16B 25/20 | (2019.01) |
| G16B 20/00 | (2019.01) |
| C12Q 1/6886 | (2018.01) |

(52) U.S. Cl.
CPC ............... *G16B 40/00* (2019.02); *G16B 5/00* (2019.02); *G16B 20/20* (2019.02); *G16B 30/10* (2019.02); *G16B 40/20* (2019.02); *C12Q 1/6886* (2013.01); *C12Q 2600/154* (2013.01); *G16B 20/00* (2019.02); *G16B 25/20* (2019.02)

(58) Field of Classification Search
None
See application file for complete search history.

(56) References Cited

U.S. PATENT DOCUMENTS

| | | |
|---|---|---|
| 6,773,897 B2 | 8/2004 | Herman et al. |
| 6,773,987 B1 | 8/2004 | Rahim et al. |
| | (Continued) | |

FOREIGN PATENT DOCUMENTS

| | | |
|---|---|---|
| EP | 1309728 A2 | 5/2003 |
| EP | 1342794 B1 | 12/2005 |
| | (Continued) | |

OTHER PUBLICATIONS

Masser, D.R. et al. Bisulfite oligonucleotide-capture sequencing for targeted base and strand-specific absolute 5-methylcytosine quantitation, AGE (2016) 38: 49 (Year: 2016).*
(Continued)

*Primary Examiner* — Xiaoyun R Xu
(74) *Attorney, Agent, or Firm* — Greenberg Traurig, LLP

(57) ABSTRACT

The present description provides a cancer assay panel for targeted detection of cancer-specific methylation patterns. Further provided herein are methods of designing, making, and using the cancer assay panel for the diagnosis of cancer.

28 Claims, 29 Drawing Sheets

Specification includes a Sequence Listing.

Related U.S. Application Data is a continuation-in-part of application No. PCT/US2019/025358, filed on Apr. 2, 2019.

(60) Provisional application No. 62/737,836, filed on Sep. 27, 2018.

(56) References Cited

U.S. PATENT DOCUMENTS

| | | |
|---|---|---|
| 7,041,455 B2 | 5/2006 | Magness et al. |
| 7,371,526 B2 | 5/2008 | Zon et al. |
| 7,413,855 B2 | 8/2008 | Bergmann et al. |
| 7,655,399 B2 | 2/2010 | Cantor et al. |
| 7,700,282 B2 | 4/2010 | Tetzner et al. |
| 7,700,324 B1 | 4/2010 | Issa et al. |
| 7,749,702 B2 | 7/2010 | Lofton-Day et al. |
| 7,785,798 B2 | 8/2010 | Cantor et al. |
| 7,899,626 B2 | 3/2011 | Kruglyak et al. |
| 8,076,063 B2 | 12/2011 | Fan |
| 8,133,986 B2 | 3/2012 | Issa et al. |
| 8,137,937 B2 | 3/2012 | Markert-Hahn |
| 8,143,001 B2 | 3/2012 | Kurn et al. |
| 8,150,626 B2 | 4/2012 | Fan et al. |
| 8,318,433 B2 | 11/2012 | Brenner |
| 8,318,460 B2 | 11/2012 | Cantor et al. |
| 8,415,100 B2 | 4/2013 | Markowitz et al. |
| 8,455,190 B2 | 6/2013 | Makrigiorgos |
| 8,481,292 B2 | 7/2013 | Casbon et al. |
| 8,486,634 B2 | 7/2013 | Lim et al. |
| 8,541,207 B2 | 9/2013 | Kester |
| 8,586,310 B2 | 11/2013 | Mitra et al. |
| 8,673,555 B2 | 3/2014 | Taylor et al. |
| 8,728,764 B2 | 5/2014 | Boutell |
| 8,741,567 B2 | 6/2014 | He et al. |
| 8,771,939 B2 | 7/2014 | Tetzner et al. |
| 8,822,155 B2 | 9/2014 | Sukumar et al. |
| 8,865,410 B2 | 10/2014 | Shendure et al. |
| 8,880,350 B2 | 11/2014 | Von Hoff et al. |
| 8,900,829 B2 | 12/2014 | Distler et al. |
| 8,927,209 B2 | 1/2015 | Hamamoto et al. |
| 9,040,239 B2 | 5/2015 | Zheng et al. |
| 9,115,386 B2 | 8/2015 | Rao et al. |
| 9,121,061 B2 | 9/2015 | Vaisvila et al. |
| 9,121,069 B2 | 9/2015 | Lo et al. |
| 9,128,086 B2 | 9/2015 | Bawden et al. |
| 9,183,349 B2 | 11/2015 | Kupershmidt et al. |
| 9,200,260 B2 | 12/2015 | Correa, Jr. et al. |
| 9,222,937 B2 | 12/2015 | Micallef |
| 9,260,745 B2 | 2/2016 | Rava et al. |
| 9,267,117 B2 | 2/2016 | Guan et al. |
| 9,290,803 B2 | 3/2016 | Laird et al. |
| 9,290,807 B2 | 3/2016 | Booth et al. |
| 9,292,660 B2 | 3/2016 | Von Hoff et al. |
| 9,315,853 B2 | 4/2016 | Domanico et al. |
| 9,371,566 B2 | 6/2016 | Lo et al. |
| 9,394,332 B2 | 7/2016 | Markert-Hahn et al. |
| 9,400,276 B2 | 7/2016 | Micallef |
| 9,447,452 B2 | 9/2016 | Rao et al. |
| 9,464,277 B2 | 10/2016 | Zheng et al. |
| 9,476,095 B2 | 10/2016 | Vogelstein et al. |
| 9,580,754 B2 | 2/2017 | Markowitz et al. |
| 9,598,731 B2 | 3/2017 | Talasaz |
| 9,670,530 B2 | 6/2017 | Kostem et al. |
| 9,702,002 B2 | 7/2017 | Boutell |
| 9,702,004 B2 | 7/2017 | Van Eijk et al. |
| 9,732,390 B2 | 8/2017 | Lo et al. |
| 9,745,614 B2 | 8/2017 | Schroeder |
| 9,745,627 B2 | 8/2017 | Van Eijk et al. |
| 9,752,188 B2 | 9/2017 | Schmitt et al. |
| 9,816,986 B2 | 11/2017 | Rao et al. |
| 9,834,822 B2 | 12/2017 | Talasaz |
| 9,840,743 B2 | 12/2017 | Talasaz |
| 9,850,523 B1 | 12/2017 | Chudova et al. |
| 9,862,995 B2 | 1/2018 | Patel |
| 9,868,756 B2 | 1/2018 | Markert-Hahn et al. |
| 9,896,725 B2 | 2/2018 | Lee et al. |
| 9,896,726 B2 | 2/2018 | Vaisvila et al. |
| 9,902,992 B2 | 2/2018 | Talasaz et al. |
| 9,920,363 B2 | 3/2018 | Gao et al. |
| 9,920,366 B2 | 3/2018 | Eltoukhy et al. |
| 9,938,575 B2 | 4/2018 | Tischfield et al. |
| 9,984,201 B2 | 5/2018 | Zhang et al. |
| 10,011,878 B2 | 7/2018 | Ahlquist et al. |
| 10,031,131 B2 | 7/2018 | Rao et al. |
| 10,093,986 B2 | 10/2018 | Zhang et al. |
| 10,144,953 B2 | 12/2018 | Domanico et al. |
| 10,297,342 B2 | 5/2019 | Lo et al. |
| 10,392,666 B2 | 8/2019 | Lo et al. |
| 10,435,754 B2 | 10/2019 | Lo et al. |
| 10,435,755 B2 | 10/2019 | Ahlquist et al. |
| 10,704,083 B2 | 7/2020 | Domanico et al. |
| 10,718,026 B2 | 7/2020 | Weinhausel et al. |
| 2002/0192698 A1 | 12/2002 | Pinkel et al. |
| 2003/0104464 A1 | 6/2003 | Berlin et al. |
| 2005/0196792 A1 | 9/2005 | Fodor et al. |
| 2005/0221314 A1 | 10/2005 | Berlin et al. |
| 2006/0286576 A1 | 12/2006 | Lofton-Day et al. |
| 2006/0292585 A1 | 12/2006 | Nautiyal et al. |
| 2007/0141582 A1 | 6/2007 | Li et al. |
| 2007/0161031 A1 | 7/2007 | Trinklein et al. |
| 2008/0081338 A1 | 4/2008 | Lo et al. |
| 2008/0286787 A1 | 11/2008 | Campan et al. |
| 2008/0305481 A1 | 12/2008 | Whitman et al. |
| 2009/0280479 A1 | 11/2009 | Hoon et al. |
| 2010/0068720 A1 | 3/2010 | Li et al. |
| 2010/0120022 A1 | 5/2010 | Ayalon-Soffer et al. |
| 2010/0304978 A1 | 12/2010 | Deng et al. |
| 2011/0027771 A1 | 2/2011 | Deng |
| 2011/0165565 A1 | 7/2011 | Wang et al. |
| 2011/0237444 A1 | 9/2011 | Clancy et al. |
| 2012/0053062 A1 | 3/2012 | Brooks |
| 2012/0149593 A1 | 6/2012 | Hicks et al. |
| 2012/0157324 A1 | 6/2012 | Lizardi et al. |
| 2012/0190023 A1 | 7/2012 | Wasserstrom |
| 2012/0208711 A1 | 8/2012 | Cortese |
| 2012/0221249 A1 | 8/2012 | Lizardi et al. |
| 2013/0017958 A1 | 1/2013 | Benz et al. |
| 2013/0059734 A1 | 3/2013 | Molloy et al. |
| 2013/0129668 A1 | 5/2013 | Firestein et al. |
| 2013/0130924 A1 | 5/2013 | Walrafen et al. |
| 2013/0186639 A1 | 7/2013 | Zhao et al. |
| 2013/0203605 A1 | 8/2013 | Shendure et al. |
| 2013/0261984 A1 | 10/2013 | Eberle et al. |
| 2014/0024537 A1 | 1/2014 | Rigatti et al. |
| 2014/0080715 A1 | 3/2014 | Lo et al. |
| 2014/0256574 A1 | 9/2014 | Herold et al. |
| 2014/0274740 A1 | 9/2014 | Srinivasan et al. |
| 2014/0274748 A1 | 9/2014 | Ahlquist et al. |
| 2014/0274752 A1 | 9/2014 | Blume et al. |
| 2014/0274767 A1 | 9/2014 | Yegnasubramanian et al. |
| 2014/0342940 A1 | 11/2014 | Oliphant et al. |
| 2014/0357497 A1 | 12/2014 | Zhang et al. |
| 2014/0364323 A1 | 12/2014 | Fan et al. |
| 2015/0038352 A1 | 2/2015 | Cao et al. |
| 2015/0099670 A1 | 4/2015 | Li et al. |
| 2015/0104793 A1 | 4/2015 | Quake et al. |
| 2015/0159212 A1 | 6/2015 | Pantoja et al. |
| 2015/0197798 A1 | 7/2015 | Xu et al. |
| 2015/0197809 A1 | 7/2015 | Myers et al. |
| 2015/0209786 A1 | 7/2015 | Hage et al. |
| 2015/0259743 A1 | 9/2015 | Burgess et al. |
| 2015/0299781 A1 | 10/2015 | Ost |
| 2015/0322513 A1 | 11/2015 | Gromminger et al. |
| 2015/0368708 A1 | 12/2015 | Talasaz |
| 2016/0003848 A1 | 1/2016 | Holdenrieder |
| 2016/0017396 A1 | 1/2016 | Cann et al. |
| 2016/0017419 A1 | 1/2016 | Chiu et al. |
| 2016/0040229 A1 | 2/2016 | Talasaz et al. |
| 2016/0047001 A1 | 2/2016 | Larisch |
| 2016/0138079 A1 | 5/2016 | Guan et al. |
| 2016/0144378 A1 | 5/2016 | Huang et al. |
| 2016/0168648 A1 | 6/2016 | Allawi et al. |
| 2016/0186267 A1 | 6/2016 | So et al. |
| 2016/0210403 A1 | 7/2016 | Zhang et al. |
| 2016/0232290 A1 | 8/2016 | Rava et al. |

(56) References Cited

U.S. PATENT DOCUMENTS

| | | |
|---|---|---|
| 2016/0239604 A1 | 8/2016 | Chudova et al. |
| 2016/0251704 A1 | 9/2016 | Talasaz et al. |
| 2016/0258014 A1 | 9/2016 | Booth et al. |
| 2016/0265027 A1 | 9/2016 | Sanches-Kuiper et al. |
| 2016/0265042 A1 | 9/2016 | Schroeder et al. |
| 2016/0275240 A1 | 9/2016 | Huelga |
| 2016/0281175 A1 | 9/2016 | Weinhausel et al. |
| 2016/0298183 A1 | 10/2016 | Wen et al. |
| 2016/0319345 A1 | 11/2016 | Gnerre et al. |
| 2016/0333417 A1 | 11/2016 | Talasaz |
| 2016/0333420 A1 | 11/2016 | Stern et al. |
| 2016/0340740 A1 | 11/2016 | Zhang |
| 2016/0348152 A1 | 12/2016 | Zheng et al. |
| 2016/0362748 A1 | 12/2016 | Mongan et al. |
| 2017/0024513 A1 | 1/2017 | Lo et al. |
| 2017/0029900 A1 | 2/2017 | Lo et al. |
| 2017/0101685 A1 | 4/2017 | Lo et al. |
| 2017/0121767 A1 | 5/2017 | Dor et al. |
| 2017/0137871 A1 | 5/2017 | Lai et al. |
| 2017/0175205 A1 | 6/2017 | Toung et al. |
| 2017/0176420 A1 | 6/2017 | Rao et al. |
| 2017/0191119 A1 | 7/2017 | Rao et al. |
| 2017/0198344 A1 | 7/2017 | Vaisvila et al. |
| 2017/0211143 A1 | 7/2017 | Shendure et al. |
| 2017/0218338 A1 | 8/2017 | Rao et al. |
| 2017/0219589 A1 | 8/2017 | Rao et al. |
| 2017/0233829 A1 | 8/2017 | Lo et al. |
| 2017/0235877 A1 | 8/2017 | Lo et al. |
| 2017/0240973 A1 | 8/2017 | Eltoukhy et al. |
| 2017/0249421 A1 | 8/2017 | Eberle et al. |
| 2017/0260590 A1 | 9/2017 | Eltoukhy et al. |
| 2017/0275689 A1 | 9/2017 | Maguire |
| 2017/0292147 A1 | 10/2017 | Kostem et al. |
| 2017/0321276 A1 | 11/2017 | Cantor et al. |
| 2017/0327869 A1 | 11/2017 | Schutz et al. |
| 2017/0356053 A1 | 12/2017 | Otto et al. |
| 2017/0362638 A1 | 12/2017 | Chudova et al. |
| 2018/0010176 A1 | 1/2018 | Patel |
| 2018/0010192 A1 | 1/2018 | Zhang et al. |
| 2018/0023125 A1 | 1/2018 | Talasaz et al. |
| 2018/0044632 A1 | 2/2018 | Rao et al. |
| 2018/0044633 A1 | 2/2018 | Rao et al. |
| 2018/0044731 A1 | 2/2018 | Valouev et al. |
| 2018/0045727 A1 | 2/2018 | Spetzler et al. |
| 2018/0066306 A1 | 3/2018 | Namsaraev et al. |
| 2018/0082012 A1 | 3/2018 | Jiang et al. |
| 2018/0094325 A1 | 4/2018 | Zhang et al. |
| 2018/0105884 A1 | 4/2018 | Lo et al. |
| 2018/0119113 A1 | 5/2018 | Rao et al. |
| 2018/0119225 A1 | 5/2018 | Rao et al. |
| 2018/0119230 A1 | 5/2018 | Velculescu et al. |
| 2018/0120304 A1 | 5/2018 | Rao et al. |
| 2018/0171397 A1 | 6/2018 | Vaisvila et al. |
| 2018/0179587 A1 | 6/2018 | Rao et al. |
| 2018/0180602 A1 | 6/2018 | Rao et al. |
| 2018/0216195 A1 | 8/2018 | Elnitski et al. |
| 2018/0237867 A1 | 8/2018 | Bajic et al. |
| 2018/0327859 A1 | 11/2018 | Van Engeland et al. |
| 2019/0032149 A1 | 1/2019 | Van Engeland et al. |
| 2019/0136327 A1 | 5/2019 | Zhang et al. |
| 2019/0256921 A1* | 8/2019 | Mueller ............... G16B 99/00 |
| 2019/0287652 A1 | 9/2019 | Gross et al. |
| 2021/0017609 A1 | 1/2021 | Gross et al. |
| 2021/0025011 A1 | 1/2021 | Gross |

FOREIGN PATENT DOCUMENTS

| | | |
|---|---|---|
| EP | 1394173 B1 | 10/2007 |
| EP | 1644519 B1 | 12/2008 |
| EP | 1567669 B1 | 3/2010 |
| EP | 2771483 A1 | 9/2014 |
| EP | 2391729 B1 | 9/2016 |
| EP | 2825675 B1 | 12/2017 |
| EP | 3265562 A2 | 1/2018 |
| EP | 3087204 B1 | 2/2018 |
| EP | 3288455 A1 | 3/2018 |
| EP | 3094747 B1 | 11/2018 |
| EP | 2893040 B1 | 1/2019 |
| EP | 3497220 A1 | 6/2019 |
| EP | 3207134 B1 | 7/2019 |
| EP | 3218523 B1 | 2/2020 |
| EP | 3289097 B1 | 3/2020 |
| WO | WO-0181620 A2 | 11/2001 |
| WO | WO-2003054219 A2 | 7/2003 |
| WO | WO-2005017207 A2 | 2/2005 |
| WO | WO-2005019477 A2 | 3/2005 |
| WO | WO-2005118852 A2 | 12/2005 |
| WO | WO-2006128192 A2 | 11/2006 |
| WO | WO-2007106802 A2 | 9/2007 |
| WO | WO-2008038000 A1 | 4/2008 |
| WO | WO-2008048508 A2 | 4/2008 |
| WO | WO-2008073303 A2 | 6/2008 |
| WO | WO-2008084219 A1 | 7/2008 |
| WO | WO-2010037001 A2 | 4/2010 |
| WO | WO-2010085343 A1 | 7/2010 |
| WO | WO-2011038507 A1 | 4/2011 |
| WO | WO-2011127136 A1 | 10/2011 |
| WO | WO-2012031329 A1 | 3/2012 |
| WO | WO-2012138973 A2 | 10/2012 |
| WO | WO-2012149171 A1 | 11/2012 |
| WO | WO-2012178074 A1 | 12/2012 |
| WO | WO-2013060762 A1 | 5/2013 |
| WO | WO-2013163207 A1 | 10/2013 |
| WO | WO-2013186639 A2 | 12/2013 |
| WO | WO-2014026768 A1 | 2/2014 |
| WO | WO-2014043763 A1 | 3/2014 |
| WO | WO-2014135469 A2 | 9/2014 |
| WO | WO-2014151117 A1 | 9/2014 |
| WO | WO-2014184684 A2 | 11/2014 |
| WO | WO-2014205981 A1 | 12/2014 |
| WO | WO-2015101515 A2 | 7/2015 |
| WO | WO-2015116837 A1 | 8/2015 |
| WO | WO-2015124955 A1 | 8/2015 |
| WO | WO-2015145133 A1 | 10/2015 |
| WO | WO-2015153284 A1 | 10/2015 |
| WO | WO-2015179672 A1 | 11/2015 |
| WO | WO-2016008451 A1 | 1/2016 |
| WO | WO-2016015058 A2 | 1/2016 |
| WO | WO-2016016639 A1 | 2/2016 |
| WO | WO-2016034908 A1 | 3/2016 |
| WO | WO-2016063034 A1 | 4/2016 |
| WO | WO-2016063059 A1 | 4/2016 |
| WO | WO-2016094813 A1 | 6/2016 |
| WO | WO-2016097251 A1 | 6/2016 |
| WO | WO-2016101258 A1 | 6/2016 |
| WO | WO-2016115530 A1 | 7/2016 |
| WO | WO-2016127844 A1 | 8/2016 |
| WO | WO-2016127944 A1 | 8/2016 |
| WO | WO-2016141324 A2 | 9/2016 |
| WO | WO-2016170319 A1 | 10/2016 |
| WO | WO-2016179049 A1 | 11/2016 |
| WO | WO-2016189288 A1 | 12/2016 |
| WO | WO-2016210224 A1 | 12/2016 |
| WO | WO-2017008912 A1 | 1/2017 |
| WO | WO-2017012544 A1 | 1/2017 |
| WO | WO-2017027835 A1 | 2/2017 |
| WO | WO-2017048932 A1 | 3/2017 |
| WO | WO-2017062970 A1 | 4/2017 |
| WO | WO-2017083562 A1 | 5/2017 |
| WO | WO-2017106481 A1 | 6/2017 |
| WO | 2017127741 A1 | 7/2017 |
| WO | WO-2017136603 A1 | 8/2017 |
| WO | WO-2017176630 A1 | 10/2017 |
| WO | WO-2017181079 A2 | 10/2017 |
| WO | WO-2017181111 A2 | 10/2017 |
| WO | WO-2017181134 A2 | 10/2017 |
| WO | WO-2017181146 A1 | 10/2017 |
| WO | WO-2017181202 A2 | 10/2017 |
| WO | WO-2017194668 A1 | 11/2017 |
| WO | WO-2017201102 A1 | 11/2017 |
| WO | WO-2017212428 A1 | 12/2017 |
| WO | WO-2018005983 A1 | 1/2018 |
| WO | WO-2018009696 A1 | 1/2018 |
| WO | WO-2018009702 A1 | 1/2018 |

(56) References Cited

FOREIGN PATENT DOCUMENTS

| WO | WO-2018009703 A1 | 1/2018 |
|---|---|---|
| WO | WO-2018009705 A1 | 1/2018 |
| WO | WO-2018009709 A1 | 1/2018 |
| WO | WO-2018022890 A1 | 2/2018 |
| WO | WO-2018022906 A1 | 2/2018 |
| WO | WO-2018031760 A1 | 2/2018 |
| WO | WO-2018039463 A1 | 3/2018 |
| WO | WO-2018119216 A1 | 6/2018 |
| WO | WO-2018119452 A2 | 6/2018 |
| WO | WO-2018136881 A1 | 7/2018 |
| WO | WO-2018161031 A1 | 9/2018 |
| WO | WO-2018195211 A1 | 10/2018 |
| WO | WO-2018195217 A1 | 10/2018 |
| WO | WO-2018204764 A1 | 11/2018 |
| WO | 2019074700 A1 | 4/2019 |
| WO | WO-2019064063 A1 | 4/2019 |
| WO | WO-2019178277 A1 | 9/2019 |
| WO | WO-2019195268 A2 | 10/2019 |
| WO | WO-2019199696 A1 | 10/2019 |
| WO | WO-2020069350 A1 | 4/2020 |
| WO | WO-2020154682 A2 | 7/2020 |
| WO | 2020163403 A1 | 8/2020 |
| WO | 2020163410 A1 | 8/2020 |

OTHER PUBLICATIONS

AACRmeeting abstract in Apr. 2017, Liu et al., "Identify tissue-of-origin incancer cfDNA by whole genome sequencing" Abstract 5689/13.

Ashford, Molika. UCSD Methylation Haplotype Method Tracks cfDNA Origin; Singlera to Commercialize. Genome Web. Published Mar. 8, 2017. Accessed Dec. 7, 2020. Available at: https://www.genomeweb.com/molecular-diagnostics/ucsd-methylation-haplotype-method-tracks-cfdna-origin-singlera-commercialize#.X9POpmiQGUk.

Avraham, A. et al. Tissue Specific DNA Methylation in Normal Human Breast Epithelium and in Breast Cancer. PLOS One, 9(3):e91805:1-8 (Mar. 20, 2014).

Burnham, et al. Single-stranded DNA library preparation uncovers the origin and diversity of ultrashort cell-free DNA in plasma. Sci Rep. Jun. 14, 2016;6:27859. doi: 10.1038/srep27859.

Chan, K.C. et al. Noninvasive detection of cancer-associated genome-wide hypomethylation and copy number aberrations by plasma DNA bisulfite sequencing. Proc. Natl. Acad. Sci. USA 110(47):18761-18768 (Nov. 19, 2013).

Cheuk et al., Detection of Methylated Circulating DNA as Noninvasive Biomarkers for Breast Cancer Diagnosis. J. Breast Cancer 2017; 20(1): 12-17.

Chhibber et al. Single-molecule polymerase chain reaction reduces bias: Application to DNA methylation analysis by bisulfite sequencing. Anal. Biochem. vol. 377, Issue 1, Jun. 1, 2008, pp. 46-54.

clinicaltrials.gov [retrieved on Jun. 1, 2021], Retrieved from the Internet:www.clinicaltrials.gov/ct2/show/study/NCT02889978#armgroup.

Cohen, et al., Detection and localization of surgically resectable cancers with a multi-analyte blood test. Science Feb. 23, 2018:vol. 359, Issue 6378, pp. 926-930. DOI: 10.1126/science.aar3247.

Co-pending U.S. Appl. No. 17/214,038, inventors Gross; Samuel S. et al., filed Mar. 26, 2021.

Co-pending U.S. Appl. No. 17/214,105, inventors Gross; Samuel et al., filed Mar. 26, 2021.

Co-pending U.S. Appl. No. 17/214,682, inventors Xiang; Jing et al., filed Mar. 26, 2021.

Diep et al. Library-free methylation sequencing with bisulfite padlock probes. Nature Methods 9(3):270-272 (2012).

EZ DNA Methylation-Lightning Kit, Instruction Manual. Zymo Research, ver. 1.0.5.

Frimer et al. HPV16 methylation isa consistent biomarker of cervical intraepithelial neoplasia (CIN) 3 using anovel next-generation bisulfite-sequencing technology. GynecologicOncology. Jul. 2013, 130(1):e51-e52. Doi: https://doi.org/10.1016/j.ygyno.2013.04.182.

GenBank submission AC067721, Mar. 7, 2003 [online]. [Retrieved on Jun. 17, 2020].A Retrieved from the internet at< url: https://www.ncbi.nim.nih.gov/nuccore/AC067721 < /url:>.

GenBank submission AC093151.2, Jun. 25, 2002 [online]. [Retrieved on Jun. 17, 2020]. Retrieved from the internet at< url: https://www.ncbi.nlm.nih.gov/nuccore/AC093151 </url:>.

Guo, S. et al. Identification of methylation haplotype blocks aids in deconvolution of heterogeneous tissue samples and tumor tissue-of-origin mapping from plasma DNA. Nat Genet 2017;49:635-42.

Handbook of Chemistry and Physics, 49th Edition, 1968, Weast (ed.), The Chemical Rubber Co., Cleveland, Ohio, p. 245.

Hao et al. DNA methylation markers for diagnosis and prognosis of common cancers. PNAS USA 114(28):7414-7419 (w/Supplemental Information) (2017).

Huang et al., The Epigenome: Molecular Hide and Seek. Feb. 21, 2003, Chapter3, pp. 39-64. Doi: https://doi.org/10.1002/3527601511.ch3.

Husseiny, M. et al. Tissue-Specific Methylation of Human Insulin Gene and PCR Assay for Monitoring Beta Cell Death. PLoS ONE, 9(4):e9459:1-9 (Apr. 10, 2014).

Husseiny, M.I. et al. Development of a Quantitative Methylation-Specific Polymerase Chain Reaction Method for Monitoring Beta Cell Death in Type 1 Diabetes. PLoS One. PLOS ONE 7(10): e47942 (Oct. 29, 2012).

Kang et al., "CancerLocator: non-invasive cancer diagnosis and tissue-of-origin prediction using methylation profiles of cell-free DNA," Genome Biology vol. 18, Article No. 53 (2017).

Laird. Early Detection: The power and the promise of DNA methylation markers. Nat Rev Cancer 3:253-266 (2003).

Lebastchi, J. et al. Immune Therapy and β-Cell Death in Type 1 Diabetes. Diabetes, Brief Report 62(5):1676-1680 (May 2013).

Lehmann-Werman, et al. Identification of tissue-specific cell death using methylation patterns of circulating DNA. Proc Natl Acad Sci USA 2016;113:E1826-34.

Li et al. CancerDetector: ultrasensitive and non-invasive cancer detection at the resolution of individual reads using cell-free DNA methylation sequencing data. Nucleic Acids Research, vol. 46, Issue 15, Sep. 6, 2018, p. e89, https://doi.org/10.1093/nar/gky423.

Liu et al. Methylation-sensitive enrichment of minor DNA alleles using a double-strand DNA-specific nuclease. Nucleic Acids Research, 2017 vol. 45(6): e39.

Liu et al. Targeted methylation sequencing of plasma cell-free DNA for cancer detection and classification. Annals of Oncology 29: 1445-1453, 2018.

Madi, T. et al. The determination of tissue-specific DNAmethylation patterns in forensic biofluids using bisulfite modification andpyrosequencing. Electrophoresis,33(12):1736-1745 (Jul. 2012).

Miura et al., Highly sensitive targeted methylome sequencing by post-bisulfite adaptor tagging. DNA Research, vol. 22, Issue 1, Feb. 2015, pp. 13-18,https://doi.org/10.1093/dnares/dsu034.

Mouliere et al. Selecting short DNA fragments in plasma improves detection of circulating tumour DNA. May 2017. bioRxiv 134437; doi: https://doi.org/10.1101/134437.

Oncomine™ cfDNA Assays Part I: Library Preparation User Guide (2016).

Oncomine™cfDNA Assays part II: Plan a Run, Template Preparation, and Sequencing User Guide (2016).

PCT/US19/25358 International Search Report & Written Opinion dated Dec. 30, 2019.

PCT/US2019/053509 International Search Report dated Jan. 29, 2020.

Poon, Leo, L.M., et al., "Differential DNA Methylation between Fetus and Mother as a Strategy for Detecting Fetal DNA in Maternal Plasma," Clinical Chemistry, 2002, vol. 48, No. 1, pp. 35-41.

Raine, A. et al. Splinted Ligation Adapter Tagging (SPLAT), a novel library preparation method for whole genome bisulphite sequencing. Nucleic Acids Research, 110:1-15 (Nov. 28, 2016) .

Ross, JP et al. Identification of differentially methylated regions usign streptavidin bisulfite ligand methylation enrichment (SuBLiME),

(56) References Cited

OTHER PUBLICATIONS a new method to enrich for methylated DNA prior to deep bisulfite genomic sequencing. Epigenetics, 8(1):113-127 (Jan. 2013) E-pub: Dec. 20, 2012.
Shen et al., FACETS: allele-specific copy number and clonal heterogeneity analysis tool for high-throughput DNA sequencing. Nucleic Acids Research, 2016: 44(16) e131.
Shoemaker, et al., Allele-specific methylation is prevalent and is contributed by CpG-SNPs in the human genome. Genome Res. 2010.20:883-889.
Tanic, et al., Epigenome-wide association studies for cancer biomarker discovery in circulating cell-free DNA: technical advances and challenges. Current Opinion in Genetics & Development 2017, 42:48-55.
Toyota et al. Identification of differentially methylated sequences in colorectal cancer by methylated CpG island amplification. Cancer Research. May 1999. 59(10).
U.S. Appl. No. 17/061,013 Office Action dated Feb. 23, 2021.
U.S. Appl. No. 17/061,048 Office Action dated Feb. 1, 2021.
U.S. Appl. No. 17/061,048 Office Action dated Jun. 3, 2021.
Varley, K.E. et al. Bisulfite Patch PCR enables multiplexed sequencing of promoter methylation across cancer samples. Genome Research 20:1279-1287 (2010).
Vrba et al., "A suite of DNA methylation markers that can detect most common human cancers", EPIGENETICS, 2018, pp. 1-13.
Warton et al., Methylation of cell-free circulating DNA in the diagnosis of cancer. Frontiers in Mol. Bio. 2015; vol. 2, Art. 13.
Widschwendter, et al. Methylation patterns in serum DNA for early identification of disseminated breast cancer. Genome Medicine vol. 9, Article No. 115 (2017).
Yong, Ed. Written in Blood: DNA circulating in the bloodstream could guide cancer treatment—if researchers can work out how best to use it. Nature 2014: 511; 524-526.
Bejar, R., et al., Clinical Effect of Point Mutations in Myelodysplastic Syndromes, The New England Journal of Medicine, Jun. 2011, pp. 2496-2506.
Brandon, et al., "Mitochondrial mutations in cancer", Oncogene 25(34), 2006, pp. 4647-4662.
Genome Reference Consortium with a reference number, GRCh37/hg19, and also available from Genome Browser orovided by Santa Cruz Genomics Institute, Nucleic Acids Research, 2021, vol. 49, Nov. 22, 2020.
Harris, et al., "Single-Molecule DNA Sequencing of a Viral Genome", Science, vol. 320, 2008, 106-109.
Hashimoto, et al., "5'-end SAGE for the analysis of transcriptional start sites", Nature Biotechnology, 22, 2004, 1146-1149.
Illumina Data Sheet; Epigenetics "Infinfium HumanMethylation450 BeadChip", 4 pgs., 2012.
International Classification of Diseases for Oncology (ICD-O-3) (codes.iarc.fr) or the Surveillance, Epidemiology, and End Results Program (SEER) (sser.cancer.gov).
Kivioja, et al., "Counting absolute numbers of molecules using unique molecular identifiers", Nat Methods, 9(1), 2011, 72-4.
Li, et al., "Post-conversion targeted capture of modified cytosines in mammalian and plant genomes" NAR 43(12), e81, 16 pgs., 2015.
Mardis, E. R., et al., Recurring Mutations Found by Sequencing an Acute Myeloid Leukemia Genome, The New England Journal of Medicine, 2009, pp. 1058-1066.
Okamura, et al., "Lists of HumanMethylation450 BeadChip probes with nucleotide-variant information obtained from the Phase 3 data of the 1000 Genomes Project" Genomics Data, 7, pp. 67-69, 2016.
Papaemmanuil, E., et al., Somatic SF3B1 Mutation in Myelodysplasia with Ring Sideroblasts, The New England Journal of Medicine, Sep. 26, 2011, pp. 1384-1395.
Reidmiller M, Braun H. RPROP—A Fast Adaptive Learning Algorithm. Proceedings of the International Symposium on Computer and Information Science VII, 1992).
Surveillance, Epidemiology, and End Results Program (SEER) (seer.cancer.gov).
The STRIVE Study: Development of a Blood Test for Early Detection of Multiple Cancer Type, CinicalTrials.gov Identifier: NCT03085888, 6 pgs., 2017.
Walter, M., Clonal Architecture of Secondary Acute Myeloid Leukemia, The New England Journal of Medicine, , Mar. 14, 2012, pp. 1090-1098.
Zhai, et al.,"Genome-wide DNA Methylation Profiling of Cell-Free Serum DNA in Esophageal Adenocarcinoma and Barrett Esophagus" Neoplasia, 14(1), pp. 29-33, published Jan. 2012.

* cited by examiner

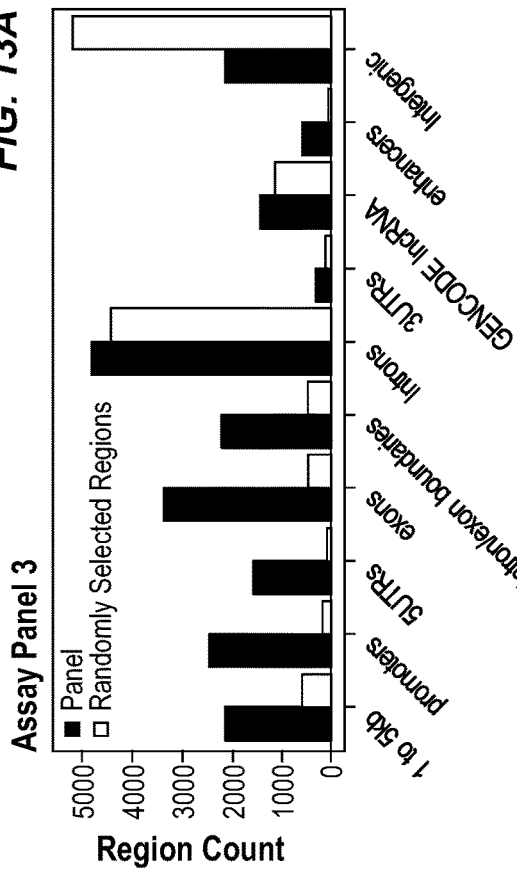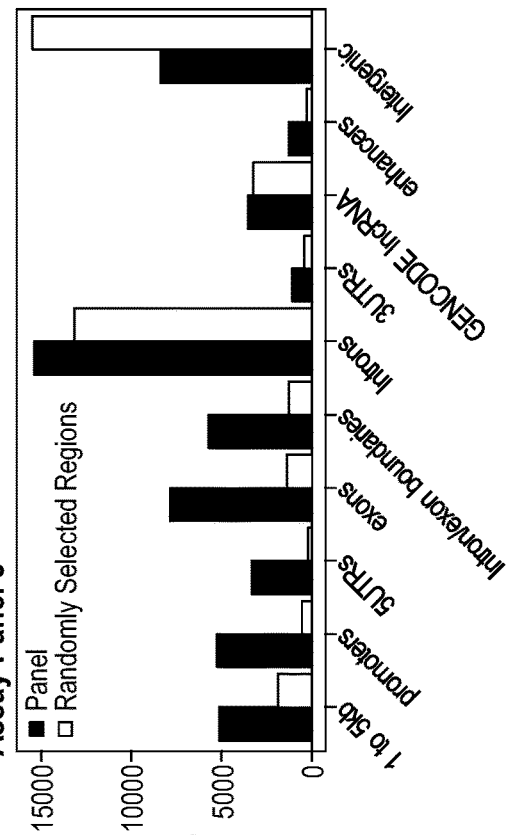

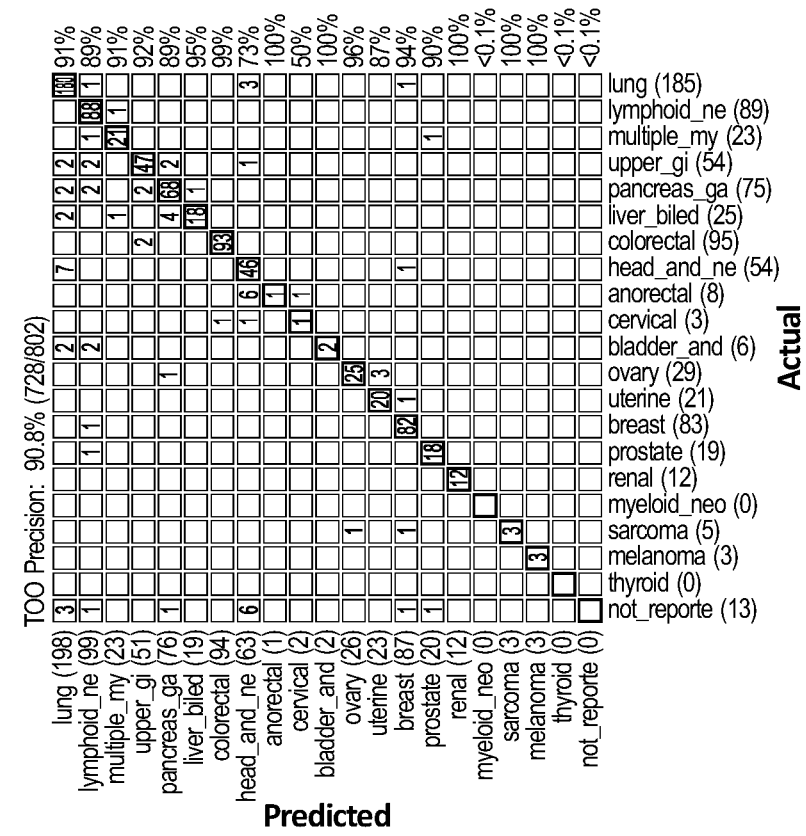
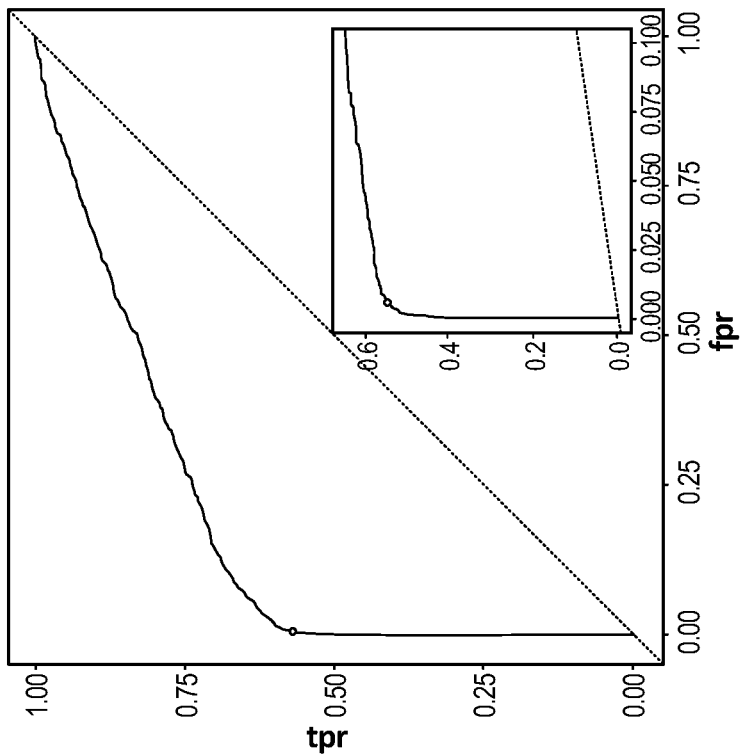
FIG. 19B
FIG. 19A

US 11,410,750 B2

METHYLATION MARKERS AND TARGETED METHYLATION PROBE PANEL

1. CROSS-REFERENCE

This is a continuation application of International Appl. No. PCT/US2019/053509, filed on Sep. 27, 2019, which claims the benefit of U.S. Provisional Application No. 62/737,836, filed Sep. 27, 2018, and also claims priority to continuation-in-part of International Appl. No. PCT/US2019/025358, filed on Apr. 2, 2019, both of which are hereby incorporated by reference in their entireties.

2. SEQUENCE LISTING

The instant application contains a Sequence Listing which has been submitted electronically in ASCII format and is hereby incorporated by reference in its entirety. Said ASCII copy, created on Sep. 26, 2019, is named 50251-846_01_SL.txt and is 52,371,626 bytes in size.

3. BACKGROUND

DNA methylation plays an important role in regulating gene expression. Aberrant DNA methylation has been implicated in many disease processes, including cancer. DNA methylation profiling using methylation sequencing (e.g., whole genome bisulfite sequencing (WGBS)) is increasingly recognized as a valuable diagnostic tool for detection, diagnosis, and/or monitoring of cancer. For example, specific patterns of differentially methylated regions may be useful as molecular markers for various diseases.

However, WGBS is not currently suitable for a product assay. The reason is that the vast majority of the genome is either not differentially methylated in cancer, or the local CpG density is too low to provide a robust signal. Only a few percent of the genome is likely to be useful in classification. With WGBS, deep sequencing (up to ~1000×) can be done in only a small set of genomic regions, perhaps 0.1% of the genome at current sequencing costs, because of cost constraints.

Furthermore, there have been various challenges in identifying differentially methylated regions in various diseases. First off, determining differentially methylated regions in a disease group only holds weight in comparison with a group of control subjects, such that if the control group is small in number, the determination loses confidence with the small control group. Additionally, among a group of control subjects, methylation status can vary which can be difficult to account for when determining the regions that are differentially methylated in a disease group. On another note, methylation of a cytosine at a CpG site is strongly correlated with methylation at a subsequent CpG site. To encapsulate this dependency is a challenge in itself.

Accordingly, a cost-effective method of accurately diagnosing a disease by analyzing DNA from differentially methylated regions has not yet been available.

4. SUMMARY

Early detection of cancer in subjects is important as it allows for earlier treatment and therefore a greater chance for survival. Targeted detection of cancer-specific methylation patterns using cell-free DNA (cfDNA) fragments can make early detection of cancer possible by providing cost-effective and non-invasive method for getting information relevant to detecting the presence or absence of cancer, a cancer tissue of origin, or cancer type. By using a targeted genomic region panel rather than sequencing all nucleic acids in a test sample, also known as "whole genome sequencing," the method can increase sequencing depth of the target regions.

Towards that end, the present description provides cancer assay panels (alternatively referred to as "bait sets") for detection of cancer-specific methylation patterns in targeted genomic regions, along with methods of using the cancer assay panels for diagnosis of cancer. Further provided herein are methods of designing and making the cancer assay panel by identifying genomic sites having cancer-specific methylation patterns as well as a list of genomic sites or genomic regions that can be used for various methods provided herein. The methods described herein further include methods of designing probes to enrich for cfDNA corresponding to or derived from selected genomic regions efficiently without pulling down an excessive amount of undesired DNA.

In one aspect, provided herein is a bait set for hybridization capture, the bait set comprising a plurality of different oligonucleotide-containing probes, wherein each of the oligonucleotide-containing probes comprises a sequence of at least 30 bases in length that is complementary to either: (1) a sequence of a genomic region; or (2) a sequence that varies from the sequence of (1) only by one or more transitions, wherein each respective transition of the one or more transitions occurs at a cytosine in the genomic region, and wherein each probe of the different oligonucleotide-containing probes is complementary to a sequence corresponding to a CpG site that is differentially methylated in cancer samples relative to non-cancer samples.

The bait set can comprise at least 500, 1,000, 2,000, 2,500, 5,000, 6,000, 7,500, 10,000, 15,000, 20,000, 25,000, 50,000 or 100,000 different oligonucleotide-containing probes. In one aspect, the CpG site is considered to be differentially methylated in cancer samples relative to non-cancer samples based on criteria comprising a number of cancer samples that comprise an anomalously methylated cfDNA fragment that overlaps the CpG site. In one aspect, the CpG site is considered to be differentially methylated in cancer samples relative to non-cancer samples based on criteria comprising $N_{cancer}$ and $N_{non-cancer}$, wherein: $N_{cancer}$ is a number of cancer samples that include a cfDNA fragment covering the CpG site that (1) has at least X CpG sites, wherein at least Y % of the CpG sites are methylated or unmethylated, wherein X is at least 4 and Y is at least 70, and (2) has a p-value rarity in non-cancerous samples of below a threshold value; and $N_{non-cancer}$ is a number of cancer samples that include a cfDNA fragment covering the CpG site that (1) has at least M CpG sites, wherein at least N % of the sites are methylated or unmethylated, wherein M is at least 4 and N is at least 70, and (2) has a p-value rarity in non-cancerous samples of below a threshold value. In one aspect, N equals X and N equals Y. In one aspect, the CpG site is considered to be differentially methylated based on criteria positively correlated with $N_{cancer}$ and negatively correlated with $N_{non-cancer}$. In one aspect, the CpG site is considered to be differentially methylated based on a ranked score of $(N_{cancer}+1)/(N_{cancer}+N_{non-cancer}+2)$.

In one aspect, in each of the different oligonucleotide-containing probes, the sequence of at least 30 bases in length can be complementary to either (1) a sequence within a genomic region selected from the genomic regions set forth in any one of Lists 1-8; or (2) a sequence that varies from the sequence of (1) only by one or more transitions, wherein each respective transition of the one or more transitions occurs at a cytosine in the genomic region. In one aspect, the plurality of different oligonucleotide-containing probes can be each conjugated to an affinity moiety. The affinity moiety can be biotin. In one aspect, for at least one of the different oligonucleotide-containing probes, the sequence of at least 30 bases can be complementary to the sequence that varies from the sequence of (1) only by one or more transitions, wherein each respective transition of the one or more transitions occurs at a cytosine in the genomic region. In another aspect, for at least 500, 1,000, 2,000, 2,500, 5,000, 6,000, 10,000, 15,000, 20,000, 25,000, or 50,000 of each of the different oligonucleotide-containing probes, the sequence of at least 30 bases can be complementary to the sequence that varies from the sequence of (1) only by one or more transitions, wherein each respective transition of the one or more transitions occurs at a cytosine in the genomic region. In one aspect, at least 80%, 90%, or 95% of the oligonucleotide-containing probes in the bait set do not include an at least 30, at least 40, or at least 45 base sequence that has 20 or more off-target regions of the genome. In another aspect, the oligonucleotide-containing probes in the bait set do not include an at least 30, at least 40, or at least 45 base sequence that has 20 or more off-targets regions of the genome. The sequence of at least 30 bases can be at least 40 bases, at least 45 bases, at least 50 bases, at least 60 bases, at least 75, or at least 100 bases in length. Each of the oligonucleotide-containing probes can have a nucleic acid sequence of at least 45, 40, 75, 100, or 120 bases in length. Each of the oligonucleotide-containing probes can have a nucleic acid sequence of no more than 300, 250, 200, or 150 bases in length.

In one aspect, the different oligonucleotide-containing probes comprise at least 500, at least 1000, at least 2,000, at least 2,500, at least 5,000, at least 6,000, at least 7,500, and least 10,000, at least 15,000, at least 20,000, or at least 25,000 different pairs of probes, wherein each pair of probes comprises a first probe and second probe, wherein the second probe differs from the first probe and overlaps with the first probe by an overlapping sequence that is at least 30, at least 40, at least 50, or at least 60 nucleotides in length. In one aspect, the bait set can include oligonucleotide-containing probes that are configured to target at least 20%, at least 25%, at least 30%, at least 40%, at least 50%, at least 60%, at least 70%, at least 80%, at least 90%, at least 95%, or 100% of the genomic regions identified in any one of Lists 1-8. In another aspect, the bait set can include oligonucleotide-containing probes that are configured to target at least 20%, at least 25%, at least 30%, at least 40%, at least 50%, at least 60%, at least 70%, at least 80%, at least 90%, at least 95%, or 100% of the genomic regions identified in List 1. The bait set can include oligonucleotide-containing probes that are configured to target at least 20%, at least 25%, at least 30%, at least 40%, at least 50%, at least 60%, at least 70%, at least 80%, at least 90%, at least 95%, or 100% of the genomic regions identified in List 3. An entirety of oligonucleotide probes in the bait set can be configured to hybridize to fragments obtained from cfDNA molecules corresponding to at least 30%, 40%, 50%, 60%, 70%, 80%, 90% or 95% of the genomic regions in a list selected from any one of Lists 1-8. An entirety of oligonucleotide-containing probes in the bait set can be configured to hybridize to fragments obtained from cfDNA molecules corresponding to at least 500, 1,000, 5000, 10,000, 15,000, 20,000, at least 25,000, or at least 30,000 genomic regions in any one of Lists 1-8. An entirety of oligonucleotide-containing probes in the bait set can be configured to hybridize to fragments obtained from cfDNA molecules corresponding to at least 50, 60, 70, 80, 90, 100, 120, 150, or 200 genomic regions in any one of Lists 1-8.

The plurality of oligonucleotide-containing probes can comprise at least 500, 1,000, 5,000, or 10,000 different subsets of probes, wherein each subset of probes comprises a plurality of probes that collectively extend across a genomic region selected from the genomic regions of any one of Lists 1-8 in a 2× tiled fashion. The plurality of probes that collectively extend across the genomic region in a 2× tiled fashion can comprise at least one pair of probes that overlap by a sequence of at least 30 bases, at least 40 bases, at least 50 bases, or at least 60 bases in length. The plurality of probes can collectively extend across portions of the genome that collectively can be a combined size of between 0.2 and 15 MB, between 0.5 MB and 15 MB, between 1 MB and 15 MB, between 3 MB and 12 MB, between 3 MB and 7, MB, between 5 MB and 9 MB, or between 7 MB and 12 MB. A subset of the different oligonucleotide-containing probes in the bait set can be designed to hybridize to cfDNA fragments derived from one or more genomics region from either List 4 or List 6. A subset of the different oligonucleotide-containing probes in the bait set can be designed to target at least 2, at least 10, at least 50, at least 100, at least 1000, or at least 5000, at least 8000, at least 10,000 or at least 20,000 of the genomic regions from either List 4 or List 6. The different oligonucleotide-containing probes can each comprise less than 20, 15, 10, 8, or 6 CpG detection sites. In one aspect, at least 80%, 85%, 90%, 92%, 95%, or 98% of the plurality of oligonucleotide-containing probes in the bait set can have exclusively either CpG or CpA on all CpG detection sites. The oligonucleotide-containing probes of the bait set can correspond with a number of genomic regions selected from the genomic regions of any one of Lists 1-8, wherein at least 30% of the genomic regions that correspond with the probes in the bait set are in exons or introns. The oligonucleotide-containing probes of the bait set can correspond with a number of genomic regions, wherein at least 15% or at least 20% of the genomic regions that correspond with probes in the bait set are in exons. The oligonucleotide-containing probes of the bait set can correspond with a number of genomic regions, wherein less than 10% of the genomic regions that correspond with probes in the bait set are intergenic regions. In one aspect, for each of the different oligonucleotide-containing probes, the at least 30 nucleotide sequence can be complementary to a sequence that varies from the sequence of the genomic region by one or more transitions at all CpG sites within the sequence. In another aspect, for oligonucleotide-containing probes that vary with respect to the sequence within the genomic region by one or more transitions, a transition can occur at each CpG site within the genomic region. The different oligonucleotide-containing probes can be complementary to cfDNA fragments that have been converted to replace cytosine with uracil, wherein the cfDNA fragments are found at least 2-fold, 10-fold, 20-fold, 50-fold, 100-fold, or 1000-fold more frequently in cfDNA from cancer subjects than from cfDNA from non-cancer subjects.

In one embodiment, provided herein is a mixture comprising a bait set and converted cfDNA. The converted cfDNA can comprise bisulfite-converted cfDNA. The converted cfDNA can comprise cfDNA that has been converted via cytosine deaminase. In one aspect, provided herein is a method for enriching a converted cfDNA sample comprising contacting the cell-free DNA sample with the bait set and enriching the sample for a first set of genomic regions by hybridization capture.

In another aspect, provided herein is a method for providing sequence information informative of a presence or absence of a cancer, a stage of cancer, or a type of cancer, the method comprising: processing cell-free DNA from a biological sample with a deaminating agent to generate a cell-free DNA sample comprising deaminated nucleotides; and enriching the cell-free DNA sample for informative cell-free DNA molecules, wherein enriching the cell-free DNA sample for informative cell-free DNA molecules comprises contacting the cell-free DNA with a plurality of probes that are configured to hybridize to cell-free DNA molecules that correspond to regions identified in any one of Lists 1-8; and sequencing the enriched cell-free DNA molecules, thereby obtaining a set of sequence reads informative of a presence or absence of a cancer, a stage of cancer, or a type of cancer. The plurality of probes can comprise a plurality of primers, and enriching the cell-free DNA comprises amplifying, via PCR, the cell-free DNA fragments using the primers. In one aspect, enriching the cell-free DNA does not involve hybridization capture. In one aspect, the plurality of probes can be configured to hybridize to converted fragments obtained from the cfDNA molecules corresponding to or derived from at least 30%, 40%, 50%, 60%, 70%, 80%, 90% or 95% of the genomic regions in any one of Lists 1-8. The plurality of probes can comprise a plurality of oligonucleotide-containing probes.

In another aspect, the method further comprises determining a cancer classification by evaluating the set of sequence reads, wherein the cancer classification is (a) a presence or absence of cancer; (b) a stage of cancer; or (c) a presence or absence of a type of cancer. The cancer classification can be a presence or absence of cancer. The cancer classification can be a stage of cancer. The stage of cancer can be selected from Stage I, Stage II, Stage III, and Stage IV. The cancer classification can be a presence or absence of a type of cancer. In one aspect, the step of determining a cancer classification can further comprise: (a) generating a test feature vector based on the set of sequence reads; and (b) applying the test feature vector to a classifier. In one aspect, the classifier further comprises a model trained by a training process with a cancer set of fragments from one or more training subjects with cancer and a non-cancer set of fragments from one or more training subjects without cancer, wherein both cancer set of fragments and the non-cancer set of fragments comprise a plurality of training fragments. The classifier can have an area under a receiver operating characteristic curve of greater than 0.70, greater than 0.75, greater than 0.77, greater than 0.80, greater than 0.81, greater than 0.82, or greater than 0.83. At 99% specificity, the classifier can have a sensitivity of at least 35%, at least 40%, at least 45% or at least 50%. In one aspect, the step of determining a cancer classification further comprises: (a) generating a test feature vector based on the set of sequence reads; and (b) applying the test feature vector to a classifier. In one aspect, the classifier comprises a model trained by a training process with a cancer set of fragments from one or more training subjects with cancer and a non-cancer set of fragments from one or more training subjects without cancer, wherein both cancer set of fragments and the non-cancer set of fragments comprise a plurality of training fragments.

In one aspect, the type of cancer can be selected from the group consisting of head and neck cancer, liver/bile duct cancer, upper GI cancer, pancreatic/gallbladder cancer; colorectal cancer, ovarian cancer, lung cancer, multiple myeloma, lymphoid neoplasms, melanoma, sarcoma, breast cancer, and uterine cancer. In one aspect, the classifier, at 99.4% specificity, has a sensitivity of at least 70%, at least 80%, at least 85%, or at least 87% in classifying head and neck cancer. The classifier, at 99.4% specificity can have a sensitivity of at least 60%, at least 65%, at least 70%, or at least 73% in classifying liver/bile duct cancer. The classifier, at 99.4% specificity, can have a sensitivity of at least 70%, at least 75%, at least 80%, or at least 85% in classifying upper GI tract cancer. The classifier, at 99.4% specificity, can have a sensitivity of at least 70%, at least 80%, at least 85%, or at least 90% in classifying pancreatic/gall bladder cancer. The classifier, at 99.4% specificity can have a sensitivity of at least 70%, at least 80%, at least 90%, at least 95%, or at least 98% in classifying colorectal cancer. The classifier, at 99.4% specificity, can have a sensitivity of at least 70%, at least 80%, at least 85%, or at least 87% in classifying ovarian cancer. The classifier, at 99.4% specificity, can have a sensitivity of at least 70%, at least 80%, at least 90%, at least 95%, or at least 97% in classifying lung cancer. The classifier, at 99.4% specificity, can have a sensitivity of at least 70%, at least 80%, at least 85%, or at least 90% or at least 93% in classifying multiple myeloma. The classifier, at 99.4% specificity, can have a sensitivity of at least 70%, at least 80%, at least 90%, or at least 95% or at least 98% in classifying lymphoid neoplasm. The classifier, at 99.4% specificity, can have a sensitivity of at least 70%, at least 80%, at least 90%, or at least 95% or at least 98% in classifying melanoma. The classifier, at 99.4% specificity, can have a sensitivity of at least 35%, at least 40%, at least 45%, or at least 50% in classifying sarcoma. The classifier, at 99.4% specificity, can have a sensitivity of at least 70%, at least 80%, at least 90%, or at least 95% or at least 98% in classifying breast cancer. The classifier, at 99.4% specificity, can have a sensitivity of at least 70%, at least 80%, at least 90%, or at least 95% or at least 97% in classifying uterine cancer.

In another aspect, provided herein a method for determining a cancer classification comprising the steps of a) generating a test feature vector based on the set of sequence reads; and b) applying the test feature vector to a model obtained by a training process with a cancer set of fragments from one or more training subjects with a cancer and a non-cancer set of fragments from one or more training subjects without cancer, wherein both the cancer set of fragments and the non-cancer set of fragments comprise a plurality of training fragments. The training process can comprise: (a) obtaining sequence information of training fragments from a plurality of training subjects; (b) for each training fragment, determining whether that training fragment is hypomethylated or hypermethylated, wherein each of the hypomethylated and hypermethylated training fragments comprises at least a threshold number of CpG sites with at least a threshold percentage of the CpG sites being unmethylated or methylated, respectively, (c) for each training subject, generating a training feature vector based on the hypomethylated training fragments and hypermethylated training fragments, and (d) training the model with the training feature vectors from the one or more training subjects without cancer and the training feature vectors from the one or more training subjects with cancer. In another aspect, the training process comprises: (a) obtaining sequence information of training fragments from a plurality of training subjects; (b) for each training fragment, determining whether that training fragment is hypomethylated or hypermethylated, wherein each of the hypomethylated and hypermethylated training fragments comprises at least a threshold number of CpG sites with at least a threshold percentage of the CpG sites being unmethylated or methylated, respectively, (c) for each of a plurality of CpG sites in a reference genome: quantifying a count of hypomethylated training fragments which overlap the CpG site and a count of hypermethylated training fragments which overlap the CpG site; and generating a hypomethylation score and a hypermethylation score based on the count of hypomethylated training fragments and hypermethylated training fragments; (d) for each training fragment, generating an aggregate hypomethylation score based on the hypomethylation score of the CpG sites in the training fragment and an aggregate hypermethylation score based on the hypermethylation score of the CpG sites in the training fragment; (e) for each training subject: ranking the plurality of training fragments based on aggregate hypomethylation score and ranking the plurality of training fragments based on aggregate hypermethylation score; and generating a feature vector based on the ranking of the training fragments; (f) obtaining training feature vectors for one or more training subjects without cancer and training feature vectors for the one or more training subjects with cancer; and (g) training the model with the feature vectors for the one or more training subjects without cancer and the feature vectors for the one or more training subjects with cancer. The model can comprise one of a kernel logistic regression classifier, a random forest classifier, a mixture model, a convolutional neural network, and an autoencoder model. In another aspect, the method further comprises the steps of: obtaining a cancer probability for the test sample based on the model; and comparing the cancer probability to a threshold probability to determine whether the test sample is from a subject with cancer or without cancer. The method can further comprise administering an anti-cancer agent to the subject.

In another aspect, provided herein is a method of treating a cancer patient, the method comprising, identified as a cancer subject by the methods above and administering an anti-cancer agent to a subject. The anti-cancer agent can be a chemotherapeutic agent selected from the group consisting of alkylating agents, antimetabolites, anthracyclines, anti-tumor antibiotics, cytoskeletal disruptors (taxans), topoisomerase inhibitors, mitotic inhibitors, corticosteroids, kinase inhibitors, nucleotide analogs, and platinum-based agents.

Provided herein is a method for assessing whether a subject has a cancer, the method comprising:

obtaining cfDNA from the subject; isolating a portion of the cfDNA from the subject by hybridization capture; obtaining sequence reads derived from the captured cfDNA to determine methylation states cfDNA fragments; applying a classifier to the sequence reads; and determining whether the subject has cancer based on application of the classifier; wherein the classifier has an area under the receiver operator characteristic curve of greater than 0.70, greater than 0.75, greater than 0.77, greater than 0.80, greater than 0.81, greater than 0.82, or greater than 0.83. In one aspect, the method further comprises converting unmethylated cytosines in the cfDNA to uracil prior to isolating the portion of the cfDNA from the subject by hybridization capture. In another aspect, the method further comprises converting unmethylated cytosines in the cfDNA to uracil after isolating the portion of the cfDNA from the subject by hybridization capture. The classifier can be a binary classifier. In one aspect, isolating a portion of the cfDNA from the subject by hybridization capture comprises contacting the cell-free DNA with a bait set comprising a plurality of different oligonucleotide-containing probes.

In another aspect, provided herein is a method for identifying genomic regions that exhibit differential methylation in cancer samples relative to non-cancer samples, the method comprising: (a) obtaining sequence reads of converted cfDNA from both cancer subjects and non-cancer subjects; (b) identifying, based on the sequence reads, cfDNA fragments that: (i) have a p-value rarity in non-cancerous samples of below a threshold value; and (ii) have at least X CpG sites, wherein at least Y % of the CpG sites are methylated, wherein X is at least 4, 5, 6, 7, 8, 9, or 10 and Y is at least 70; and (c) for each of a plurality of CpG sites in a reference genome, counting both (1) a number of cancer subjects ($N_{cancer}$) and (2) a number of non-cancer subjects ($N_{noncancer}$) that have a fragment identified in step (b); (d) for each of the plurality of CpG sites in the reference genome, determining whether the CpG site is differentially methylated in cancer samples based on criteria comprising $N_{cancer}$ and $N_{non-cancer}$; (e) identifying a genomic region as differentially methylated in cancer based, at least in part, on inclusion of a differentially methylated CpG site within the genomic region. In another aspect, provided herein is a method for identifying genomic regions that exhibit differential methylation in cancer samples relative to non-cancer samples, the method comprising:

(a) obtaining sequence reads of converted cfDNA from both cancer subjects and non-cancer subjects; (b) identifying, based on the sequence reads, cfDNA fragments that: (i) have at least X CpG sites, wherein at least Y % of the CpG sites are unmethylated, wherein X is 4, 5, 6, 7, 8, 9, or 10 and Y is at least 70; and (ii) have a p-value rarity in non-cancerous samples of below a threshold value;

(c) for each of a plurality of CpG sites in a reference genome, counting both (1) a number of cancer subjects ($N_{cancer}$) and (2) a number of non-cancer subjects ($N_{noncancer}$) that have a fragment identified in step (b); (d) for each of the plurality of CpG sites in the reference genome, determining whether the CpG site is differentially methylated in cancer samples based on criteria comprising $N_{cancer}$ and $N_{non-cancer}$; (e) identifying a genomic region as differentially methylated in cancer based, at least in part, on inclusion of a differentially methylated CpG site within the genomic region. In one aspect, the CpG site is considered to be differentially methylated based on criteria positively correlated with $N_{cancer}$ and negatively correlated with $N_{non-cancer}$. In one aspect, the CpG site is considered to be differentially methylated when $(N_{cancer+1})/(N_{cancer}+N_{non-cancer}+2)$ is greater than a threshold value. Each of the identified genomic regions can have at least X CpG sites, wherein X is 4, 5, or 6. In one aspect, at least 10%, at least 20%, at least 30%, at least 40%, at least 50%, at least 60%, at least 70%, at least 80%, or at least 90% of the identified regions are from any one of Lists 1-8.

In one aspect, provided herein is a method for developing a bait set for hybridization capture of cfDNA from genomic regions that are differentially methylated between cancer and non-cancer, the method comprising: identifying at least 1000, at least 5,000, at least 10,000, at least 25,000, or at least 30,000 differentially methylated genomic regions of the genome by comparison of one or more parameters derived from cfDNA fragments from cancer subject to one or more parameters derived from cfDNA fragments from non-cancer subjects; and designing, in silico, a plurality of oligonucleotide-containing probes that include a sequence of at least 30 bases in length that is complementary to either (1) a sequence of a genomic region or (2) a sequence that differs from the sequence of the genomic region only by one or more transitions, wherein each respective transition occurs at a cytosine in the genomic region. The method can further comprise removing, in silico, probes that have at least X off-target regions, wherein X is at least one. X can be at least 5, at least 10, or at least 20. The method can further comprise synthesizing the oligonucleotide-containing probes that were designed in silico.

In one aspect, provided herein is a method for selecting probes for hybridization capture of cfDNA, the method comprising: identifying a first set of genomic regions that are preferentially hypermethylated in cfDNA from cancer subjects relative to non-cancer subjects; identifying a second set of genomic regions that are preferentially hypomethylated in cfDNA from cancer subjects relative to non-cancer subjects; and selecting probes for hybridization capture of cfDNA corresponding to the first set of genomic regions and the second set of genomic regions, wherein the probes comprise a first set of probes for hybridization capture of cfDNA corresponding to the first set of genomic regions and a second set of probes for hybridization capture of cfDNA corresponding to the second set of genomic regions; wherein the probes comprise at least 500, at least 1,000, at least 2,500, at least 5,000, at least 10,000, at least 20,000 subsets of probes, wherein each subset of probes comprises a plurality of probes that extend across a genomic region in a 2× tiled fashion. The second set of probes for hybridization capture can comprise selecting probes that differ from a sequence in the genomic region only by one or more transitions, wherein each transition occurs at a nucleotide corresponding to a cytosine in the genomic region. In one aspect, selecting probes for hybridization capture can comprise filtering out probes that have more than a threshold number of off-target regions. Each subset of probes can comprise at least three probes. Each probe can be between 75 and 200, between 100 and 150, between 110 and 130, or 120 nucleotides in length.

In another aspect, provided herein is an assay panel for enriching cfDNA molecules for cancer diagnosis, the assay panel comprising: at least 500 different pairs of polynucleotide probes, wherein each pair of the at least 500 pairs of probes (i) comprises two different probes configured to overlap with each other by an overlapping sequence of 30 or more nucleotides and (ii) is configured to hybridize to a modified fragment obtained from processing of the cfDNA molecules, wherein each of the cfDNA molecules corresponds to or is derived from one or more genomic regions, wherein each of the one or more genomic regions comprises at least five methylation sites and has an anomalous methylation pattern in cancerous training samples relative to non-cancerous training samples. The overlapping sequence can comprise at least 40, 50, 75, or 100 nucleotides. The assay panel can comprise at least 1,000, 2,000, 2,500, 5,000, 6,000, 7,500, 10,000, 15,000, 20,000, or 25,000 pairs of probes.

In another aspect, provided herein is an assay panel for enriching cfDNA molecules for cancer diagnosis, the assay panel comprising: at least 1,000 polynucleotide probes, wherein each of the at least 1,000 probes is configured to hybridize to a modified polynucleotide obtained from processing of the cfDNA molecules, wherein each of the cfDNA molecules corresponds to or is derived from, one or more genomic regions, wherein each of the one or more genomic regions comprises at least five methylation sites, and has an anomalous methylation pattern in cancerous training samples relative to non-cancerous samples. The processing of the cfDNA molecules can comprise converting unmethylated C (cytosine) to U (uracil) in the cfDNA molecules. Each of the polynucleotide probes on the panel can be conjugated to an affinity moiety. The affinity moiety can be a biotin moiety. Each of the one or more genomic regions can be either hypermethylated or hypomethylated in the cancerous training samples relative to non-cancerous reference samples. In one aspect, at least 80%, 85%, 90%, 92%, 95%, or 98% of the probes on the panel can have exclusively either CpG or CpA on CpG detection sites. Each of the probes on the panel can comprise less than 20, 15, 10, 8, or 6 CpG detection sites. Each of the probes on the panel can be designed to have fewer than 20, 15, 10, or 8 off-target genomic regions. In one aspect, the fewer than 20 off-target genomic regions can be identified using a k-mer seeding strategy. In another aspect, the fewer than 20 off-target genomic regions can be identified using k-mer seeding strategy combined to local alignment at seed locations.

The assay panel can comprise at least 1,000, 2,000, 2,500, 5,000, 10,000, 12,000, 15,000, 20,000, or 25,000 probes. In one aspect, at least 500 pairs of probes or the at least 1,000 probes together can comprise at least 0.2 million, 0.4 million, 0.6 million, 0.8 million, 1 million, 2 million, 4 million, or 6 million nucleotides. Each of the probes on the panel can comprise at least 50, 75, 100, or 120 nucleotides. Each of the probes on the panel can comprise less than 300, 250, 200, or 150 nucleotides. Each of the probes on the panel can comprise 100-150 nucleotides. In one aspect, at least 30% of the genomic regions are in exons or introns. In another aspect, at least 15% of the genomic regions can be in exons. In another aspect, at least 20% of the genomic regions can be in exons. Each of the one or more genomic regions can be selected from one of Lists 1-8. An entirety of probes on the assay panel together can be configured to hybridize to modified fragments obtained from the cfDNA molecules corresponding to or derived from at least 30%, 40%, 50%, 60%, 70%, 80%, 90% or 95% of the genomic regions in one or more of Lists 1-8. An entirety of probes on the assay panel together are configured to hybridize to modified fragments obtained from the cfDNA molecules corresponding to or derived from at least 500, 1,000, 5000, 10,000 or 15,000 genomic regions in one or more of Lists 1-8. The processing of the cfDNA molecules can comprise converting unmethylated C (cytosine) to U (uracil) in the cfDNA molecules. Each of probes on the panel can be conjugated to an affinity moiety. The affinity moiety can be biotin. At least 80%, 85%, 90%, 92%, 95%, or 98% of the probes on the panel can have exclusively either CpG or CpA on CpG detection sites.

In another aspect, provided herein is a method of providing sequence information informative of a presence or absence of cancer, the method comprising the steps of: (a) obtaining a test sample comprising a plurality of cfDNA test molecules; (b) processing the cfDNA test molecules, thereby obtaining converted test fragments; (c) contacting the converted test fragments with an assay panel, thereby enriching a subset of the converted test fragments by hybridization capture; and (d) sequencing the subset of the converted test fragments, thereby obtaining a set of sequence reads. The converted test fragments can be bisulfite-converted test fragments. In another aspect, the method further comprises determining a cancer classification by evaluating the set of sequence reads, wherein the cancer classification is (a) a presence or absence of cancer; (b) a stage of cancer; (c) a presence or absence of a type of cancer. In one aspect, the step of determining a cancer classification can comprise: (a) generating a test feature vector based on the set of sequence reads; and (b) applying the test feature vector to a classifier. The classifier can comprise a model trained by a training process with a cancer set of fragments from one or more training subjects with cancer and a non-cancer set of fragments from one or more training subjects without cancer, wherein both cancer set of fragments and the non-cancer set of fragments comprise a plurality of training fragments. The classifier can have an area under a receiver operating characteristic curve of greater than 0.70, greater than 0.75, greater than 0.77, greater than 0.80, greater than 0.81, greater than 0.82, or greater than 0.83. At 99% specificity, the classifier can have a sensitivity of at least 35%, at least 40%, at least 45% or at least 50%. In another aspect, the step of determining a cancer classification further comprises: (a) generating a test feature vector based on the set of sequence reads; and (b) applying the test feature vector to a classifier. The classifier can comprise a model trained by a training process with a cancer set of fragments from one or more training subjects with cancer and a non-cancer set of fragments from one or more training subjects without cancer, wherein both cancer set of fragments and the non-cancer set of fragments comprise a plurality of training fragments.

The type of cancer can be selected from the group consisting of head and neck cancer, liver/bile duct cancer, upper GI cancer, pancreatic/gallbladder cancer; colorectal cancer, ovarian cancer, lung cancer, multiple myeloma, lymphoid neoplasms, melanoma, sarcoma, breast cancer, and uterine cancer. In one aspect, the classifier, at 99.4% specificity, has a sensitivity of at least 70%, at least 80%, at least 85%, or at least 87% for classifying head and neck cancer. The classifier, at 99.4% specificity can have a sensitivity of at least 60%, at least 65%, at least 70%, or at least 73% for classifying liver/bile duct cancer. The classifier, at 99.4% specificity, can have a sensitivity of at least 70%, at least 75%, at least 80%, or at least 85% for classifying upper GI tract cancer. The classifier, at 99.4% specificity, can have a sensitivity of at least 70%, at least 80%, at least 85%, or at least 90% for classifying pancreatic/gall bladder cancer. The classifier, at 99.4% specificity can have a sensitivity of at least 70%, at least 80%, at least 90%, at least 95%, or at least 98% in classifying colorectal cancer. The classifier, at 99.4% specificity, can have a sensitivity of at least 70%, at least 80%, at least 85%, or at least 87% in classifying ovarian cancer. The classifier, at 99.4% specificity, can have a sensitivity of at least 70%, at least 80%, at least 90%, at least 95%, or at least 97% in classifying lung cancer. The classifier, at 99.4% specificity, can have a sensitivity of at least 70%, at least 80%, at least 85%, or at least 90% or at least 93% in classifying multiple myeloma. The classifier, at 99.4% specificity, can have a sensitivity of at least 70%, at least 80%, at least 90%, or at least 95% or at least 98% in classifying lymphoid neoplasm. The classifier, at 99.4% specificity, can have a sensitivity of at least 70%, at least 80%, at least 90%, or at least 95% or at least 98% in classifying melanoma. The classifier, at 99.4% specificity, can have a sensitivity of at least 35%, at least 40%, at least 45%, or at least 50% in classifying sarcoma. The classifier, at 99.4% specificity, can have a sensitivity of at least 70%, at least 80%, at least 90%, or at least 95% or at least 98% in classifying breast cancer. The classifier, at 99.4% specificity, can have a sensitivity of at least 70%, at least 80%, at least 90%, or at least 95% or at least 97% in classifying uterine cancer.

In one aspect, the method of cancer classification further comprises the steps of: (a) generating a test feature vector based on the set of sequence reads; and (b) applying the test feature vector to a model obtained by a training process with a cancer set of fragments from one or more training subjects with a cancer and a non-cancer set of fragments from one or more training subjects without cancer, wherein both the cancer set of fragments and the non-cancer set of fragments comprise a plurality of training fragments. The training process can comprise: (a) obtaining sequence information of training fragments from a plurality of training subjects; (b) for each training fragment, determining whether that training fragment is hypomethylated or hypermethylated, wherein each of the hypomethylated and hypermethylated training fragments comprises at least a threshold number of CpG sites with at least a threshold percentage of the CpG sites being unmethylated or methylated, respectively, (c) for each training subject, generating a training feature vector based on the hypomethylated training fragments and a training feature vector based on the hypermethylated training fragments, and (d) training the model with the training feature vectors from the one or more training subjects without cancer and the training feature vectors from the one or more training subjects with cancer. The training process can further comprise: (a) obtaining sequence information of training fragments from a plurality of training subjects; (b) for each training fragment, determining whether that training fragment is hypomethylated or hypermethylated, wherein each of the hypomethylated and hypermethylated training fragments comprises at least a threshold number of CpG sites with at least a threshold percentage of the CpG sites being unmethylated or methylated, respectively, (c) for each of a plurality of CpG sites in a reference genome: quantifying a count of hypomethylated training fragments which overlap the CpG site and a count of hypermethylated training fragments which overlap the CpG site; and generating a hypomethylation score and a hypermethylation score based on the count of hypomethylated training fragments and hypermethylated training fragments; (d) for each training fragment, generating an aggregate hypomethylation score based on the hypomethylation score of the CpG sites in the training fragment and an aggregate hypermethylation score based on the hypermethylation score of the CpG sites in the training fragment; (e) for each training subject: ranking the plurality of training fragments based on aggregate hypomethylation score and ranking the plurality of training fragments based on aggregate hypermethylation score; and generating a feature vector based on the ranking of the training fragments; (f) obtaining training feature vectors for one or more training subjects without cancer and training feature vectors for the one or more training subjects with cancer; and (g) training the model with the feature vectors for the one or more training subjects without cancer and the feature vectors for the one or more training subjects with cancer. The model can comprise one of a kernel logistic regression classifier, a random forest classifier, a mixture model, a convolutional neural network, and an autoencoder model. In one aspect, the method of cancer classification can further comprise the steps of: (a) obtaining a cancer probability for the test sample based on the model; and (b) comparing the cancer probability to a threshold probability to determine whether the test sample is from a subject with cancer or without cancer. In one aspect, the method of identifying a cancer subject can further comprise administering an anti-cancer agent to the subject. The anti-cancer agent can be a chemotherapeutic agent selected from the group consisting of alkylating agents, antimetabolites, anthracyclines, anti-tumor antibiotics, cytoskeletal disruptors (taxans), topoisomerase inhibitors, mitotic inhibitors, corticosteroids, kinase inhibitors, nucleotide analogs, and platinum-based agents.

In another aspect, provided herein is a method comprising the steps of: (a) obtaining a set of sequence reads of modified test fragments, wherein the modified test fragments are or have been obtained by processing a set of nucleic acid fragments from a test subject, wherein each of the nucleic acid fragments corresponds to or is derived from a plurality of genomic regions selected from any one of Lists 1-8; and (b) applying the set of sequence reads or a test feature vector obtained based on the set of sequence reads to a model obtained by a training process with a cancer set of fragments from one or more training subjects with cancer and a non-cancer set of fragments from one or more training subjects without cancer, wherein both cancer set of fragments and the non-cancer set of fragments comprise a plurality of training fragments. The method can further comprise the step of obtaining the test feature vector comprising: (a) for each of the nucleic acid fragments, determining whether the nucleic acid fragment is hypomethylated or hypermethylated, wherein each of the hypomethylated and hypermethylated nucleic acid fragments comprises at least a threshold number of CpG sites with at least a threshold percentage of the CpG sites being unmethylated or methylated, respectively; (b) for each of a plurality of CpG sites in a reference genome: quantifying a count of hypomethylated nucleic acid fragments which overlap the CpG site and a count of hypermethylated nucleic acid fragments which overlap the CpG site; and generating a hypomethylation score and a hypermethylation score based on the count of hypomethylated nucleic acid fragments and hypermethylated nucleic acid fragments; (c) for each nucleic acid fragment, generating an aggregate hypomethylation score based on the hypomethylation score of the CpG sites in the nucleic acid fragment and an aggregate hypermethylation score based on the hypermethylation score of the CpG sites in the nucleic acid fragment; (d) ranking the plurality of nucleic acid fragments based on aggregate hypomethylation score and ranking the plurality of nucleic fragments based on aggregate hypermethylation score; and (e) generating the test feature vector based on the ranking of the nucleic acid fragments. The training process can comprise: (a) for each training fragment, determining whether that training fragment is hypomethylated or hypermethylated, wherein each of the hypomethylated and hypermethylated training fragments comprises at least a threshold number of CpG sites with at least a threshold percentage of the CpG sites being unmethylated or methylated, respectively, (b) for each training subject, generating a training feature vector based on the hypomethylated training fragments and a training feature vector based on the hypermethylated training fragments, and (c) training the model with the training feature vectors from the one or more training subjects without cancer and the feature vectors from the one or more training subjects with cancer. The training process can comprise: (a) for each training fragment, determining whether that training fragment is hypomethylated or hypermethylated, wherein each of the hypomethylated and hypermethylated training fragments comprises at least a threshold number of CpG sites with at least a threshold percentage of the CpG sites being unmethylated or methylated, respectively, (b) for each of a plurality of CpG sites in a reference genome: quantifying a count of hypomethylated training fragments which overlap the CpG site and a count of hypermethylated training fragments which overlap the CpG site; and generating a hypomethylation score and a hypermethylation score based on the count of hypomethylated training fragments and hypermethylated training fragments; (c) for each training fragment, generating an aggregate hypomethylation score based on the hypomethylation score of the CpG sites in the training fragment and an aggregate hypermethylation score based on the hypermethylation score of the CpG sites in the training fragment; (d) for each training subject:

ranking the plurality of training fragments based on aggregate hypomethylation score and ranking the plurality of training fragments based on aggregate hypermethylation score; and generating a feature vector based on the ranking of the training fragments; (e) obtaining training feature vectors for one or more training subjects without cancer and training feature vectors for the one or more training subjects with cancer; and (f) training the model with the feature vectors for the one or more training subjects without cancer and the feature vectors for the one or more training subjects with cancer.

In one aspect, the method can further comprise quantifying a count of hypomethylated training fragments which overlap that CpG site and a count of hypermethylated training fragments which overlap that CpG site for each CpG site in a reference genome comprising the steps of: (a) quantifying a cancer count of hypomethylated training fragments from the one or more training subjects with cancer that overlap that CpG site and a non-cancer count of hypomethylated training fragments from the one or more training subjects without cancer that overlap that CpG site; and (b) quantifying a cancer count of hypermethylated training fragments from the one or more training subjects with cancer that overlap that CpG site and a non-cancer count of hypermethylated training fragments from the one or more training subjects without cancer that overlap that CpG site. For each CpG site in a reference genome, generating a hypomethylation score and a hypermethylation score based on the count of hypomethylated training fragments and hypermethylated training fragments further comprises: (a) for generating the hypomethylation score, calculating a hypomethylation ratio of the cancer count of hypomethylated training fragments over a hypomethylation sum of the cancer count of hypomethylated training fragments and the non-cancer count of hypomethylated training fragments; and (b) for generating the hypermethylation score, calculating a hypermethylation ratio of the cancer count of hypermethylated training fragments over a hypermethylation sum of the cancer count of hypermethylated training fragments and the non-cancer count of hypermethylated training fragments. The model can comprise one of a kernel logistic regression classifier, a random forest classifier, a mixture model, a convolutional neural network, and an autoencoder model. In one aspect, the set of sequence reads can be obtained by using the assay panel described in this invention.

In one aspect, provided herein is a method of designing an assay panel for cancer diagnosis, comprising the steps of: (a) identifying a plurality of genomic regions, wherein each of the plurality of genomic regions (i) comprises at least 30 nucleotides, and (ii) comprises at least five methylation sites, (b) selecting a subset of the genomic regions, wherein the selection is made when cfDNA molecules corresponding to or derived from each of the genomic regions in cancer training samples have an anomalous methylation pattern, wherein the anomalous methylation pattern comprises at least five methylation sites known to be, or identified as, either hypomethylated or hypermethylated, and (c) designing the assay panel comprising a plurality of probes, wherein each of the probes is configured to hybridize to a modified fragment obtained from processing cfDNA molecules corresponding to or derived from one or more of the subset of the genomic regions. The processing of the cfDNA molecules can comprise converting unmethylated C (cytosine) to U (uracil) in the cfDNA molecules.

In another aspect, provided herein is a cancer assay panel, comprising: at least 500 pairs of probes, wherein each pair of the at least 500 pairs comprises two probes configured to overlap each other by an overlapping sequence, wherein the overlapping sequence comprises a 30-nucleotide sequence, and wherein the 30-nucleotide sequence is configured to have sequence complementarity with one or more genomic regions, wherein the one or more genomic regions have at least five methylation sites, and wherein the at least five methylation sites have an abnormal methylation pattern in non-cancerous samples or cancerous samples. The overlapping sequence comprises at least 40, 50, 75, or 100 nucleotides. The cancer assay panel can comprise at least 1,000, 2,000, 2,500, 5,000, 6,000, 7,500, 10,000, 15,000, 20,000 or 25,000 pairs of probes.

In another aspect, provided herein is a cancer assay panel, comprising: at least 1,000 probes, wherein each of the probes is designed as a hybridization probe complementary to one or more genomic regions, wherein each of the genomic regions comprises: (i) at least 30 nucleotides, and (ii) at least five methylation sites, wherein the at least five methylation sites have an abnormal methylation pattern and are either hypomethylated or hypermethylated in cancerous samples or non-cancerous samples. The abnormal methylation pattern can have at least a threshold p-value rarity in the non-cancerous samples. In one aspect, each of the probes is designed to have less than 20 off-target genomic regions. In one aspect, the less than 20 off-target genomic regions are identified using a k-mer seeding strategy. In another aspect, the less than 20 off-target genomic regions are identified using k-mer seeding strategy combined to local alignment at seed locations.

In one aspect, each of the genomic regions can be selected based on criteria comprising: (a) a number ($N_{cancer}$) of the cancerous samples including at least one cfDNA fragment having the abnormal methylation pattern; and (b) a number ($N_{non-cancer}$) of the non-cancerous samples including at least one cfDNA fragment having the abnormal methylation pattern. Each of the genomic regions can be selected based on criteria positively correlated to $N_{cancer}$ and inversely correlated to the sum of $N_{cancer}$ and $N_{non-cancer}$. comprising at least 1,000, 2,000, 2,500, 5,000, 10,000, 12,000, 15,000, 20,000, 30,000, 40,000, or 50,000 probes. In one aspect, the at least 500 pairs of probes or the at least 1,000 probes together comprise at least 0.2 million, 0.4 million, 0.6 million, 0.8 million, 1 million, 2 million, 3 million, 4 million, 5 million, or 6 million nucleotides. Each of the probes can comprise at least 50, 75, 100, or 120 nucleotides. Each of the probes can comprise less than 300, 250, 200, or 150 nucleotides. Each of the probes can comprise 100-150 nucleotides. Each of the probes can comprise less than 20, 15, 10, 8, or 6 methylation sites. In one aspect, at least 80%, 85%, 90%, 92%, 95%, or 98% of the at least five methylation sites are either methylated or unmethylated in the cancerous samples.

In one aspect, each of the probes is configured to have less than 20, 15, 10, or 8 off-target genomic regions. In one aspect, at least 30% of the genomic regions are in exons or introns. In another aspect, at least 15% of the genomic regions are in exons. In another aspect, at least 20% of the genomic regions are in exons. In another aspect, less than 10% of the genomic regions are in intergenic regions. The genomic regions can be selected from any one of Lists 1-8. The genomic regions can be selected from List 3. The genomic regions can be selected from List 8. The genomic regions can comprise at least 20%, 30%, 40%, 50%, 60%, 70%, 80%, 90% or 95% of the genomic regions in any one of Lists 1-8. The genomic regions can comprise at least 20%, 30%, 40%, 50%, 60%, 70%, 80%, 90% or 95% of the genomic regions in List 3. The genomic regions can comprise at least 20%, 30%, 40%, 50%, 60%, 70%, 80%, 90% or 95% of the genomic regions in List 5. The genomic regions can comprise at least 20%, 30%, 40%, 50%, 60%, 70%, 80%, 90% or 95% of the genomic regions in List 8. In one aspect, the at least 1,000 or at least 2,000 probes are configured to be complementary to at least 500, 1,000, 5000, 10,000 or 15,000 genomic regions in any one of Lists 1-8. In another aspect, the at least 1,000 or at least 2,000 probes are configured to be complementary to at least 500, 1,000, 5000, 10,000 or 15,000 genomic regions in List 3. In another aspect, the at least 1,000 or at least 2,000 probes are configured to be complementary to at least 500, 1,000, 5000, 10,000 or 15,000 genomic regions in List 5. In another aspect, the at least 1,000 or at least 2,000 probes are configured to be complementary to at least 1,000, 5000, 10,000 or 15,000 genomic regions in List 8. The 30-nucleotide sequence can comprise at least five CpG detection sites, wherein at least 80% of the at least five CpG detection sites comprise CpG, UpG, or CpA.

Provided herein is a cancer assay method comprising: receiving a sample comprising a plurality of nucleic acid fragments; treating the plurality of nucleic acid fragments to convert unmethylated cytosine to uracil, thereby obtaining a plurality of converted nucleic acid fragments; hybridizing the plurality of converted nucleic acid fragments with the probes on the cancer assay panel of any of above claims; enriching a subset of the plurality of converted nucleic acid fragments; and sequencing the enriched subset of the converted nucleic acid fragments, thereby providing a set of sequence reads. The method can further comprise the step of: determining a health condition by evaluating the set of sequence reads, wherein the health condition is (i) a presence or absence of cancer, or (ii) a stage of cancer. The set of nucleic acid fragments can be obtained from a human subject.

In another aspect, provided herein is a method for diagnosing cancer, comprising the steps of:

(a) obtaining a set of sequence reads by sequencing a set of nucleic acid fragments from a subject;

(b) determining methylation status of a plurality of genomic regions, the plurality of genomic regions comprise genomic regions selected from the genomic regions in any one of Lists 1-8; and (c) determining a health condition of the subject by evaluating the methylation status, wherein the health condition is (i) a presence or absence of cancer; or (ii) a stage of cancer. The genomic regions can be selected from List 3. The genomic regions can be selected from List 5. The genomic regions can be selected from List 8.

In another aspect, provided herein is a method for diagnosing cancer, comprising the steps of:

(a) obtaining a set of sequence reads by sequencing a set of nucleic acid fragments from a subject;

(b) determining methylation status of a plurality of genomic regions, the plurality of genomic regions comprise at least 20%, 30%, 40%, 50%, 60%, 70%, 80%, 90% or 95% of the genomic regions in any one of Lists 1-8; and (c) determining a health condition of the subject by evaluating the methylation status, wherein the health condition is (i) a presence or absence of cancer; or (ii) a stage of cancer. The genomic regions can comprise at least 20%, 30%, 40%, 50%, 60%, 70%, 80%, 90% or 95% of the genomic regions in List 3. The genomic regions can comprise at least 20%, 30%, 40%, 50%, 60%, 70%, 80%, 90% or 95% of the genomic regions in List 5. The genomic regions can comprise at least 20%, 30%, 40%, 50%, 60%, 70%, 80%, 90% or 95% of the genomic regions in List 8.

In another aspect, provided herein is a method for diagnosing cancer, comprising the steps of:

(a) obtaining a set of sequence reads by sequencing a set of nucleic acid fragments from a subject;

(b) determining methylation status of a plurality of at least 1,000, 2,000, 2,500, 5,000, 6,000, 7,500, 10,000, 15,000, 20,000 or 25,000 genomic regions among genomic regions in any one of Lists 1-8; and (c) determining a health condition of the subject by evaluating the methylation status, wherein the health condition is (i) a presence or absence of cancer; or (ii) a stage of cancer. In one aspect, at least 1,000, 2,000 probes can be configured to be complementary to at least 500, 1,000, 5000, 10,000 or 15,000 genomic regions in List 3. In one aspect, at least 1,000, 2,000 probes can be configured to be complementary to at least 500, 1,000, 5000, 10,000 or 15,000 genomic regions in List 5. In one aspect, at least 1,000, 2,000 probes can be configured to be complementary to at least 500, 1,000, 5000, 10,000 or 15,000 genomic regions in List 8.

In another aspect, provided herein is a method of designing a cancer assay panel comprising the steps of: identifying a plurality of genomic regions, wherein each of the plurality of genomic regions (i) comprises at least 30 nucleotides, and (ii) comprises at least five methylation sites, wherein the at least five methylation sites are either hypomethylated or hypermethylated, comparing methylation status of the at least five methylation sites in each of the plurality of genomic regions between cancerous samples and non-cancerous samples, selecting a subset of the genomic regions, wherein at least five methylation sites of the subset of the genomic regions have an abnormal methylation pattern in cancerous samples relative to non-cancerous samples, and designing a cancer assay panel comprising a plurality of probe sets, wherein each of the plurality of probe sets comprises at least a pair of probes configured to target one of the subset of the genomic regions. In one aspect, the abnormal methylation pattern matches that of a cfDNA fragment from the cancerous samples overlapping at least one of the at least five methylation sites, wherein the cfDNA has at least a threshold p-value rarity relative to a training data set of the non-cancerous samples. In one aspect, the method further comprises the step of selecting based on criteria comprising: (a) a number $N_{cancer}$ of the cancerous samples including cfDNA fragments having the abnormal methylation pattern; and (b) a number $N_{non-cancer}$ of the non-cancerous samples including cfDNA fragments having the abnormal methylation pattern. In one aspect, the step of selecting is based on criteria positively correlated to $N_{cancer}$ and inversely correlated to the sum of $N_{cancer}$ and $N_{non-cancer}$. Each of the plurality of probes can have less than 20, 15, 10 or 8 off-target genomic regions. In one aspect, the he less than 20, 15, 10, or 8 off-target genomic regions are identified using a k-mer seeding strategy. In one aspect, the less than 20, 15, 10 or 8 off-target genomic regions are identified using k-mer seeding strategy combined to local alignment at seed locations. The method can further comprise the step of making the cancer assay panel comprising the plurality of probes.

In another aspect, provided herein is a cancer assay panel comprising a plurality of probes made by the method described above. The subset of genomic regions in the cancer assay panel can comprise genomic regions of any one of Lists 1-8. The subset of genomic regions in the cancer assay panel can comprise genomic regions of List 3. The subset of genomic regions in the cancer assay panel can comprise genomic regions of List 5. The subset of genomic regions in the cancer assay panel can comprise genomic regions of List 8. The subset of the genomic regions in the cancer assay panel can comprise at least 20%, 30%, 40%, 50%, 60%, 70%, 80%, or 90% of the genomic regions in one or more of any one of Lists 1-8. The subset of the genomic regions in the cancer assay panel can comprise at least 20%, 30%, 40%, 50%, 60%, 70%, 80%, or 90% of the genomic regions in List 3. The subset of the genomic regions in the cancer assay panel can comprise at least 20%, 30%, 40%, 50%, 60%, 70%, 80%, or 90% of the genomic regions in List 5. The subset of the genomic regions in the cancer assay panel can comprise at least 20%, 30%, 40%, 50%, 60%, 70%, 80%, or 90% of the genomic regions in List 8. The subset of the genomic regions can comprise at least 500, 1,000, 5000, 10,000, 15,000, 20,000 or 25,000 genomic regions in any one of Lists 1-8. The subset of the genomic regions can comprise at least 500, 1,000, 5000, 10,000, 15,000, 20,000 or 25,000 genomic regions in List 3. The subset of the genomic regions can comprise at least 500, 1,000, 5000, 10,000, 15,000, 20,000 or 25,000 genomic regions in List 5. The subset of the genomic regions can comprise at least 500, 1,000, 5000, 10,000, 15,000, 20,000 or 25,000 genomic regions in List 8.

In another aspect, provided herein is a cancer assay panel comprising a plurality of probes, wherein each of the plurality of probes is configured to overlap with one of the genomic regions in any one of Lists 1-8, and the plurality of probes together overlap with at least 90%, 95% or 100% of the genomic regions in any one of Lists 1-8. In another aspect, provided herein is a cancer assay panel comprising a plurality of probes, wherein each of the plurality of probes is configured to overlap with one of the genomic regions in any one of Lists 1-8, and the plurality of probes together overlap with at least 500, 1,000, 5000, 10,000 or 15,000 genomic regions in any one of Lists 1-8.

The present description provides: a cancer assay panel comprising at least 500 pairs of probes, wherein each pair of the at least 500 pairs comprises two probes configured to overlap each other by an overlapping sequence, wherein the overlapping sequence comprises a 30-nucleotide fragment, the 30-nucleotide fragment comprises at least five CpG sites, wherein at least 80% of the at least five CpG sites comprise either CpG or at least 80% of the at least five CpG sites comprise UpG, and wherein the 30-nucleotide fragment is configured to bind to one or more genomic regions in cancerous samples, wherein the one or more genomic regions have at least five methylation sites, wherein the at least five methylation sites have an abnormal methylation pattern in non-cancerous samples or cancerous samples.

In some embodiments, the overlapping sequence comprises at least 40, 50, 75, or 100 nucleotides. In some embodiments, the cancer assay panel comprises at least 1,000, 2,000, 2,500, 5,000, 6,000, 7,500, 10,000, 15,000, 20,000 or 25,000 pairs of probes.

Another aspect of the present description provides a cancer assay panel, comprising: at least 1,000 probes, wherein each of the probes is designed as a hybridization probe complementary to one or more genomic regions, wherein each of the genomic regions comprises: (i) at least 30 nucleotides, and (ii) at least five methylation sites, wherein the at least five methylation sites have an abnormal methylation pattern and are either hypomethylated or hypermethylated in cancerous samples or non-cancerous samples.

In some embodiments, the abnormal methylation pattern has at least a threshold p-value rarity in the non-cancerous samples. In some embodiments, each of the probes is designed to be complementary to less than 20 off-target genomic regions.

In some embodiments, each of the genomic regions was selected based on criteria comprising: a number ($N_{cancer}$) of the cancerous samples including cfDNA fragments having the abnormal methylation pattern; and a number ($N_{non-cancer}$) of the non-cancerous samples including cfDNA fragments having the abnormal methylation pattern.

In some embodiments, each of the genomic regions was selected based on criteria positively correlated to $N_{cancer}$ and inversely correlated to the sum of $N_{cancer}$ and $N_{non-cancer}$.

In some embodiments, the cancer assay panel comprises at least 1,000, 2,000, 2,500, 5,000, 10,000, 12,000, 15,000, 20,000, 30,000, 40,000, 50,000, or 100,000 probes. In some embodiments, the at least 1,000 pairs of probes or the at least 2,000 probes together comprise at least 0.2 million, 0.4 million, 0.6 million, 0.8 million, 1 million, 2 million, 3 million, 4 million, 5 million, 6 million nucleotides, 7 million nucleotides, 8 million nucleotides, 9 million nucleotides, or 10 million nucleotides. In some embodiments, each of the probes comprises at least 50, 75, 100, or 120 nucleotides. In some embodiments, each of the probes comprises less than 300, 250, 200, or 150 nucleotides. In some embodiments, each of the probes comprises 100-150 nucleotides. In some embodiments, each of the probes comprises less than 20, 15, 10, 8, or 6 methylation sites. In some embodiments, at least 80%, 85%, 90%, 92%, 95%, or 98% of the at least five methylation sites are either methylated or unmethylated in the cancerous samples. In some embodiments, each of the probes is configured to be complementary to less than 20, 15, 10 or 8 off-target genomic regions.

In some embodiments, at least 15%, 20%, 30%, or 40% of the genomic regions are in exons or introns. In some embodiments, at least 5%, 10%, 15%, 20%, 30% or 40% of the genomic regions are in exons. In some embodiments, less than 5%, 10%, 15%, 20%, 25%, or 30% of the genomic regions are in intergenic regions. In some embodiments, between 20% and 60%, between 30% and 50%, or between 35% and 55% of the genomic regions are in introns or exons. In some embodiments, between 5% and 30% between 10% and 25%, or between 12% and 20% of the genomic regions are in exons. In some embodiments, between 5% and 20% of the genomic regions are in intergenic regions.

In some embodiments, the genomic regions are selected from any one of Lists 1-8. In some embodiments, the genomic regions comprise at least 20%, 30%, 40%, 50%, 60%, 70%, 80%, 90% or 95% of the genomic regions in any one of Lists 1-8. In some embodiments, the at least 1,000 probes are configured to be complementary to at least 500, 1,000, 5000, 10,000 or 15,000 genomic regions in any one of Lists 1-8.

In another aspect, the present description provides a cancer assay method comprising receiving a sample comprising a plurality of nucleic acid fragments; treating the plurality of nucleic acid fragments to convert unmethylated cytosine to uracil, thereby obtaining a plurality of converted nucleic acid fragments; hybridizing the plurality of converted nucleic acid fragments with the probes on the cancer assay panel of any of the above claims; enriching a subset of the converted nucleic acid fragments; and sequencing the enriched subset of the converted nucleic acid fragments, thereby providing a set of sequence reads.

In some embodiment, the method further comprises the step of determining a health condition by evaluating the set of sequence reads, wherein the health condition is a presence or absence of cancer and/or, cancer stage.

In some embodiments, the set of nucleic acid fragments is obtained from a human subject.

In other aspect, the present description provides a method of diagnosing cancer, comprising the steps of: (a) obtaining a set of sequence reads by sequencing a set of nucleic acid fragments from a subject; (b) determining methylation status of a plurality of genomic regions, the plurality of genomic regions comprise genomic regions of any one of Lists 1-8; and (c) determining a health condition of the subject by evaluating the methylation status, wherein the health condition is (i) a presence or absence of cancer; or (ii) a stage of cancer. In other aspect, the present description provides a method for diagnosing cancer, comprising the steps of: (a) obtaining a set of sequence reads by sequencing a set of nucleic acid fragments from a subject; (b) determining methylation status of a plurality of genomic regions, the plurality of genomic regions comprise at least 20%, 30%, 40%, 50%, 60%, 70%, 80%, 90% or 95% of the genomic regions in any one of Lists 1-8; and (c) determining a health condition of the subject by evaluating the methylation status, wherein the health condition is (i) a presence or absence of cancer; or (ii) a stage of cancer. In other aspects, the present description provides a method for diagnosing cancer, comprising the steps of: (a) obtaining a set of sequence reads by sequencing a set of nucleic acid fragments from a subject; (b) determining methylation status of a plurality of at least 1,000, 2,000, 2,500, 5,000, 6,000, 7,500, 10,000, 15,000, 20,000 or 25,000 genomic regions among genomic regions in any one of Lists 1-8; and (c) determining a health condition of the subject by evaluating the methylation status, wherein the health condition is (i) a presence or absence of cancer; or (ii) a stage of cancer.

Yet another aspect provides a method of designing a cancer assay panel comprising the steps of: identifying a plurality of genomic regions, wherein each of the plurality of genomic regions (i) comprises at least 30 nucleotides, and (ii) comprises at least five methylation sites, comparing methylation status of the at least five methylation sites in each of the plurality of genomic regions between cancerous samples and non-cancerous samples, wherein the at least five methylation sites are either hypomethylated or hypermethylated, selecting a subset of the genomic regions, wherein at least five methylation sites of the subset of the genomic regions have an abnormal methylation pattern in cancerous samples relative to non-cancerous samples, and designing a cancer assay panel comprising a plurality of probe sets, wherein each of the plurality of probe sets comprises at least a pair of probes configured to target (e.g., to be complementary to either converted or non-converted fragments corresponding to) one of the subset of the genomic regions.

In some embodiments, the abnormal methylation pattern matches that of a cfDNA fragment from the cancerous samples overlapping at least one of the at least five methylation sites, wherein the cfDNA has at least a threshold p-value rarity relative to a training data set of the non-cancerous samples.

In some embodiments, the step of selecting is performed based on criteria comprising: a number $N_{cancer}$ of the cancerous samples including cfDNA fragments having the abnormal methylation pattern; and a number $N_{non-cancer}$ of the non-cancerous samples including cfDNA fragments having the abnormal methylation pattern. In some embodiments, the step of selecting is based on criteria positively correlated to $N_{cancer}$ and inversely correlated to the sum of $N_{cancer}$ and $N_{non-cancer}$.

In some embodiments, each of the plurality of probes has less than 20, 15, 10 or 8 off-target genomic regions. In some embodiments, the method further comprises the step of: making the cancer assay panel comprising the plurality of probes.

Another aspect of the present description provides a cancer assay panel made by the method provided herein. In some embodiments, the subset of genomic regions comprises genomic regions of any one of Lists 1-8. In some embodiments, the subset of the genomic regions comprises at least 20%, 30%, 40%, 50%, 60%, 70%, 80%, or 90% of the genomic regions in any one of Lists 1-8. In some embodiments, the subset of the genomic regions comprises at least 500, 1,000, 5000, 10,000 or 15,000 genomic regions in any one of Lists 1-8.

Another aspect of the present description provides a cancer assay panel comprising a plurality of probes, wherein each of the plurality of probes is configured to overlap with one of the genomic regions in any one of Lists 1-8, and the plurality of probes together overlap with at least 90%, 95% or 100% of the genomic regions in any one of Lists 1-8. In yet another aspect, the present description provides a cancer assay panel comprising a plurality of probes, wherein each of the plurality of probes is configured to overlap with one of the genomic regions in any one of Lists 1-8, and the plurality of probes together overlap with at least 500, 1,000, 5000, 10,000 or 15,000 genomic regions in any one of Lists 1-8.

5. BRIEF DESCRIPTION OF THE DRAWINGS

Figure 8A:
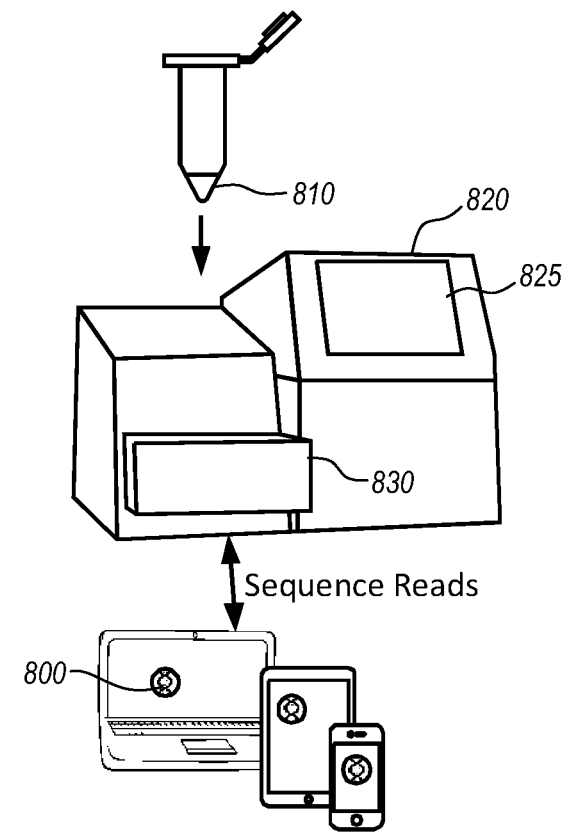
FIG. 8A is a flowchart of devices for sequencing nucleic acid samples according to one embodiment.
Figure 8B:
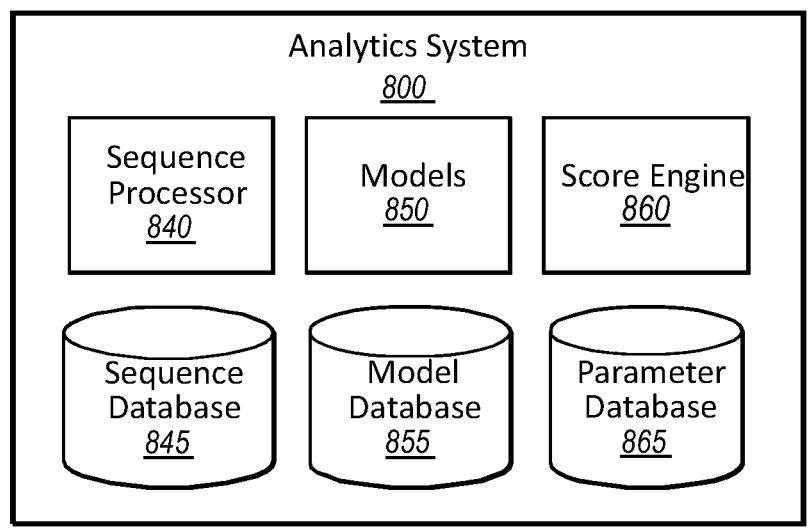

FIG. 8B provides an analytic system that analyzes methylation status of cfDNA according to one embodiment.

Figure 9A:
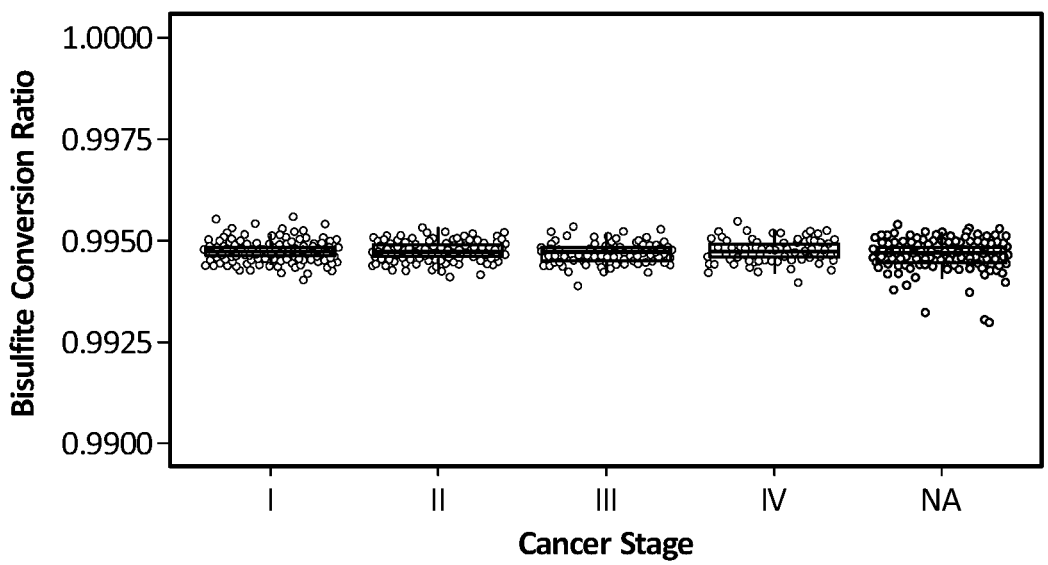
Figure 9B:
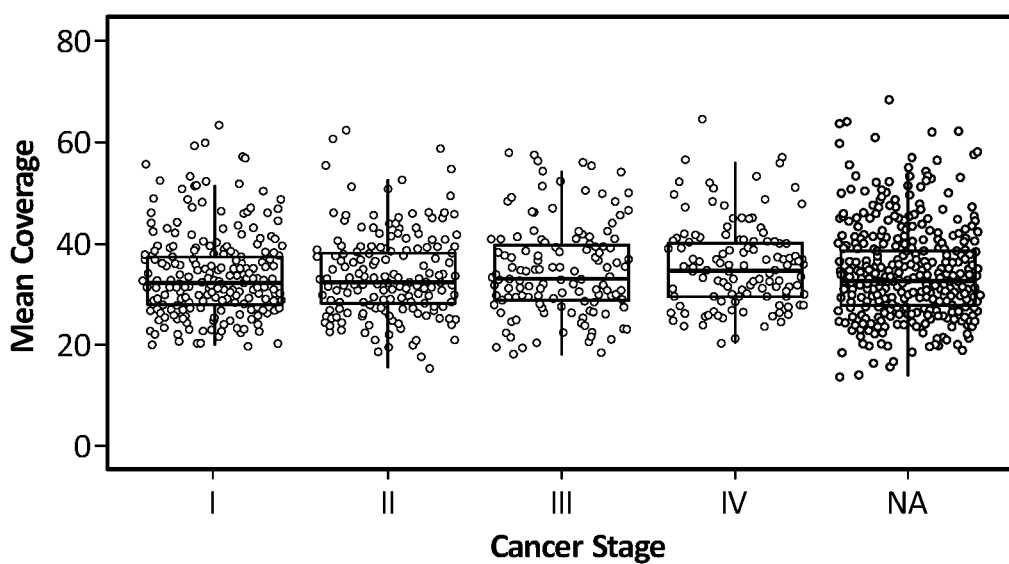
Figure 9C:
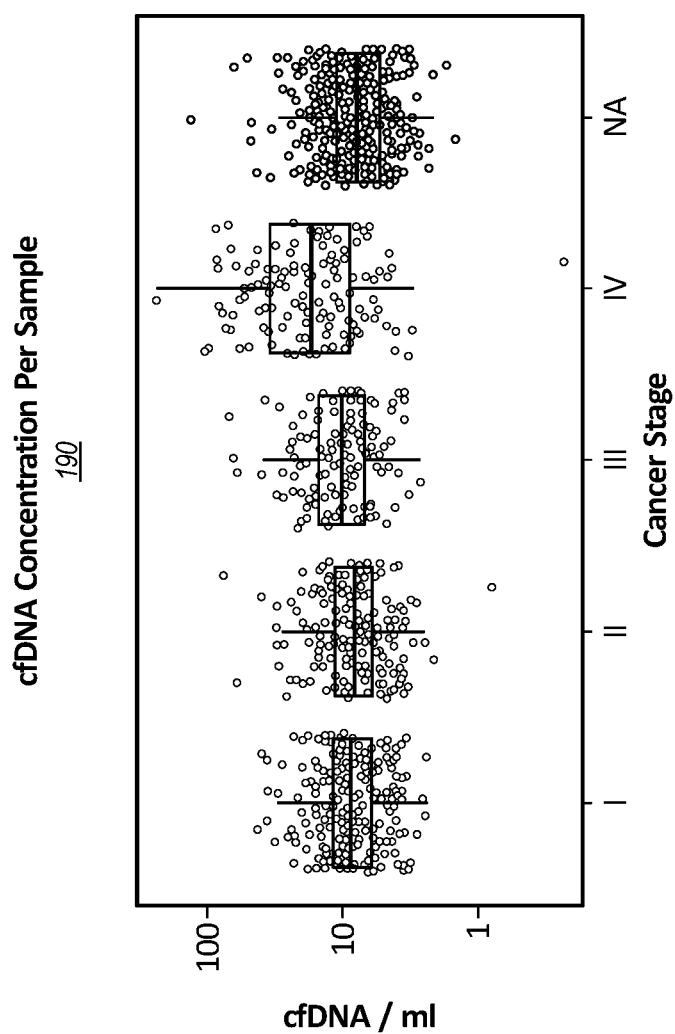

FIG. 9A (Conversion Accuracy), FIG. 9B (Sequencing Depth), and FIG. 9C (cfDNA Concentration Per Sample) show graphs of data validating the consistency of sequencing from a control group.

Figure 10:
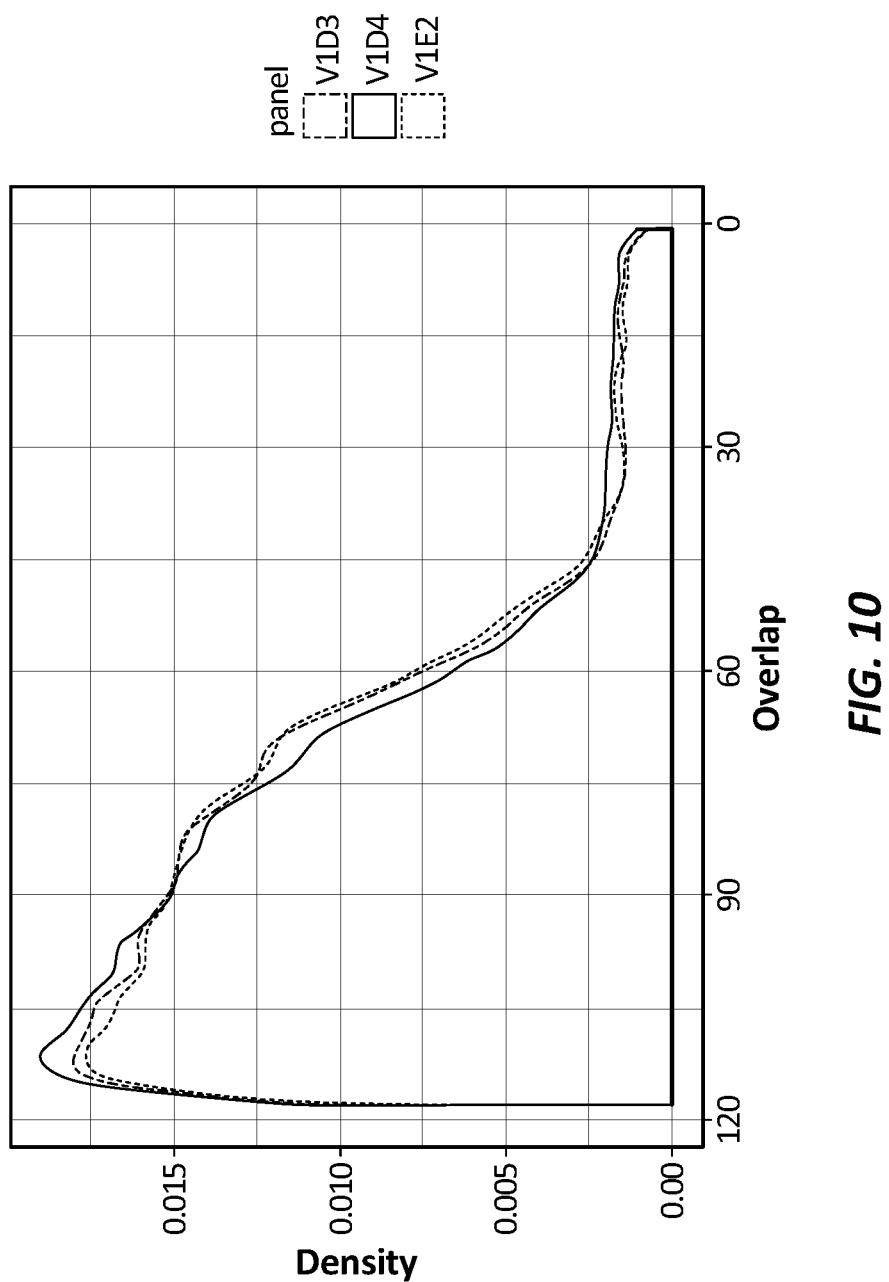

FIG. 10 is a graph of the amounts of DNA fragments binding to probes depending on the sizes of overlaps between the DNA fragments and the probes.

Figure 11:
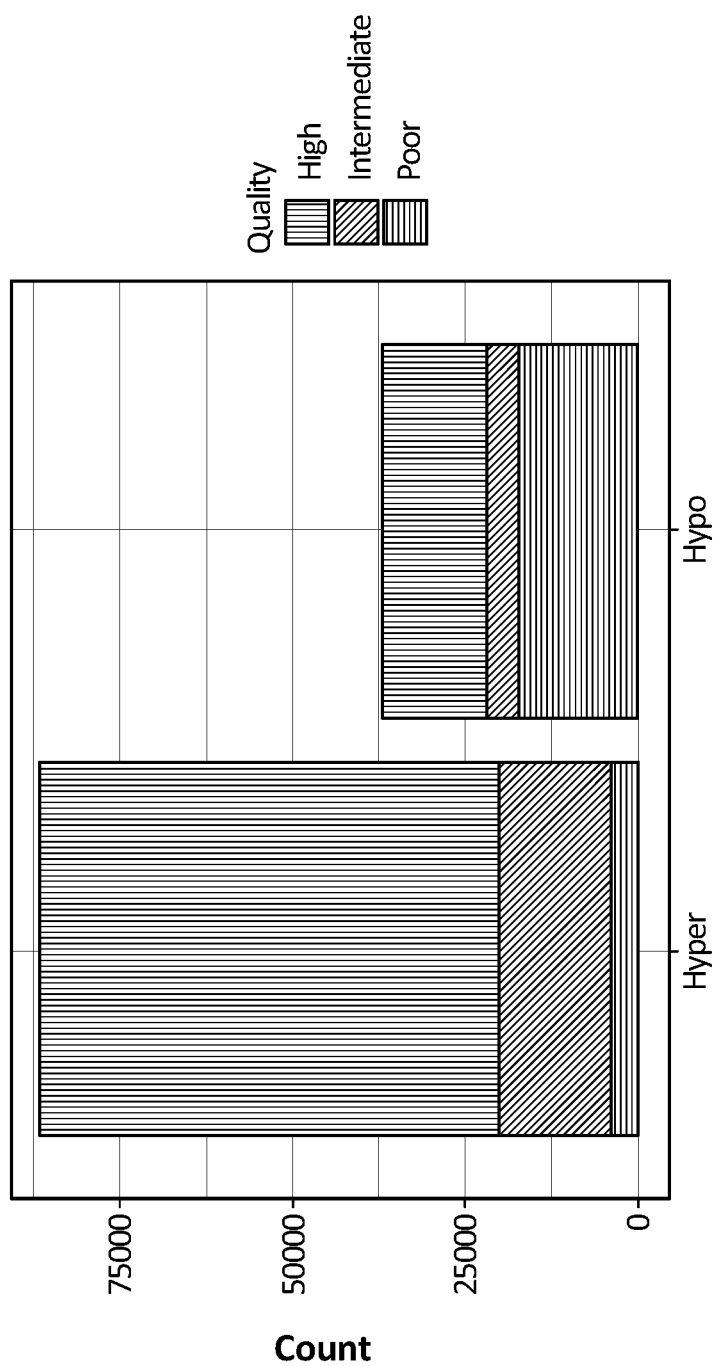

FIG. 11 compares the numbers of high quality, intermediate quality, and poor quality probes among the probes targeting hypermethylated fragments (Hyper) or hypomethylated fragments (Hypo).

Figure 12B:
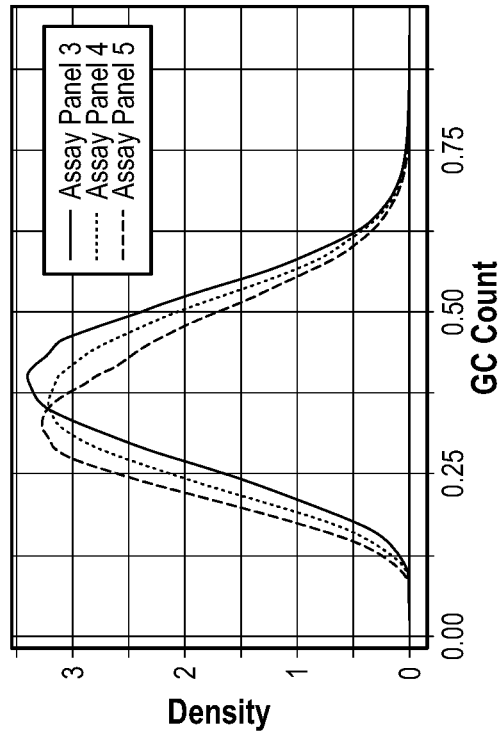
Figure 12A:
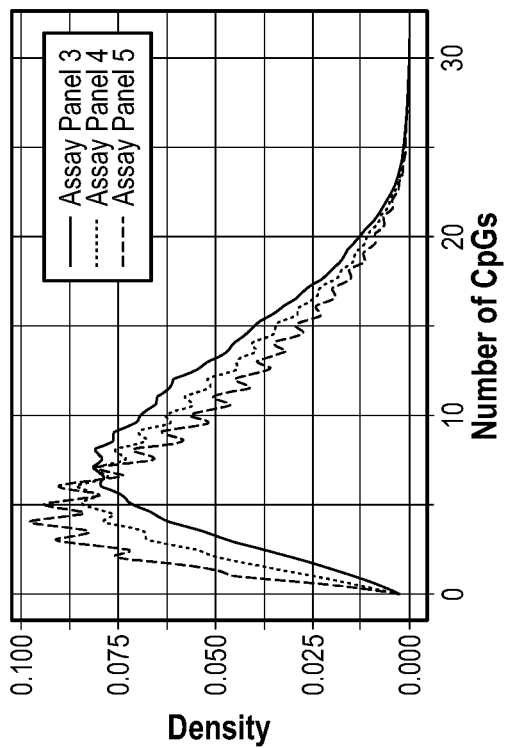

FIG. 12A shows the number, for various assay panels, the number of CpGs as a function of density.

FIG. 12B shows, for various assay panels, the G/C fraction as a function of density.

FIG. 13A (Assay Panel 3), FIG. 13B (Assay Panel 4) and FIG. 13C (Assay Panel 5) summarize frequencies of genomic annotations of targeted genomic regions (black) and randomly selected regions (white) in the indicated Assay Panels.

Figures 14A, 14B:
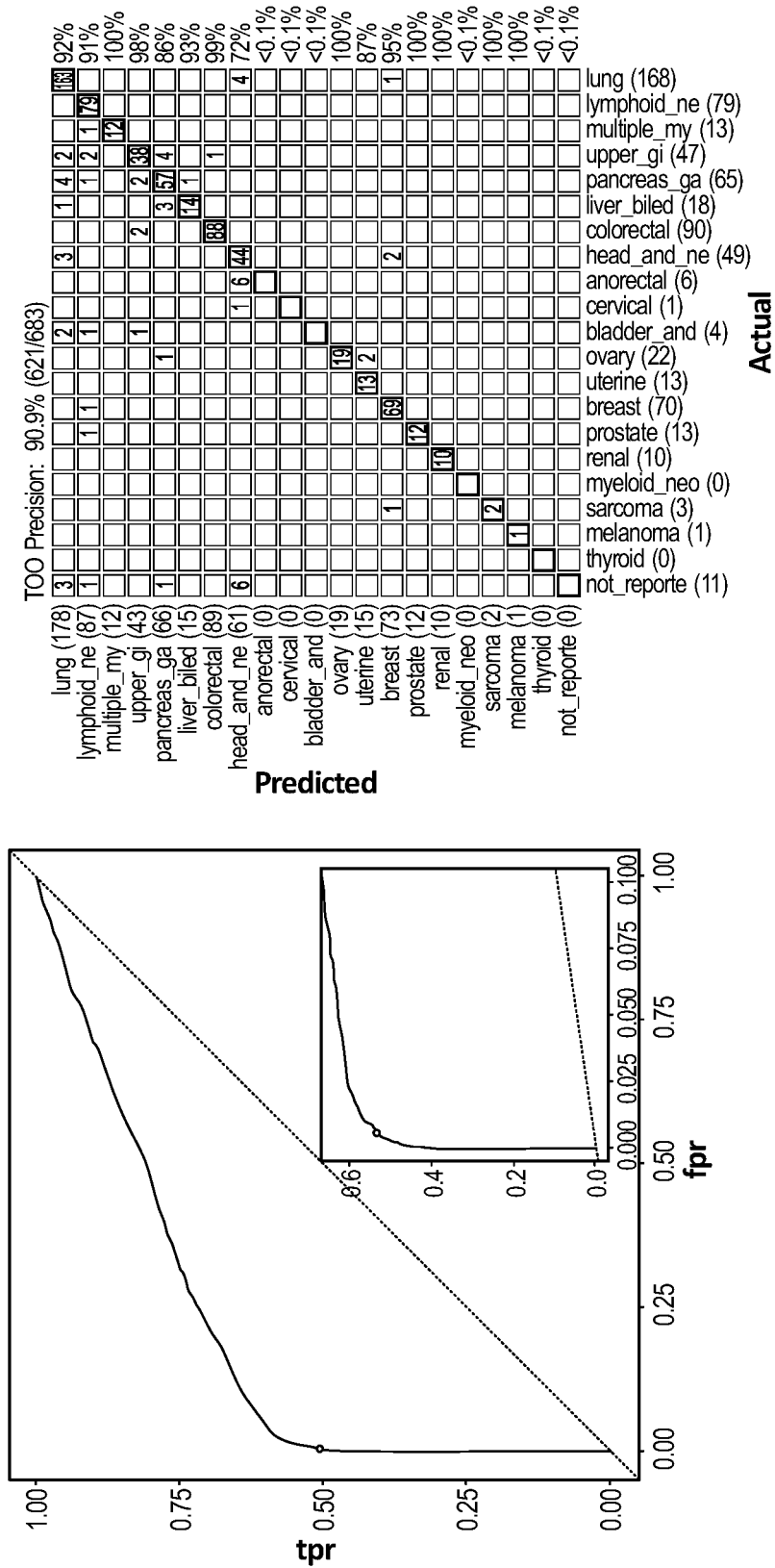

FIG. 14A depicts a receiver operator curve (ROC) showing the sensitivity and specificity of cancer detection using Assay Panel 1.

FIG. 14B is a confusion matrix depicting the accuracy of tissue of origin (TOO) classifications using Assay Panel 1.

Figures 15A, 15B:
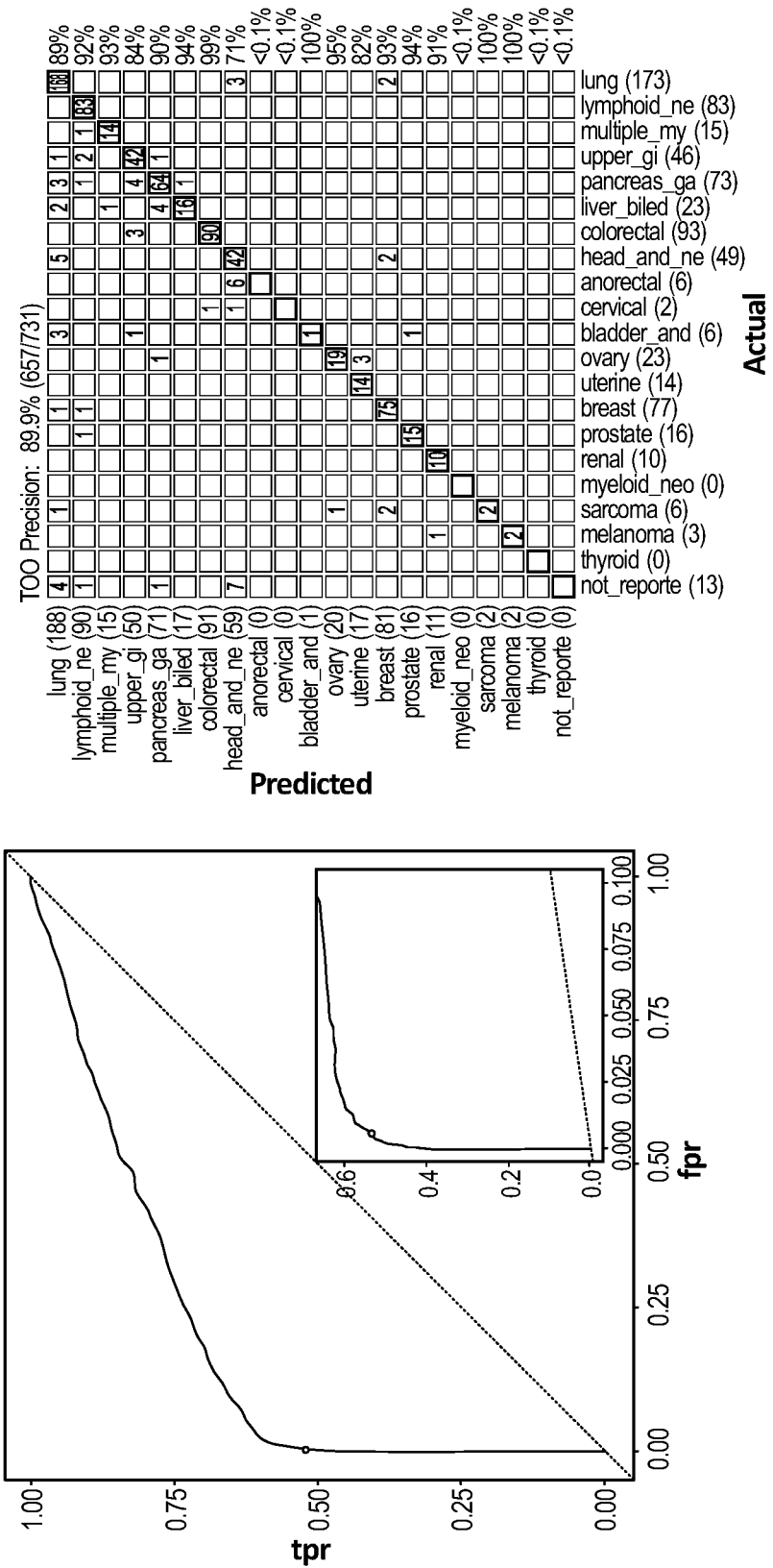

FIG. 15A depicts a receiver operator curve (ROC) showing the sensitivity and specificity of cancer detection using Assay Panel 2.

FIG. 15B is a confusion matrix depicting the accuracy of tissue of origin (TOO) classifications using Assay Panel 2.

Figures 16A, 16B:
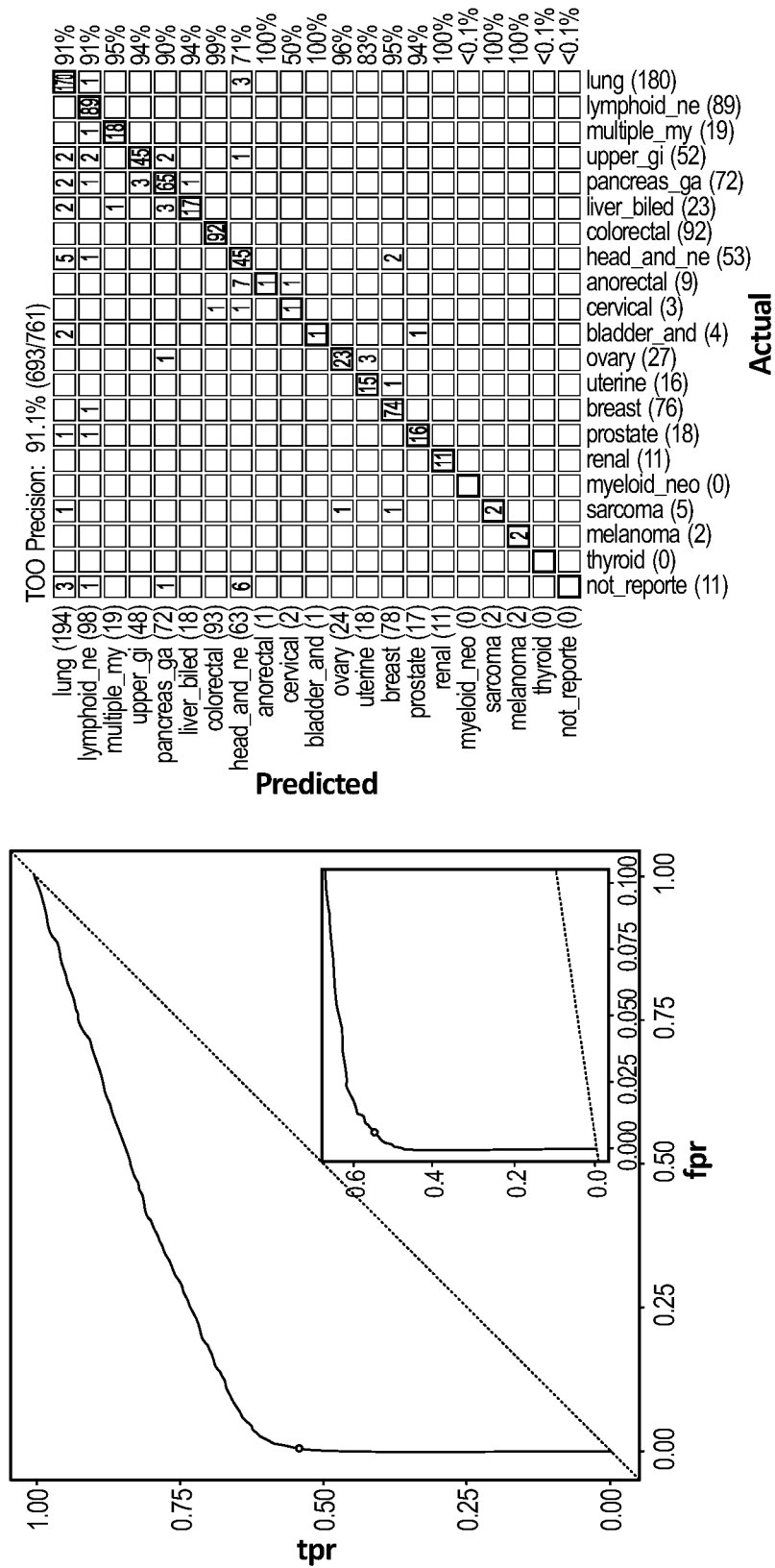

FIG. 16A depicts a receiver operator curve (ROC) showing the sensitivity and specificity of cancer detection using Assay Panel 3.

FIG. 16B is a confusion matrix depicting the accuracy of tissue of origin (TOO) classifications using Assay Panel 3.

Figures 17A, 17B:
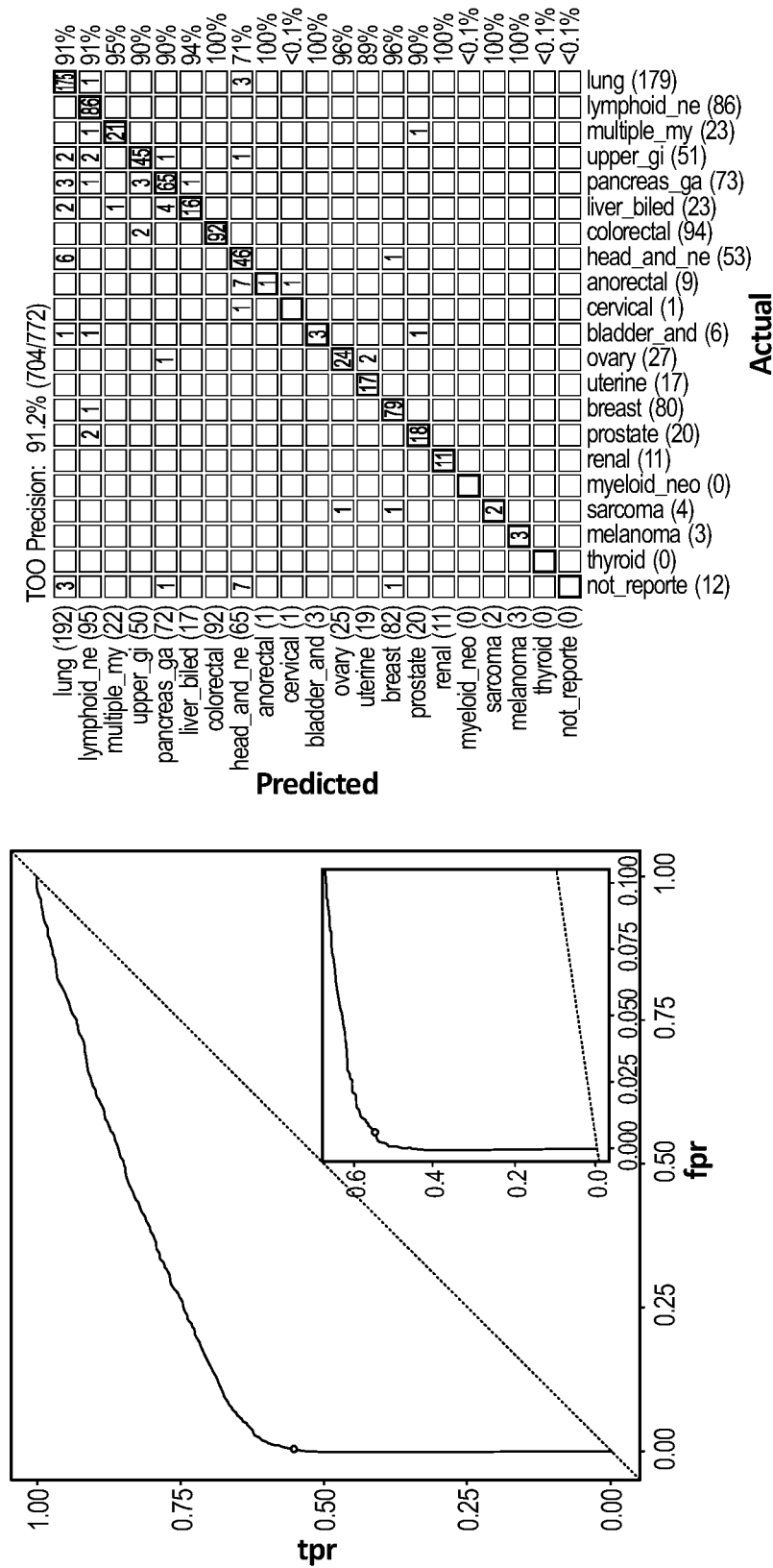

FIG. 17A depicts a receiver operator curve (ROC) showing the sensitivity and specificity of cancer detection using Assay Panel 4.

FIG. 17B is a confusion matrix depicting the accuracy of tissue of origin (TOO) classifications using Assay Panel 4.

Figures 18A, 18B:
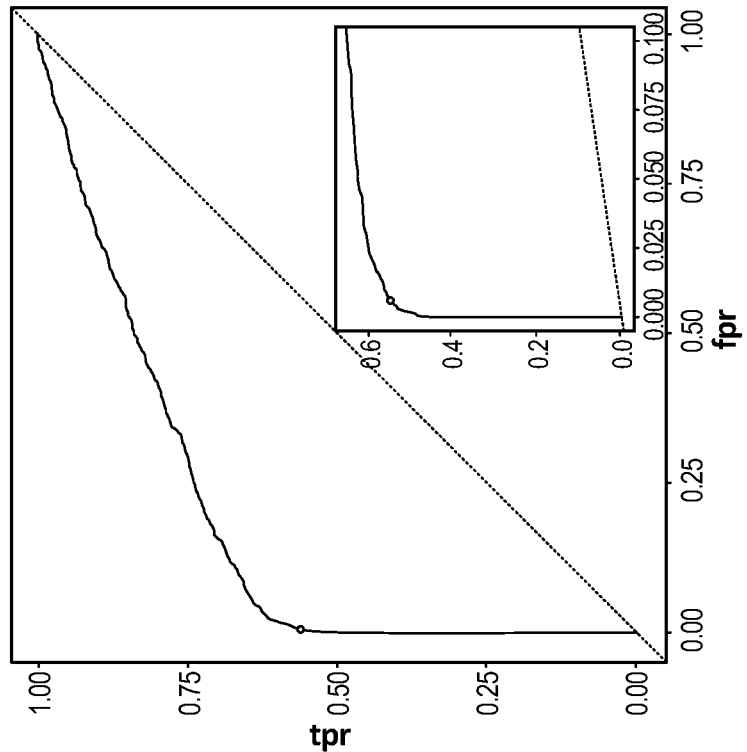

FIG. 18A depicts a receiver operator curve (ROC) showing the sensitivity and specificity of cancer detection using Assay Panel 5.

FIG. 18B is a confusion matrix depicting the accuracy of tissue of origin (TOO) classifications using Assay Panel 5.

FIG. 19A depicts a receiver operator curve (ROC) showing the sensitivity and specificity of cancer detection using Assay Panel 6.

FIG. 19B is a confusion matrix depicting the accuracy of tissue of origin (TOO) classifications using Assay Panel 6.

Figures 20A, 20B:
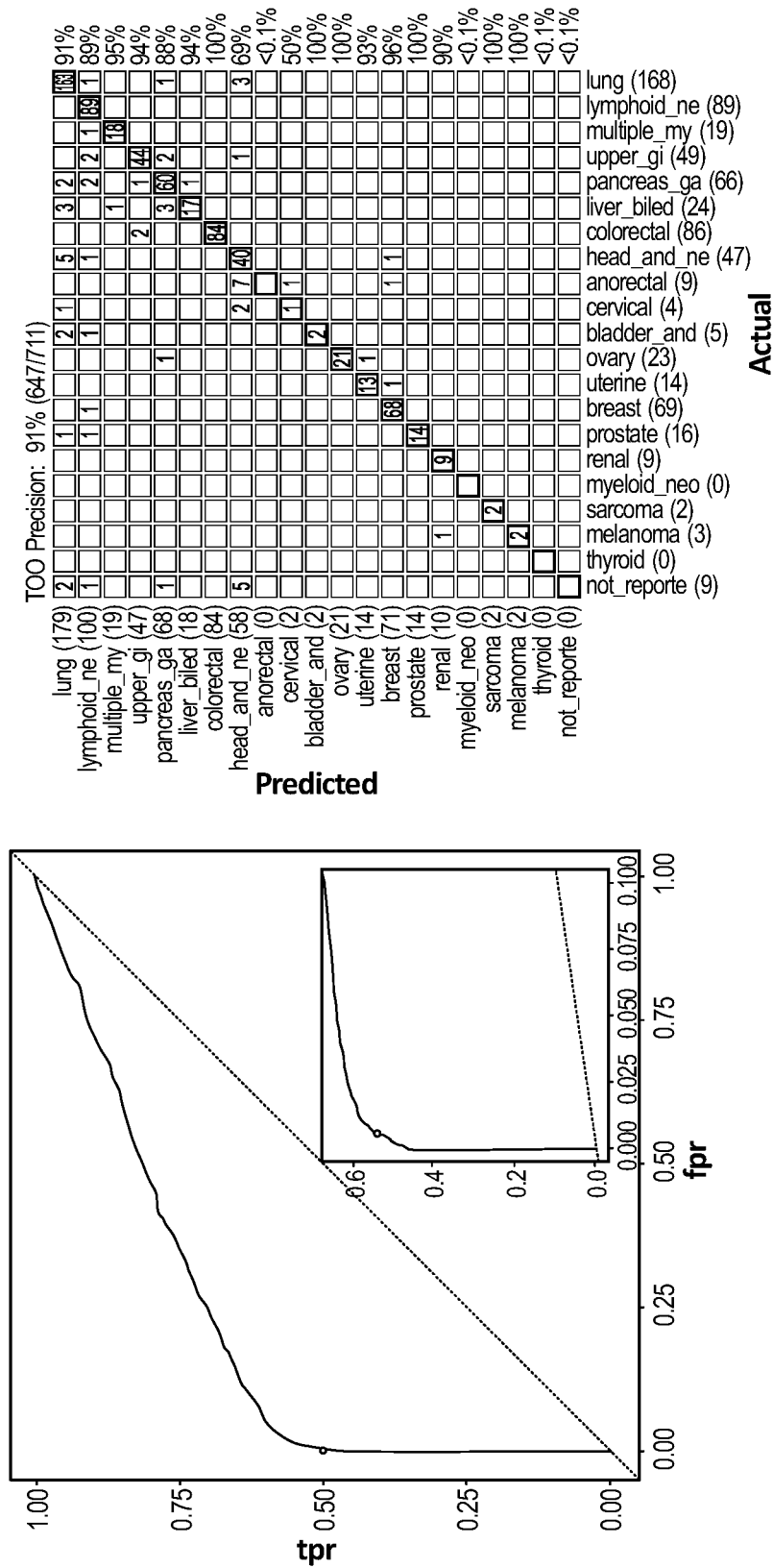

FIG. 20A depicts a receiver operator curve (ROC) showing the sensitivity and specificity of cancer detection using Assay Panel 3A.

FIG. 20B is a confusion matrix depicting the accuracy of tissue of origin (TOO) classifications using Assay Panel 3A.

Figures 21A, 21B:
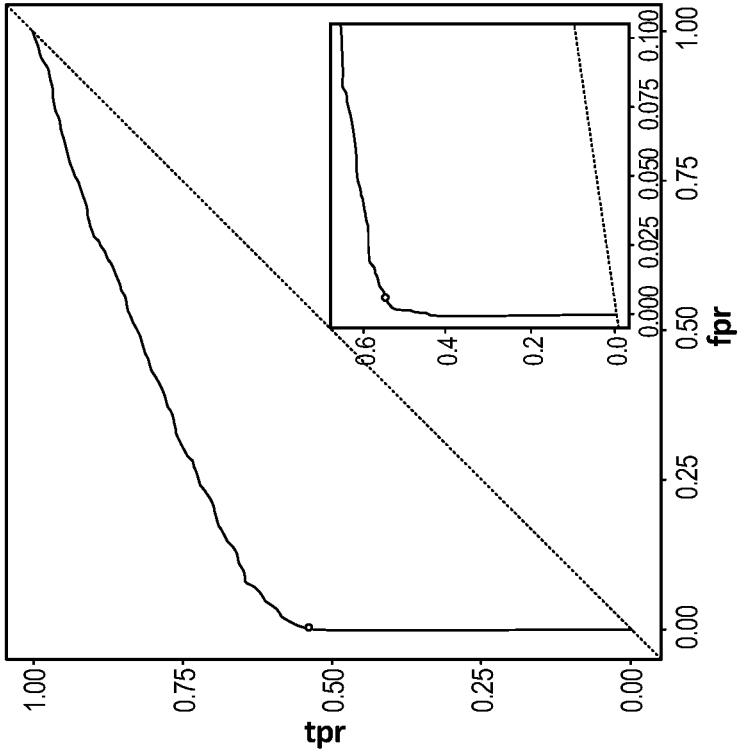

FIG. 21A depicts a receiver operator curve (ROC) showing the sensitivity and specificity of cancer detection using Assay Panel 4A.

FIG. 21B is a confusion matrix depicting the accuracy of tissue of origin (TOO) classifications using Assay Panel 4A.

Figures 22A, 22B:
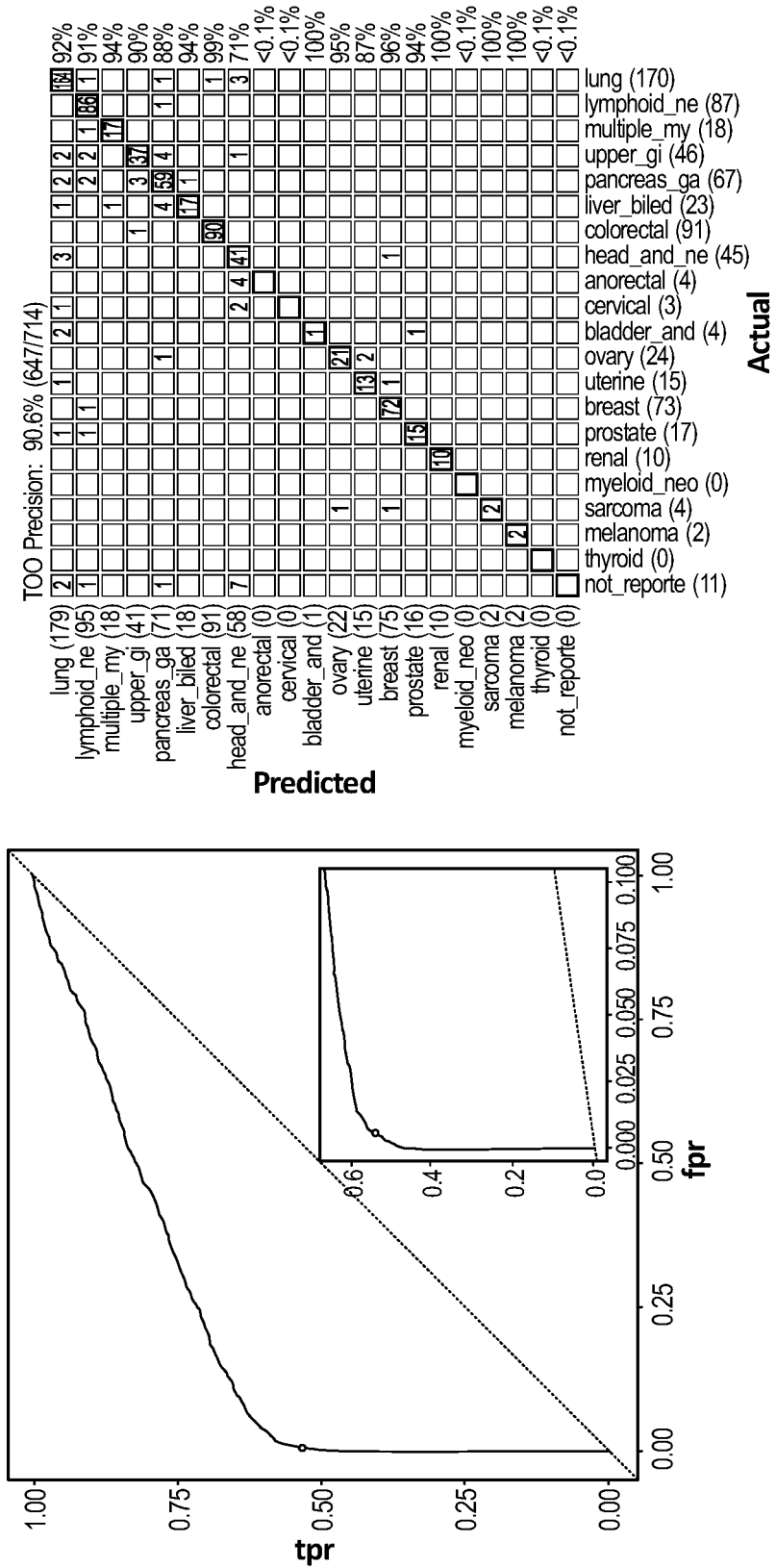

FIG. 22A depicts a receiver operator curve (ROC) showing the sensitivity and specificity of cancer detection using a random selection (subset a) of 40% of the targeted genomic regions in Assay Panel 3.

FIG. 22B is a confusion matrix depicting the accuracy of tissue of origin (TOO) classifications using a random selection (subset a) of 40% of the targeted genomic regions in Assay Panel 3.

Figures 23A, 23B:
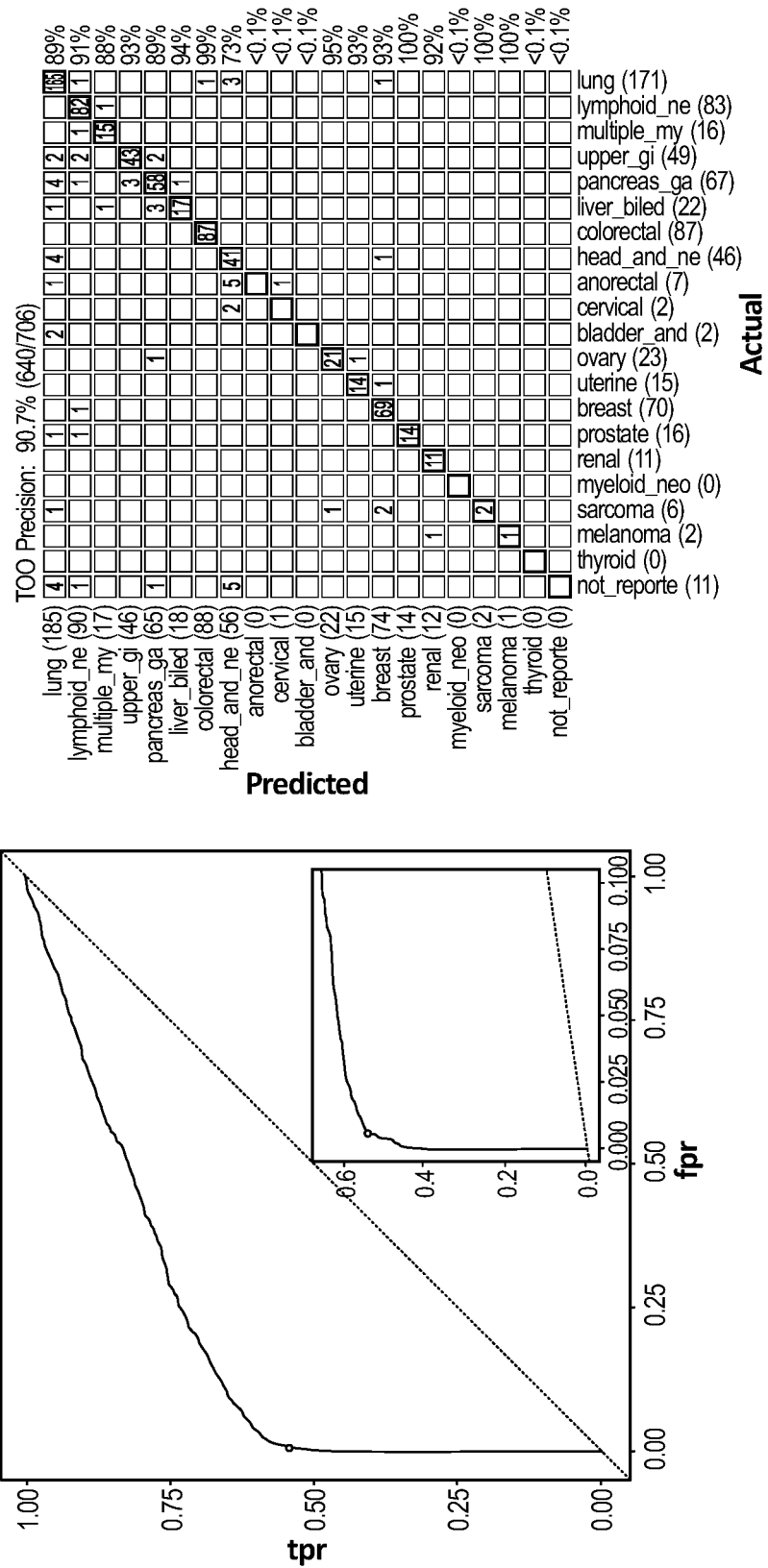

FIG. 23A depicts a receiver operator curve (ROC) showing the sensitivity and specificity of cancer detection using a random selection (subset b) of 40% of the targeted genomic regions in Assay Panel 3.

FIG. 23B is a confusion matrix depicting the accuracy of tissue of origin (TOO) classifications using a random selection (subset b) of 40% of the targeted genomic regions in Assay Panel 3.

Figures 24A, 24B:
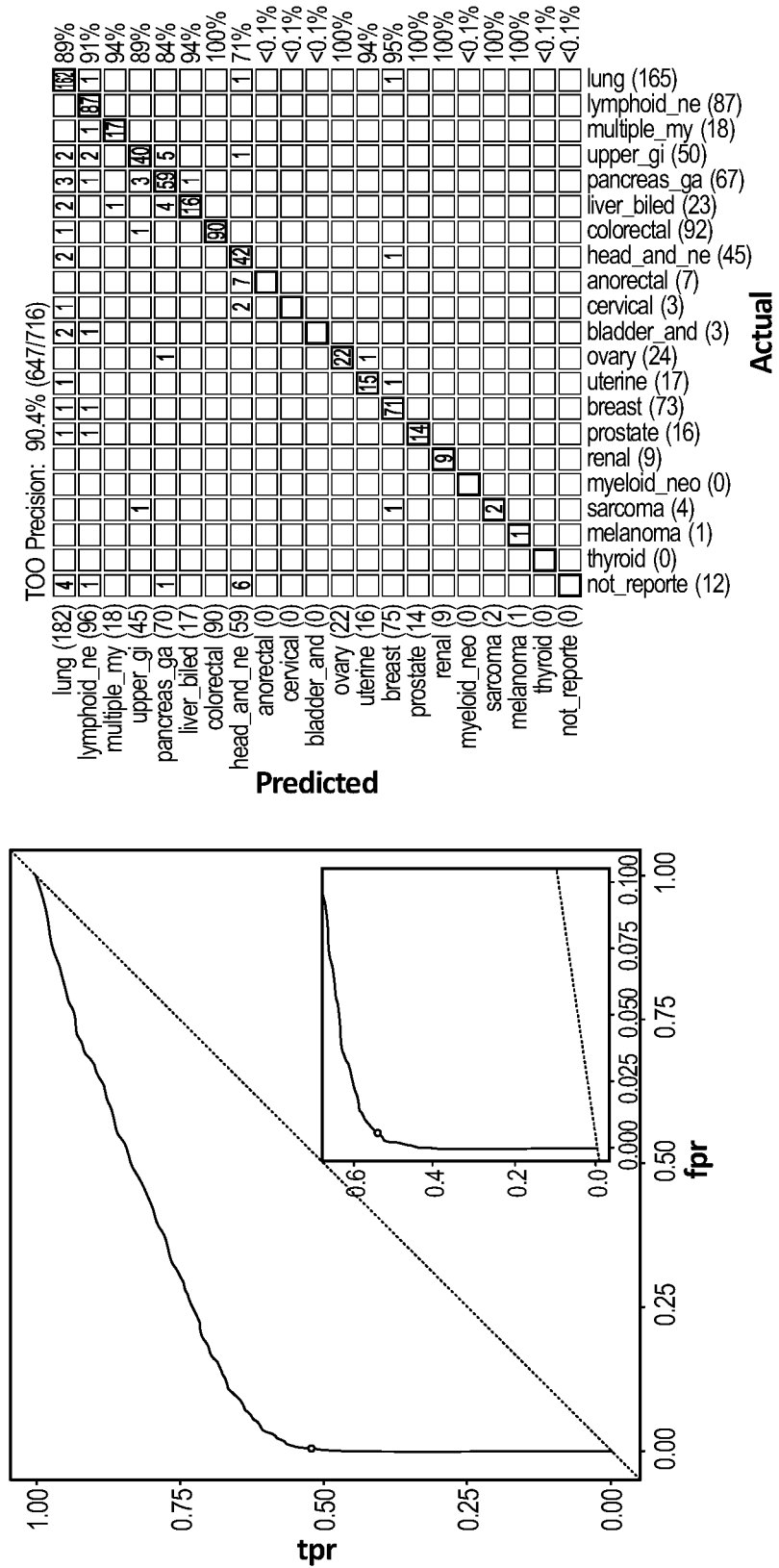

FIG. 24A depicts a receiver operator curve (ROC) showing the sensitivity and specificity of cancer detection using a random selection (subset c) of 40% of the targeted genomic regions in Assay Panel 3.

FIG. 24B is a confusion matrix depicting the accuracy of tissue of origin (TOO) classifications using a random selection (subset c) of 40% of the targeted genomic regions in Assay Panel 3.

Figures 25A, 25B:
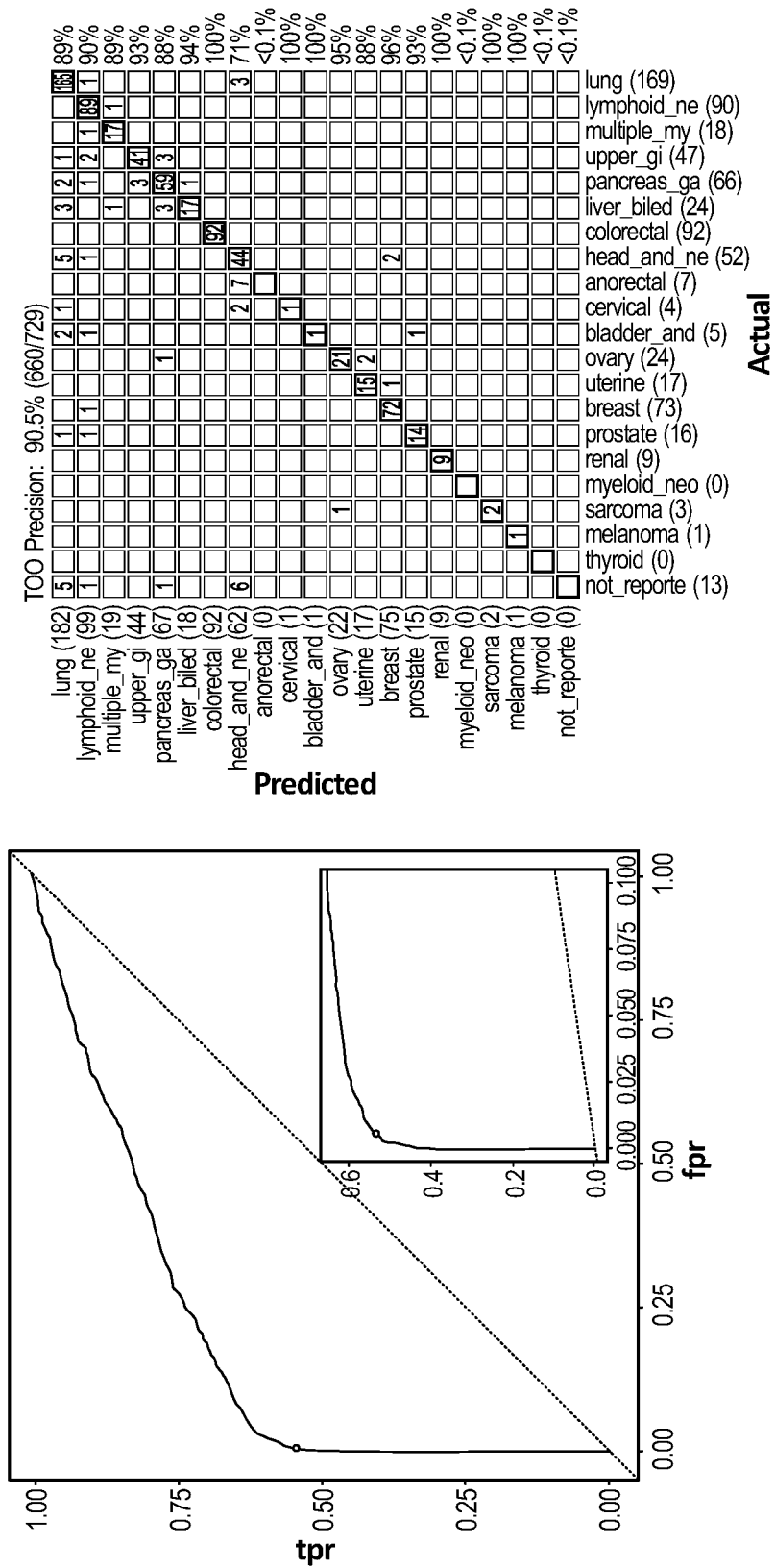

FIG. 25A depicts a receiver operator curve (ROC) showing the sensitivity and specificity of cancer detection using a random selection of 60% of the targeted genomic regions in Assay Panel 3.

FIG. 25B is a confusion matrix depicting the accuracy of tissue of origin (TOO) classifications using a random selection of 60% of the targeted genomic regions in Assay Panel 3.

Figures 26A, 26B:
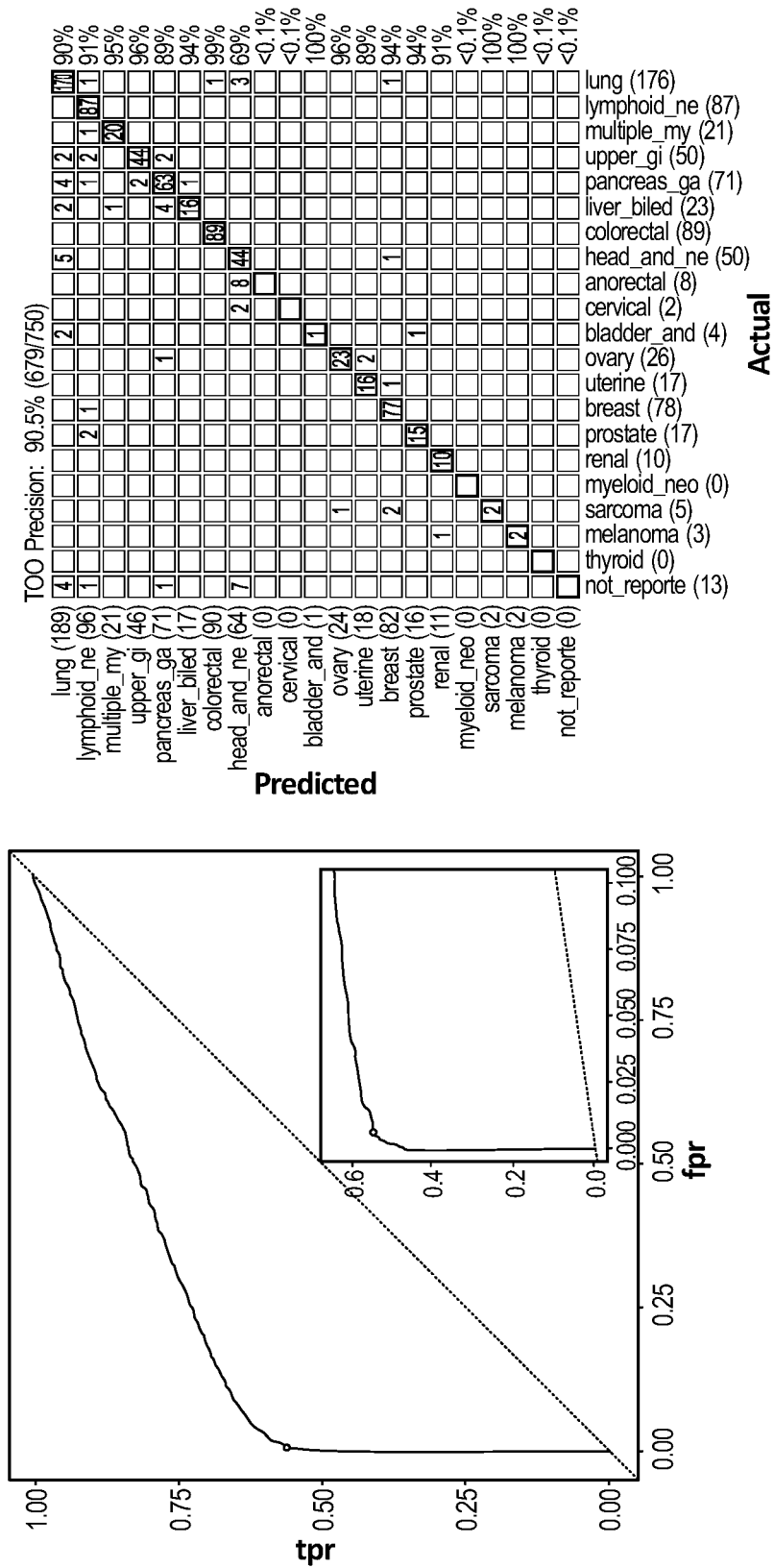

FIG. 26A depicts a receiver operator curve (ROC) showing the sensitivity and specificity of cancer detection using a random selection of 50% of the targeted genomic regions in Assay Panel 4.

FIG. 26B is a confusion matrix depicting the accuracy of tissue of origin (TOO) classifications using a random selection of 50% of the targeted genomic regions in Assay Panel 4.

Figures 27A, 27B:
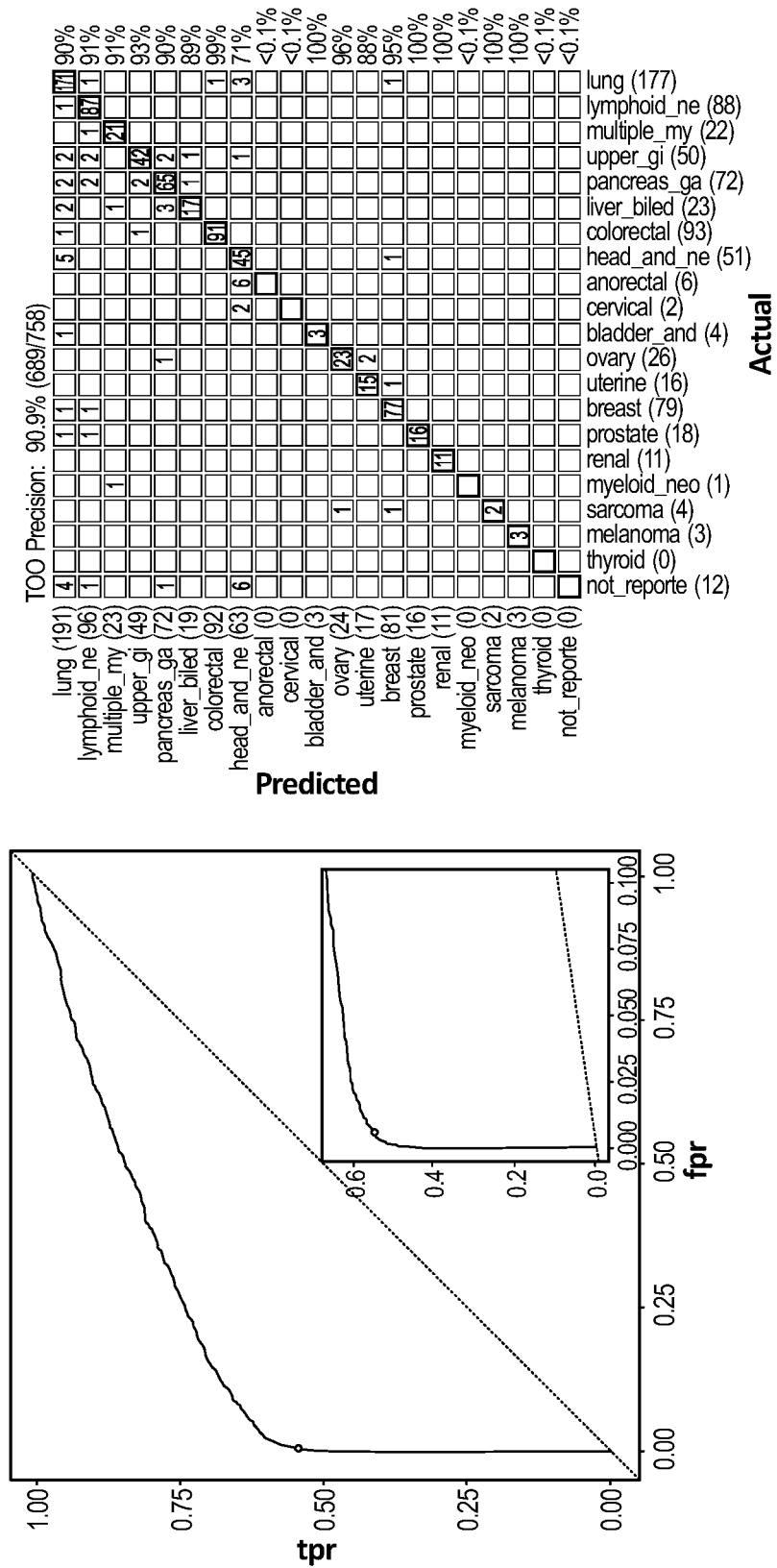

FIG. 27A depicts a receiver operator curve (ROC) showing the sensitivity and specificity of cancer detection using a random selection of 50% of the targeted genomic regions in Assay Panel 5.

FIG. 27B is a confusion matrix depicting the accuracy of tissue of origin (TOO) classifications using a random selection of 50% of the targeted genomic regions in Assay Panel 5.

The figures depict various embodiments of the present description for purposes of illustration only. One skilled in the art will readily recognize from the following discussion that alternative embodiments of the structures and methods illustrated herein may be employed without departing from the principles of the description described herein.

6. DETAILED DESCRIPTION

6.1. Definitions

Unless defined otherwise, all technical and scientific terms used herein have the meaning commonly understood by a person skilled in the art to which this description belongs. As used herein, the following terms have the meanings ascribed to them below.

The term "methylation" as used herein refers to a process by which a methyl group is added to a DNA molecule. For example, a hydrogen atom on the pyrimidine ring of a cytosine base can be converted to a methyl group, forming 5-methylcytosine. The term also refers to a process by which a hydroxymethyl group is added to a DNA molecules, for example by oxidation of a methyl group on the pyrimidine ring of a cytosine base. Methylation and hydroxymethylation tend to occur at dinucleotides of cytosine and guanine referred to herein as "CpG sites.

In such embodiments, the wet laboratory assay used to detect methylation may vary from those described herein as is well known in the art.

The term "methylation site" as used herein refers to a region of a DNA molecule where a methyl group can be added. "CpG" sites are the most common methylation site, but methylation sites are not limited to CpG sites. For example, DNA methylation may occur in cytosines in CHG and CHH, where H is adenine, cytosine or thymine. Cytosine methylation in the form of 5-hydroxymethylcytosine may also assessed (see, e.g., WO 2010/037001 and WO 2011/127136, which are incorporated herein by reference), and features thereof, using the methods and procedures disclosed herein.

The term "CpG site" as used herein refers to a region of a DNA molecule where a cytosine nucleotide is followed by a guanine nucleotide in the linear sequence of bases along its 5' to 3' direction. "CpG" is a shorthand for 5'-C-phosphate-G-3' that is cytosine and guanine separated by only one phosphate group. Cytosines in CpG dinucleotides can be methylated to form 5-methylcytosine.

The term "CpG detection site" as used herein refers to a region in a probe that is configured to hybridize to a CpG site of a target DNA molecule. The CpG site on the target DNA molecule can comprise cytosine and guanine separated by one phosphate group, where cytosine is methylated or unmethylated. The CpG site on the target DNA molecule can comprise uracil and guanine separated by one phosphate group, where the uracil is generated by the conversion of unmethylated cytosine.

The term "UpG" is a shorthand for 5'-U-phosphate-G-3' that is uracil and guanine separated by only one phosphate group. UpG can be generated by a bisulfite treatment of a DNA that converts unmethylated cytosines to uracils. Cytosines can be converted to uracils by other methods known in the art, such as chemical modification, synthesis, or enzymatic conversion.

The term "hypomethylated" or "hypermethylated" as used herein refers to a methylation status of a DNA molecule containing multiple CpG sites (e.g., more than 3, 4, 5, 6, 7, 8, 9, 10, etc.) where a high percentage of the CpG sites (e.g., more than 80%, 85%, 90%, or 95%, or any other percentage within the range of 50%-100%) are unmethylated or methylated, respectively.

The terms "methylation state vector" or "methylation status vector" as used herein refers to a vector comprising multiple elements, where each element indicates the methylation status of a methylation site in a DNA molecule comprising multiple methylation sites, in the order they appear from 5' to 3' in the DNA molecule. For example, $<M_x, M_{x+1}, M_{x+2}>$, $<M_x, M_{x+1}, U_{x+2}>$, ..., $<U_x, U_{x+1}, U_{x+2}>$ can be methylation vectors for DNA molecules comprising three methylation sites, where M represents a methylated methylation site and U represents an unmethylated methylation site.

The term "abnormal methylation pattern" or "anomalous methylation pattern" as used herein refers to the methylation pattern of a DNA molecule or a methylation state vector that is expected to be found in a sample less frequently than a threshold value. In a particular embodiment provided herein, the expectedness of finding a specific methylation state vector in a healthy control group comprising healthy individuals (e.g. individuals who have not been diagnosed with cancer) is represented by a p-value. A low p-value score generally corresponds to a methylation state vector which is relatively unexpected in comparison to other methylation state vectors within samples from healthy individuals. A high p-value score generally corresponds to a methylation state vector which is relatively more expected in comparison to other methylation state vectors found in samples from healthy individuals in the healthy control group. A methylation state vector having a p-value lower than a threshold value (e.g., 0.1, 0.01, 0.001, 0.0001, etc.) can be defined as an abnormal/anomalous methylation pattern. Various methods known in the art can be used to calculate a p-value or expectedness of a methylation pattern or a methylation state vector. Exemplary methods provided herein involve use of a Markov chain probability that assumes methylation statuses of CpG sites to be dependent on methylation statuses of neighboring CpG sites. Alternate methods provided herein calculate the expectedness of observing a specific methylation state vector in healthy individuals by utilizing a mixture model including multiple mixture components, each being an independent-sites model where methylation at each CpG site is assumed to be independent of methylation statuses at other CpG sites.

Methods provided herein characterize DNA fragments as anomalous when they have a methylation pattern that is unusual in comparison to the methylation patterns of DNA fragments in reference samples, such as samples from individuals who have not been diagnosed with cancer. The likelihood of a particular methylation pattern being observed in reference samples can be represented as a p-value score. Exemplary methods provided herein for modeling the likelihood of a particular methylation pattern involve use of a Markov chain probability and a sliding window. If the p-value score falls below a threshold (e.g., 0.1, 0.01, 0.001, 0.0001, etc.), the DNA fragment having that methylation pattern is classified as being anomalous. Multiple p-value scores corresponding to hypermethylated or hypomethylated DNA fragments can be summed or averaged before being compared to the threshold value. Various methods known in the art can be adopted to compare p-value scores corresponding to the genomic region and the threshold value, including but not limited to arithmetic mean, geometric mean, harmonic mean, median, mode, etc.

The term "cancerous sample" as used herein refers to a sample comprising genomic DNAs from an individual diagnosed with cancer. The genomic DNAs can be, but are not limited to, cfDNA fragments or chromosomal DNAs from a subject with cancer. The genomic DNAs can be sequenced and their methylation status can be assessed by methods known in the art, for example, bisulfite sequencing. When genomic sequences are obtained from public database (e.g., The Cancer Genome Atlas (TCGA)) or experimentally obtained by sequencing a genome of an individual diagnosed with cancer, cancerous sample can refer to genomic DNAs or cfDNA fragments having the genomic sequences. The term "cancerous samples" as a plural refers to samples comprising genomic DNAs from multiple individuals, each individual diagnosed with cancer. In various embodiments, cancerous samples from more than 100, 300, 500, 1,000, 10,000, 20,000, 40,000, 50,000, or more individuals diagnosed with cancer are used.

The term "non-cancerous sample" as used herein refers to a sample comprising genomic DNAs from an individual not diagnosed with cancer. The genomic DNAs can be, but are not limited to, cfDNA fragments or chromosomal DNAs from a subject without cancer. The genomic DNAs can be sequenced and their methylation status can be assessed by methods known in the art, for example, bisulfite sequencing. When genomic sequences are obtained from public database (e.g., The Cancer Genome Atlas (TCGA)) or experimentally obtained by sequencing a genome of an individual without cancer, non-cancerous sample can refer to genomic DNAs or cfDNA fragments having the genomic sequences. The term "non-cancerous samples" as a plural refers to samples comprising genomic DNAs from multiple individuals, each individual is not diagnosed with cancer. In various embodiments, cancerous samples from more than 100, 300, 500, 1,000, 10,000, 20,000, 40,000, 50,000, or more individuals without cancer are used.

The term "training sample" as used herein refers to a sample used to train a classifier described herein and/or to select one or more genomic regions for cancer diagnosis. The training samples can comprise genomic DNAs or a modification there of, from one or more healthy subjects and from one or more subjects having a disease condition for diagnosis (e.g., cancer, a specific type of cancer, a specific stage of cancer, etc.). The genomic DNAs can be, but are not limited to, cfDNA fragments or chromosomal DNAs. The genomic DNAs can be sequenced and their methylation status can be assessed by methods known in the art, for example, bisulfite sequencing. When genomic sequences are obtained from public database (e.g., The Cancer Genome Atlas (TCGA)) or experimentally obtained by sequencing a genome of an individual, a training sample can refer to genomic DNAs or cfDNA fragments having the genomic sequences.

The term "test sample" as used herein refers to a sample from a subject, whose health condition was, has been or will be tested using a classifier and/or an assay panel described herein. The test sample can comprise genomic DNAs or a modification there of. The genomic DNAs can be, but are not limited to, cfDNA fragments or chromosomal DNAs.

The term "target genomic region" as used herein refers to a region in a genome selected for selected for analysis in test samples. An assay panel is generated with probes designed to hybridize to (and optionally pull down) nucleic acid fragments derived from the target genomic region or a fragment thereof. A nucleic acid fragment derived from the target genomic region refers to a nucleic acid fragment generated by degradation, cleavage, bisulfite conversion, or other processing of the DNA from the target genomic region.

The term "off-target genomic region" as used herein refers to a region in a genome which has not been selected for analysis in test samples, but has sufficient homology to a target genomic region to potentially be bound and pulled down by a probe designed to target the target genomic region. In one embodiment, an off-target genomic region is a genomic region that aligns to a probe along at least 45 bp with at least a 90% match rate.

The terms "converted DNA molecules," "converted cfDNA molecules," and "modified fragment obtained from processing of the cfDNA molecules" refer to DNA molecules obtained by processing DNA or cfDNA molecules in a sample for the purpose of differentiating a methylated nucleotide and an unmethylated nucleotide in the DNA or cfDNA molecules. For example, in one embodiment, the sample can be treated with bisulfite ion (e.g., using sodium bisulfite), as is well-known in the art, to convert unmethylated cytosines ("C") to uracils ("U"). In another embodiment, the conversion of unmethylated cytosines to uracils is accomplished using an enzymatic conversion reaction, for example, using a cytidine deaminase (such as APOBEC). After treatment, converted DNA molecules or cfDNA molecules include additional uracils which are not present in the original cfDNA sample. Replication by DNA polymerase of a DNA strand comprising a uracil results in addition of an adenine to the nascent complementary strand instead of the guanine normally added as the complement to a cytosine or methylcytosine.

The term "cell free nucleic acid," "cell free DNA," or "cfDNA" refers to nucleic acid fragments that circulate in an individual's body (e.g., bloodstream) and originate from one or more healthy cells and/or from one or more cancerous cells. Additionally, cfDNA may come from other sources such as viruses, fetuses, etc.

The term "circulating tumor DNA" or "ctDNA" refers to nucleic acid fragments that originate from tumor cells, which may be released into an individual's bloodstream as result of biological processes such as apoptosis or necrosis of dying cells or actively released by viable tumor cells.

The term "fragment" as used herein can refer to a fragment of a nucleic acid molecule. For example, in one embodiment, a fragment can refer to a cfDNA molecule in a blood or plasma sample, or a cfDNA molecule that has been extracted from a blood or plasma sample. An amplification product of a cfDNA molecule may also be referred to as a "fragment." In another embodiment, the term "fragment" refers to a sequence read, or set of sequence reads, that have been processed for subsequent analysis (e.g., for in machine-learning based classification), as described herein. For example, as is well known in the art, raw sequence reads can be aligned to a reference genome and matching paired end sequence reads assembled into a longer fragment for subsequent analysis.

The term "individual" refers to a human individual. The term "healthy individual" refers to an individual presumed not to have a cancer or disease.

The term "subject" refers to an individual whose DNA is being analyzed. A subject may be a test subject whose DNA is be evaluated using a targeted panel as described herein to evaluate whether or not the person has cancer or another disease. A subject may also be part of a control group known not to have cancer or another disease. A subject may also be part of a cancer or other disease group known to have cancer or another disease. Control and cancer/disease groups may be used to assist in designing or validating the targeted panel.

The term "sequence reads" as used herein refers to nucleotide sequences reads from a sample. Sequence reads can be obtained through various methods provided herein or as known in the art.

The term "sequencing depth" as used herein refers to the count of the number of times a given target nucleic acid within a sample has been sequenced (e.g., the count of sequence reads at a given target region). Increasing sequencing depth can reduce required amounts of nucleic acids required to assess a disease state (e.g., cancer or cancer tissue of origin).

The term "tissue of origin" or "TOO" as used herein refers to the organ, organ group, body region or cell type that cancer arises or originates from. The identification of a tissue of origin or cancer cell type typically allows for identification of the most appropriate next steps in the care continuum of cancer to further diagnose, stage, and decide on treatment.

The term "transition" generally refers to changes in base composition from one purine to another purine, or from one pyrimidine to another pyrimidine. For instance, the following changes are transitions: C→U, U→C, G→A, A→G, C→T, and T→C.

"An entirety of probes" of a panel or bait set or "an entirety of polynucleotide-containing probes" of a panel or bait set generally refers to all of the probes delivered with a specified panel or bait set. For instance, in some embodiments, a panel or bait set may include both (1) probes having features specified herein (e.g., probes for binding to cell-free DNA fragments corresponding to or derived from genomic regions set forth herein in one or more Lists) and (2) additional probes that do not contain such feature(s). The entirety of probes of a panel generally refers to all probes delivered with the panel or bait set, including such probes that do not contain the specified feature(s).

6.2. Other Interpretational Conventions

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

6.3. Cancer Assay Panel

In a first aspect, the present description provides a cancer assay panel (e.g., a bait set) comprising a plurality of probes. The probes can be polynucleotide-containing probes that are specifically designed to target one or more nucleic acid molecules corresponding to or derived from genomic regions that are differentially methylated in cancer compared to non-cancer samples as identified by methods provided herein. The probes are used as baits to collect cfDNA derived from target genomic regions that are differentially methylated in cancer. In a diagnostic assay, enrichment increases sensitivity and accuracy while reducing sequencing expenses.

For designing the cancer assay panel, an analytics system may collect samples corresponding to various outcomes under consideration, e.g., samples known to have cancer, samples considered to be healthy, samples from a known tissue of origin, etc. The sources of the cfDNA and/or ctDNA used to select target genomic regions can vary depending on the purpose of the assay. For example, different sources may be desirable for an assay intended to diagnose cancer generally, a specific type of cancer, a cancer stage, or a tissue of origin. These samples may be processed with whole-genome bisulfite sequencing (WGBS) or obtained from public database (e.g., TCGA). The analytics system may be any generic computing system with a computer processor and a computer-readable storage medium with instructions for executing the computer processor to perform any or all operations described in this present disclosure.

The analytics system may then select target genomic regions based on methylation patterns of nucleic acid fragments. One approach considers pairwise distinguishability between pairs of outcomes for regions or more specifically one or more CpG sites. Another approach considers distinguishability for regions or more specifically one or more CpG sites when considering each outcome against the remaining outcomes. From the selected target genomic regions with high distinguishability power, the analytics system may design probes to target nucleic acid fragments inclusive of the selected genomic regions. The analytics system may generate variable sizes of the cancer assay panel, e.g., where a small sized cancer assay panel includes probes targeting the most informative genomic region, a medium sized cancer assay panel includes probes from the small sized cancer assay panel and additional probes targeting a second tier of informative genomic regions, and a large sized cancer assay panel includes probes from the small sized and the medium sized cancer assay panels and even more probes targeting a third tier of informative genomic regions. With such cancer assay panels, the analytics system may train classifiers with various classification techniques to predict a sample's likelihood of having a particular outcome, e.g., cancer, specific cancer type, other disorder, etc.

Target genomic regions may be selected to maximize classification accuracy, subject to a size limitation (which is determined by sequencing budget and desired depth of sequencing). Potential target genomic regions can be ranked according to their tentative classification potential as described herein and then greedily added to a panel until the size limitation is reached.

A cancer assay panel can be used to detect the presence or absence of cancer generally, the stage (e.g., I, II, III or IV) of cancer, and/or the tissue of origin of a cancer. Depending on the purpose, a panel can include probes targeting genomic regions differentially methylated between general cancerous (pan-cancer) samples and non-cancerous samples. In some embodiments, a cancer assay panel is designed based on bisulfate sequencing data generated from the cfDNA and/or whole genomic DNA of a set of cancer and non-cancer individuals.

Each probe, probe pair, or probe set can be designed to target, by selective hybridization, one or more target genomic regions. The target genomic regions are selected based on several criteria designed to enhance selective enrichment of relevant cfDNA fragments while decreasing noise and non-specific binding. For example, a panel can include probes that can selectively hybridize to (i.e., bind to) and enrich cfDNA fragments that are differentially methylated in cancerous samples. Furthermore, the probes may be further designed to target genomic regions that are determined to have an anomalous methylation pattern comprising hypermethylation or hypomethylation. In some embodiments, a panel comprises both a first set of probes targeting hypermethylated fragments and a second set of probes targeting hypomethylated fragments. In some embodiments, the ratio between the first set of probes targeting hypermethylated fragments and the second set of probes targeting hypomethylated fragments (hyper:hypo ratio) ranges between 0.4 and 2, between 0.5 and 1.8, between 0.5 and 1.6, between 1.4 and 1.6, between 1.2 and 1.4, between 1 and 1.2, between 0.8 and 1, between 0.6 and 0.8 or between 0.4 and 0.6.

Sequencing of the enriched fragments provides information relevant to a diagnosis of cancer. Methods of identifying fragments having abnormal methylation patterns are provided in detail in Section 6.4.2 ("Anomalously methylated fragments") and methods of identifying fragments having hypomethylation or hypermethylation patterns are provided in detail in Section 6.4.3 ("Analysis of hyper or hypomethylated fragments").

For example, genomic regions can be selected when cfDNA and/or ctDNA fragments that align with a genomic region have a methylation pattern with a low p-value according to a Markov model trained on a set of non-cancerous samples. cfDNA and/or ctDNA fragments used to select genomic regions may additionally be required to contain at least a threshold number (e.g., 5) CpG's, and 70%, 75%, 80%, 85%, 90%, 95%, 98%, or 100% of the CPG sites may be required to be either methylated or unmethylated. Each of the probes can target at least 25 bp, 30 bp, 35 bp, 40 bp, 45 bp, 50 bp, 60 bp, 70 bp, 80 bp, 90 bp, 100 bp, 110 bp, or 120 bp of a genomic region. In some embodiments, the genomic regions is required to have less than 20, 15, 10, 8, or 6 methylation sites.

In some embodiments, target genomic region selection involves a calculation performed with respect to each CpG site. Specifically, a first count, $n_{cancer}$, is determined from the number of cancer-containing samples that include an abnormally hypermethylated and/or hypomethylated cfDNA and/or ctDNA fragment overlapping that CpG site, and a second count, $n_{non-cancer}$, is determined from the number of healthy samples that include an abnormally hypermethylated and/or hypomethylated cfDNA and/or ctDNA fragment overlapping that CpG site. Genomic regions can be selected based on criteria positively correlated $n_{cancer}$ and inversely correlated with $n_{non-cancer}$. In other embodiments, target genomic region selection involves a calculation performed with respect to a plurality of CpG sites.

In some embodiments, the number of non-cancerous samples ($n_{non-cancer}$) and the number of cancerous samples ($n_{cancer}$) having an abnormally hypermethylated and/or hypomethylated cfDNA and/or ctDNA fragment overlapping a CpG site are counted. A ranking score is then calculated for the CpG site. In some embodiments, the ranking score is equal to $(n_{cancer}+1)/(n_{cancer}+n_{non-cancer}+2)$. CpG sites ranked by this metric are greedily added to a panel until the panel size budget is exhausted. The process of selecting genomic regions indicative of cancer is further detailed herein.

Further filtration can be performed to select probes with high specificity for enrichment (i.e., high binding efficiency) of nucleic acids derived from targeted genomic regions. Probes can be filtered to reduce non-specific binding (or off-target binding) to nucleic acids derived from non-targeted genomic regions. In some embodiments, further filtration is performed to select probes for a cancer assay panel that will not pull down off-target genomic regions. In some embodiments, probes that can pull down off-target genomic regions are eliminated. In some embodiments, a threshold is set to define probes with an unacceptably high risk of off-target effects. In one embodiment, probes with more than 80%, 85%, 90%, 95% or 98% identity to a threshold number (e.g., 1, 2, 3, 4, 5, 10, 15, 20, 25 or more) of off-target genomic regions are eliminated from a panel. In some embodiments, probes are eliminated from a cancer assay panel if they comprise a sequence of at least 20, 25, 30, 35, 40, 45, 50, 55, or 60 nt with more than 80%, 85%, 90%, 95% or 98% identity to a threshold number (e.g., 1, 2, 3, 4, 5, 10, 15, 20, 25 or more) of off-target genomic regions. Filtering removes repetitive probes that can pull down off-target fragments, which are not desired and can impact assay efficiency.

A fragment-probe overlap of at least 45 bp enables a non-negligible amount of pulldown under certain hybridization conditions. Thus, in some embodiments, probes are eliminated from a cancer panel if they comprise a sequence of at least 45 nt with more than 80%, 85%, 90%, 95% or 98% identity to 1, 2, 3, 4, 5, 10, 15, 20, 25 or more off-target genomic regions.

In some embodiments, the probes of a cancer assay panel are designed to hybridize to converted cfDNA derived from target genomic regions. After hybridization, target polynucleotides can be recovered and/or isolated, optionally amplified, and sequenced by any suitable method. The sequence reads provide information relevant for detection of cancer, diagnosis of cancer, and assessment of a cancer tissue of origin or type of cancer. To this end, a panel may be designed to include a plurality of probes that can capture fragments that can together provide information relevant to cancer detection and diagnosis of cancer. In some embodiments, a panel includes at least 50, 60, 70, 80, 90, 100, 120, 150, or 200 different pairs of probes. In other embodiments, a panel includes at least at least 500, 1,000, 2,000, 2,500, 5,000, 10,000, 12,000, 15,000, 20,000, 30,000, 40,000, 50,000, or 100,000 probes. The plurality of probes together can comprise at least 20,000, 30,000, 40,000, 50,000, 75,000, 0.1 million, 0.2 million, 0.4 million, 0.6 million, 0.8 million, 1 million, 2 million, 3 million, 4 million, 5 million, 6 million, 7 million, 8 million, 9 million, or 10 million nucleotides. Optionally, the sequence at one or both ends of a probe overlaps with the sequence of other probes targeting the same genomic region or an adjacent genomic region.

Specifically, in some embodiments, the cancer assay panel comprises at least 50 pairs of probes, wherein each pair of the at least 50 pairs comprises two probes configured to overlap each other by an overlapping (e.g., identical) sequence, wherein the overlapping sequence comprises a 30-nucleotide sequence, and wherein the 30-nucleotide sequence is configured to hybridize to a modified fragment obtained from processing of the cfDNA molecules corresponding to one or more genomic regions, wherein each of the genomic regions comprises at least five methylation sites, and wherein the at least five methylation sites have an anomalous methylation pattern in training samples. In other words, when cfDNA molecules in training samples corresponding to the genomic region are analyzed, they have methylation status vectors appearing less frequently than a threshold value in reference samples.

In other embodiments, the cancer assay panel comprises at least 500 pairs of probes, wherein each pair of the at least 500 pairs comprises two probes configured to overlap each other by an overlapping sequence, wherein the overlapping sequence comprises a 30-nucleotide sequence, and wherein the 30-nucleotide sequence is configured to hybridize to a modified fragment obtained from processing of the cfDNA molecules corresponding to one or more genomic regions, wherein each of the genomic regions comprises at least five methylation sites, and wherein the at least five methylation sites have an anomalous methylation pattern in training samples. Again, when cfDNA molecules in training samples corresponding to the genomic region are analyzed, they have methylation status vectors appearing less frequently than a threshold value in reference samples.

In a preferred embodiment, the at least five methylation sites are differentially methylated either between cancerous and non-cancerous samples or between one or more pairs of samples from different cancer types. In some embodiments, the converted cfDNA molecules comprise cfDNA molecules treated (e.g., via bisulfite treatment or enzymatic conversion) to convert unmethylated C (cytosine) to U (uracil). In some cases, the uracil is further converted to thymine (e.g., upon PCR amplification).

The selected target genomic regions are optionally located in various positions in a genome, including but not limited to promoters, enhancers, exons, introns, and intergenic regions. In certain embodiments, the target genomic regions comprise genes and/or transcriptional control regions that are differentially expressed in cancer versus non-cancer, in different stages of cancer, and/or in cancers arising from different tissues of origin.

A cancer assay panel designed by methods provided herein may comprise at least 1,000 pairs of probes, each pair of which comprises two probes configured to overlap each other by an overlapping sequence comprising a 30-nucleotide fragment. The 30-nucleotide fragment comprises at least three, at least four, at least five of more CpG sites, wherein at least 70%, at least 80%, or at least 90% of the at least three, at least four, at least five, or more CpG sites are either CpG or UpG. The 30-nucleotide fragment is configured to bind to one or more cfDNA fragments derived from genomic regions in cancerous samples, wherein the one or more genomic regions have at least three, at least four, at least five or more methylation sites with an abnormal methylation pattern compared to DNA molecules from a non-cancer sample.

Another cancer assay panel comprises at least 2,000 probes, each of which is designed as a hybridization probe complementary to one or more genomic regions. Each of the genomic regions is selected based on the criteria that it comprises (i) at least 30 nucleotides, and (ii) at least three, at least four, at least five, or more methylation sites, wherein the at least five methylation sites have an abnormal methylation pattern and are either hypomethylated or hypermethylated.

In some instances, primers may be used to specifically amplify targets/biomarkers of interest (e.g., by PCR), thereby enriching the sample for desired targets/biomarkers (optionally without hybridization capture). For example, forward and reverse primers can be prepared for each genomic region of interest and used to amplify fragments that correspond to or are derived from the desired genomic region. Thus, while the present disclosure pays particular attention to cancer assay panels and bait sets for hybridization capture, the disclosure is broad enough to encompass other methods for enrichment of cell-free DNA.

Accordingly, a skilled artisan, with the benefit of this disclosure, will recognize that methods analogous to those described herein in connection with hybridization capture can alternatively be accomplished by replacing hybridization capture with some other enrichment strategy, such as PCR amplification of cell-free DNA fragments that correspond with genomic regions of interest. In some embodiments, bisulfite padlock probe capture is used to enrich regions of interest, such as is described in Zhang et al. (US 2016/0340740). In some embodiments, additional or alternative methods are used for enrichment (e.g., non-targeted enrichment) such as reduced representation bisulfite sequencing, methylation restriction enzyme sequencing, methylation DNA immunoprecipitation sequencing, methyl-CpG-binding domain protein sequencing, methyl DNA capture sequencing, or microdroplet PCR.

6.3.1. Probes

Cancer assay panels provided herein may include a panel having a set of hybridization probes (also referred to herein as "probes") designed to enrich selected target genomic regions by pulling down nucleic acid fragments of interest. The probes are designed to interrogate the methylation status of target genomic regions (e.g., of a human or other organism) that are suspected to correlate with the presence or absence of cancer generally, cancer stage, and/or tissue of origin.

The probes can be designed to anneal (or hybridize) to a target (complementary) strand of DNA or RNA. The target strand can be the "positive" strand (e.g., the strand transcribed into mRNA and subsequently translated into a protein) or the complementary "negative" strand. In a particular embodiment, a cancer assay panel includes two sets of probes for a target genomic region, one targeting the positive strand and the other targeting the negative strand. In certain embodiments, probes targeting different strands of a DNA sequence can have regions of sequence complementarity to each other.

Probes are optionally designed to hybridize to native DNA or to converted DNA. cfDNA, ctDNA and/or chromosomal DNA can be converted by various methods known in the art to preserve epigenetic marks such as methylation.

Optionally, DNA is converted by bisulfite or enzymatic treatment, which converts unmethylated cytosines into uracils. Thus, the methylation pattern determines which cytosines in a CpG sequence are converted to uracil. Unmethylated CpG sites in a target region are converted by bisulfite (or enzymatic means) to UpG sites, If the target DNA is amplified after conversion by a process employing DNA polymerase, UpG sequences are further transformed to TpG sequences, and a complementary probe would have a CpA sequence. Methylated CpG sites in a target region retain their CpG sequence, so a complementary probe would also have a CpG sequence. Cytosines that are not at a CpG sequences are generally not methylated. These cytosines are generally converted to uracils, which are further transformed to thymidine after amplification, so probes complementary to bisulfite converted DNA comprise an A for each converted C that is not in a CpG site.

Probes are optionally designed under an assumption that all CpG sites are methylated in some target genomic regions (perfect hypermethylation), whereas no CpG sites are methylated in other target genomic regions (perfect hypomethylation). Stated differently, probes designed to target a hypomethylated region may be designed to be complementary to a region in which all CpG sites have been converted UpGs, whereas probes designed to target a hypermethylated region may be designed to be complementary to a region in which none of the CpG sites have been converted.

Since the probes may be configured to hybridize to a converted DNA or converted cfDNA molecule derived from one or more genomic regions, the probes can have a sequence different from the targeted genomic region. For example, a DNA molecule containing unmethylated CpG site will be converted to include UpG because unmethylated cytosines are converted to uracils by a conversion reaction (e.g., bisulfite treatment). As a result, a probe is configured to hybridize to a sequence including UpG instead of a naturally existing unmethylated CpG. Accordingly, a complementary site in the probe to the unmethylated site can comprise CpA instead of CpG, and some probes targeting a hypomethylated site where all methylation sites are unmethylated can have no guanine (G) bases. In some embodiments, at least 3%, 5%, 10%, 15%, 20%, 30%, or 40% of the probes lack G (Guanine). In some embodiments, at least 80, 85, 90, 92, 95, 98% of the probes on the panel have exclusively either CpG or CpA on CpG detection sites. Accordingly, in some embodiments, polynucleotide-containing probes have a nucleic acid sequence that is either (1) identical in sequence to a sequence within a target genomic region (e.g., target genomic regions set forth herein in any one of Lists 1-8) or (2) varies with respect to a sequence within the genomic region only one or more transitions (e.g., changes in base composition at a site due to bisulfate conversion or other conversion techniques), wherein each respective transition in the one or more transitions occurs at a nucleotide corresponding to a CpG site in the genomic region.

In some embodiments, probes on the panel comprise less than 20, 15, 10, 8, or 6 CpG detection sites. In some embodiments, probes on the panel comprise more than 5, 6, 7, 8, 9, or 10 CpG detection sites.

In some embodiments, probes are conjugated to a tag (e.g., a non-nucleic acid affinity moiety), such as a biotin moiety. In some embodiments, probes are affixed to a solid support, such as an array.

A cancer assay panel that interrogates methylation status can also be designed to interrogate other genetic or epigenetic marks that are different between cfDNA in cancer and healthy samples. In some embodiments, probes are designed to enrich for all cfDNA from a particular target region regardless of the methylation status of the cfDNA molecule. This might be because the target genomic region is not highly methylated or unmethylated, or for the purpose of targeting small mutations or SCNAs rather than methylation changes.

The probes optionally range in length from 10s to 100s of nucleotides. The probes can comprise at least 20, 30, 50, 75, 100, or 120 nucleotides. The probes can have a length of less than 300, 250, 200, or 150 nucleotides. In some embodiments, the probes comprise 100-150 nucleotides. In one particular embodiment, the probes are 120 nucleotides in length.

In some embodiments, the probes are designed in a "2× tiled" fashion to cover overlapping portions of a target region. Each probe optionally overlaps in coverage at least partially with another probe in the library. In such embodiments, the panel contains multiple pairs of probes, with each probe in a pair overlapping the other by at least 25, 30, 35, 40, 45, 50, 60, 70, 75 or 100 nucleotides. In some embodiments, the overlapping sequence can be designed to be complementary to a target genomic region (or cfDNA derived therefrom) or to be complementary to a sequence with homology to a target region or cfDNA. Thus, in some embodiments, at least two probes are complementary to the same sequence within a target genomic region, and a nucleotide fragment corresponding to or derived from the target genomic region can be bound and pulled down by at least one of the probes. Other levels of tiling are possible, such as 3× tiling, 4× tiling, etc., wherein each nucleotide in a target region can bind to more than two probes.

Figure 1A:
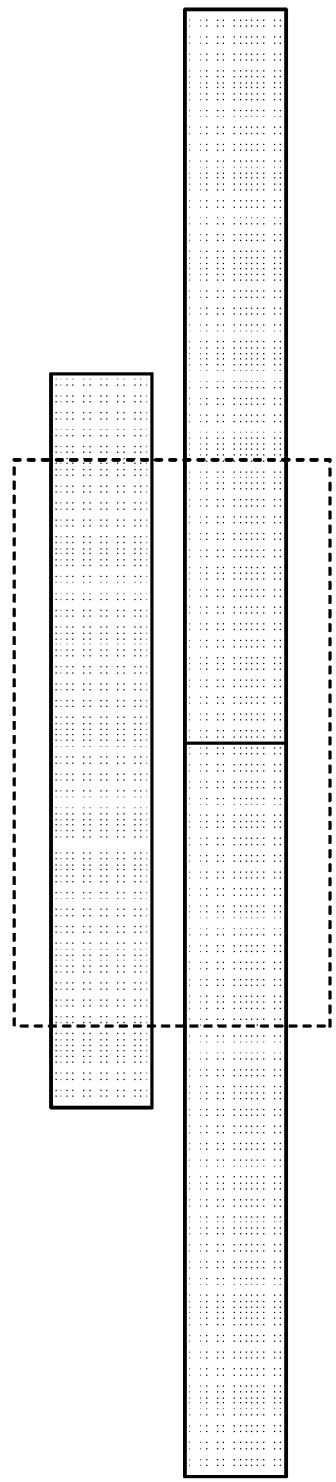
FIGS. 1A-1B illustrate a 2× tiled probe design where, for each strand of DNA, each base in a target region (boxed in the dotted rectangles) is covered by (e.g., complementary to) exactly two probes.
Figure 1B:
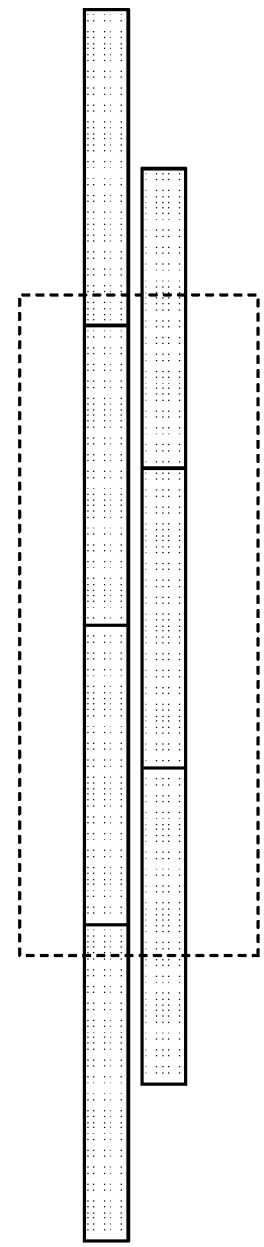

In one embodiment, each base in a target genomic region is overlapped by exactly two probes, as illustrated in FIG. 1. A single pair of probes is enough to pull down a genomic region if the overlap between the two probes is longer than the target genomic region and extends beyond both ends of the target genomic region. In some instances, even relatively small target regions may be targeted with three probes (see FIG. 1A). A probe set comprising three or more probes is optionally used to capture a larger genomic region. See FIG. 1B. In some embodiments, subsets of probes will collectively extend across an entire genomic region (e.g., may be complementary to non-converted or converted fragments from the genomic region). A tiled probe set optionally comprises probes that collectively include at least two probes that overlap every nucleotide in the genomic region. FIGS. 1A and 1B. This is done to ensure that cfDNAs comprising a small portion of a target genomic region at one end will have a substantial overlap extending into the adjacent non-targeted genomic region with at least one probe, to provide for efficient capture.

For example, a 100 bp cfDNA fragment comprising a 30 nt target genomic region can be guaranteed to have at least 65 bp overlap with at least one of the overlapping probes. Other levels of tiling are possible. For example, to increase target size and add more probes in a panel, probes can be designed to expand a 30 bp target region by at least 70 bp, 65 bp, 60 bp, 55 bp, or 50 bp. To capture any fragment that overlaps the target region at all (even if by only 1 bp), the probes can be designed to extend past the ends of the target region on either side.

In one particular embodiment, the smallest target genomic region is 30 bp. When a new CpG site is added to the panel (based on the greedy selection as described above), a new target of 30 nt is centered on the CpG site of interest. Then, it is checked whether each edge of this new target is close enough to other targets such that they can be merged. Merging avoids a panel comprising close but distinct targets with overlapping probes. This is based on a "merge distance" parameter which extends about 100 nt, 150 nt, 200 nt, 250 nt, or 300 nt on either side of every target region. Merger creates a larger target genomic region. If a new CpG site is merged into targets on both sides, the number of target genomic regions is reduced.

In some embodiments, an assay panel provided herein comprises a plurality of polynucleotide probes configured to hybridize to a modified fragment obtained from processing of the cfDNA molecules, wherein each of the cfDNA molecules corresponds to or is derived from one or more genomic regions. In some embodiments, at least 15%, 20%, 30%, or 40% of the genomic regions are in exons or introns. In some embodiments, at least 5%, 10%, 15%, 20%, 30% or 40% of the genomic regions are in exons. In some embodiments, less than 5%, 10%, 15%, 20%, 25%, or 30% of the genomic regions are in intergenic regions.

In some embodiments, the entire probes on the panel together are configured to hybridize to modified fragments obtained from the cfDNA molecules corresponding to or derived from at least 20%, 30%, 40%, 50%, 60%, 70%, 80%, 90% or 95% of the genomic regions in one or more of Lists 1-8. In some embodiments, the entire probes on the panel together are configured to hybridize to modified fragments obtained from the cfDNA molecules corresponding to or derived from at least 20%, 30%, 40%, 50%, 60%, 70%, 80%, 90% or 95% of the genomic regions in one or more of the genomic regions in List 1. In some embodiments, the entire probes on the panel together are configured to hybridize to modified fragments obtained from the cfDNA molecules corresponding to or derived from at least 20%, 30%, 40%, 50%, 60%, 70%, 80%, 90% or 95% of the genomic regions in one or more of the genomic regions in List 2. In some embodiments, the entire probes on the panel together are configured to hybridize to modified fragments obtained from the cfDNA molecules corresponding to or derived from at least 20%, 30%, 40%, 50%, 60%, 70%, 80%, 90% or 95% of the genomic regions in one or more of the genomic regions in List 3. In some embodiments, the entire probes on the panel together are configured to hybridize to modified fragments obtained from the cfDNA molecules corresponding to or derived from at least 20%, 30%, 40%, 50%, 60%, 70%, 80%, 90% or 95% of the genomic regions in one or more of the genomic regions in List 5. In some embodiments, the entire probes on the panel together are configured to hybridize to modified fragments obtained from the cfDNA molecules corresponding to or derived from at least 20%, 30%, 40%, 50%, 60%, 70%, 80%, 90% or 95% of the genomic regions in one or more of the genomic regions in List 7. In some embodiments, the entire probes on the panel together are configured to hybridize to modified fragments obtained from the cfDNA molecules corresponding to or derived from at least 20%, 30%, 40%, 50%, 60%, 70%, 80%, 90% or 95% of the genomic regions in one or more of the genomic regions in List 8. In some embodiments, the entire probes on the panel together are configured to hybridize to modified fragments obtained from the cfDNA molecules corresponding to or derived from at least 20%, 30%, 40%, 50%, 60%, 70%, 80%, 90% or 95% of the genomic regions in one or more of List 4. In some embodiments, the entire probes on the panel together are configured to hybridize to modified fragments obtained from the cfDNA molecules corresponding to or derived from at least 20%, 30%, 40%, 50%, 60%, 70%, 80%, 90% or 95% of the genomic regions in one or more of the genomic regions in List 6. In some embodiments, the entire probes on the panel together are configured to hybridize to modified fragments obtained from the cfDNA molecules corresponding to or derived from at least 500, 1,000, 5000, 10,000 or 15,000 genomic regions in one or more of Lists 1-8.

6.4. Methods of Selecting Target Genomic Regions

In another aspect, methods are provided for identifying anomalously methylated DNA molecules from a sample. In some embodiments, the methods disclosed herein can be used to select target genomic regions for detecting cancer, assessing a cancer tissue of origin, or type of cancer. The targeted genomic regions can be used to design and manufacture probes for a cancer assay panel. Methylation status of the target genomic regions can be screened using the cancer assay panel. In other embodiments, these methods can be used as part of a filtering process to limit a data set (e.g., a sequencing data set) to reduce subsequent processing or analysis requirements. For example, the methods disclosed herein can be used to set a threshold for anomalously methylated fragments, which are likely derived from cancer or cancer cells, and the threshold used as a to filter out sequence reads or fragments that don't meet the threshold, and thus, are more likely derived from healthy cells.

6.4.1. Generation of Data Structure

Figure 2:
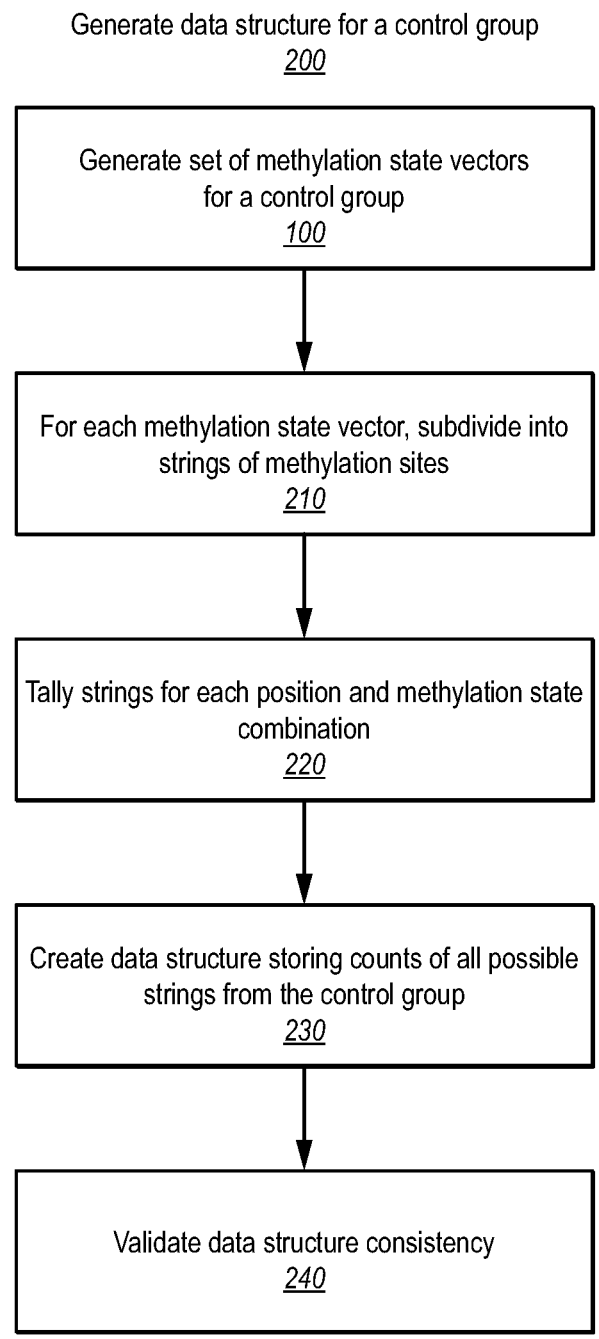
FIG. 2 is a flowchart describing a process of creating a data structure for a control group, according to an embodiment.

FIG. 2 is a flowchart describing a process 200 of generating a data structure for a healthy control group, according to an embodiment. To create a healthy control group data structure, the analytics system receives sequences from a plurality of DNA fragments (e.g., cfDNA and/or ctDNA) from a plurality of healthy subjects. A methylation state vector is identified for each fragment, for example via the process 100.

The analytics system subdivides 210 the methylation state vector of each DNA fragment into strings of CpG sites. In one embodiment, the analytics system subdivides 210 the methylation state vector such that the resulting strings are all less than a given length. For example, dividing a methylation state vector of length 11 may be subdivided into strings of length less than or equal to 3 would result in 9 strings of length 3, 10 strings of length 2, and 11 strings of length 1. In another example, a methylation state vector of length 7 being subdivided into strings of length less than or equal to 4 would result in 4 strings of length 4, 5 strings of length 3, 6 strings of length 2, and 7 strings of length 1. If the methylation state vector resulting from a DNA fragment is shorter than or the same length as the specified string length, then the methylation state vector may be converted into a single string containing all CpG sites of the vector.

The analytics system tallies 220 the strings by counting, for each possible CpG site and possibility of methylation states in the vector, the number of strings present in the control group having the specified CpG site as the first CpG site in the string and having that possibility of methylation states. For a string length of three at a given CpG site, there are 2^3 or 8 possible string configurations. For each CpG site, the analytics system tallies 220 how many occurrences of each possible methylation state vector appear up in the control group. This may involve tallying the following quantities: $<M_x, M_{x+1}, M_{x+2}>$, $<M_x, M_{x+1}, U_{x+2}>$, ..., $<U_x, U_{x+1}, U_{x+2}>$ for each starting CpG site in the reference genome. The analytics system creates 230 a data structure storing the tallied counts for each string possibility at each starting CpG.

There are several benefits to setting an upper limit on string length. First, depending on the maximum length for a string, the size of the data structure created by the analytics system can dramatically increase in size. For instance, a maximum string length of 4 means that there are at most $2^4$ numbers to tally at every CpG. Increasing the maximum string length to 5 doubles the possible number of methylation states to tally. Reducing string size helps reduce the computational and data storage burden of the data structure. In some embodiments, the string size is 3. In some embodiments, the string size is 4. A second reason to limiting the maximum string length is to avoid overfitting downstream models. Calculating probabilities based on large strings of CpG sites can be problematic if the long CpG strings do not have a strong biological effect on the outcome (e.g., predictions of anomalousness that predictive of the presence of cancer), as it requires a significant amount of data that may not be available, and would thus be too sparse for a model to perform appropriately. For example, calculating a probability of anomalousness/cancer conditioned on the prior 100 CpG sites would require counts of strings in the data structure of length 100, ideally some matching exactly the prior 100 methylation states. If only sparse counts of strings of length 100 are available, there will be insufficient data to determine whether a given string of length of 100 in a test sample is anomalous or not.

6.4.1. Validation of Data Structure

Once the data structure has been created, the analytics system may seek to validate 240 the data structure and/or any downstream models making use of the data structure.

This first type of validation ensures that potential cancerous samples are removed from the healthy control group so as to introduce bias into the healthy data structure. This type of validation checks consistency within the control group's data structure. For example, the healthy control group may contain a sample from an individual with an undiagnosed cancer that contains a plurality of anomalously methylated fragments. The analytics system may perform various calculations to determine whether to exclude data from a subject with apparently undiagnosed cancer.

A second type of validation checks the probabilistic model used to calculate p-values with the counts from the data structure itself (i.e., from the healthy control group). A process for p-value calculation is described below in conjunction with FIG. 5. Once the analytics system generates a p-value for the methylation state vectors in the validation group, the analytics system builds a cumulative density function (CDF) with the p-values. With the CDF, the analytics system may perform various calculations on the CDF to validate the control group's data structure. One test uses the fact that the CDF should ideally be at or below an identity function, such that $CDF(x) \leq x$. On the converse, being above the identity function reveals some deficiency within the probabilistic model used for the control group's data structure. For example, if 1/100 of fragments have a p-value score of 1/1000 meaning $CDF(1/1000)=1/100>1/1000$, then the second type of validation fails indicating an issue with the probabilistic model. See e.g., U.S. application Ser. No. 16/352,602, published as U.S. Publ. No. 2019/0287652, which is hereby incorporated by reference in its entirety.

A third type of validation uses a healthy set of validation samples separate from those used to build the data structure. This tests if the data structure is properly built and the model works. An exemplary process for carrying out this type of validation is described below in conjunction with FIG. 3. The third type of validation can quantify how well the healthy control group generalizes the distribution of healthy samples. If the third type of validation fails, then the healthy control group does not generalize well to the healthy distribution.

A fourth type of validation tests with samples from a non-healthy validation group. The analytics system calculates p-values and builds the CDF for the non-healthy validation group. With a non-healthy validation group, the analytics systems expects to see the $CDF(x)>x$ for at least some samples or, stated differently, the converse of what was expected in the second type of validation and the third type of validation with the healthy control group and the healthy validation group. If the fourth type of validation fails, then this is indicative that the model is not appropriately identifying the anomalousness that it was designed to identify.

Figure 3:
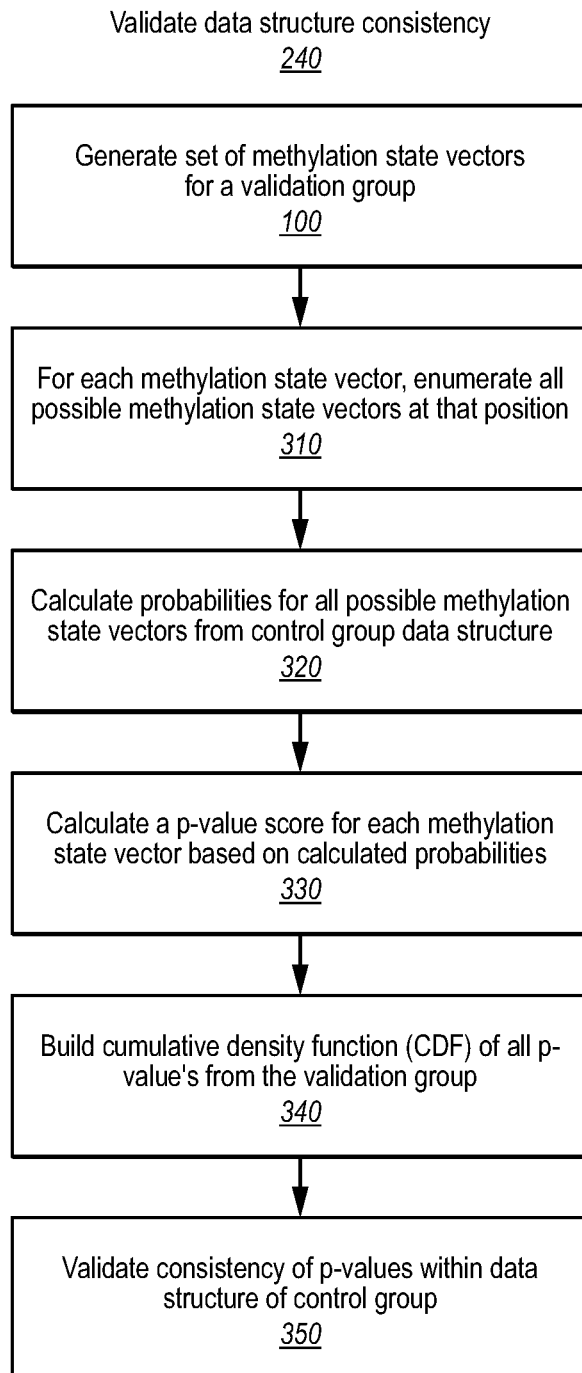
FIG. 3 is a flowchart describing an additional step of validating the data structure for the control group of FIG. 2, according to an embodiment.

FIG. 3 is a flowchart describing an additional step 240 of validating the data structure for the control group of FIG. 2, according to an embodiment. In this step 240 of validating the data structure, the analytics system performs the fourth type of validation test as described above which utilizes a validation group with a supposedly similar composition of subjects, samples, and/or fragments as the control group. For example, if the analytics system selected healthy subjects without cancer for the control group, then the analytics system also uses healthy subjects without cancer in the validation group.

The analytics system takes the validation group and generates 100 a set of methylation state vectors as described in FIG. 2. The analytics system performs a p-value calculation for each methylation state vector from the validation group. The p-value calculation process will be further described in conjunction with FIGS. 4 & 5. For each possible methylation state vector, the analytics system calculates 320 a probability from the control group's data structure. Once the probabilities are calculated for the possibilities of methylation state vectors, the analytics system calculates 330 a p-value score for that methylation state vector based on the calculated probabilities. The p-value score represents an expectedness of finding that specific methylation state vector and other possible methylation state vectors having even lower probabilities in the control group. A low p-value score, thereby, generally corresponds to a methylation state vector which is relatively unexpected in comparison to other methylation state vectors within the control group, whereas a high p-value score generally corresponds to a methylation state vector which is relatively more expected in comparison to other methylation state vectors found in the control group. Once the analytics system generates a p-value score for the methylation state vectors in the validation group, the analytics system builds 340 a cumulative density function (CDF) with the p-value scores from the validation group. The analytics system validates 370 consistency of the CDF as described above in the fourth type of validation tests.

6.4.2. Anomalously Methylated Fragments

Figure 4:
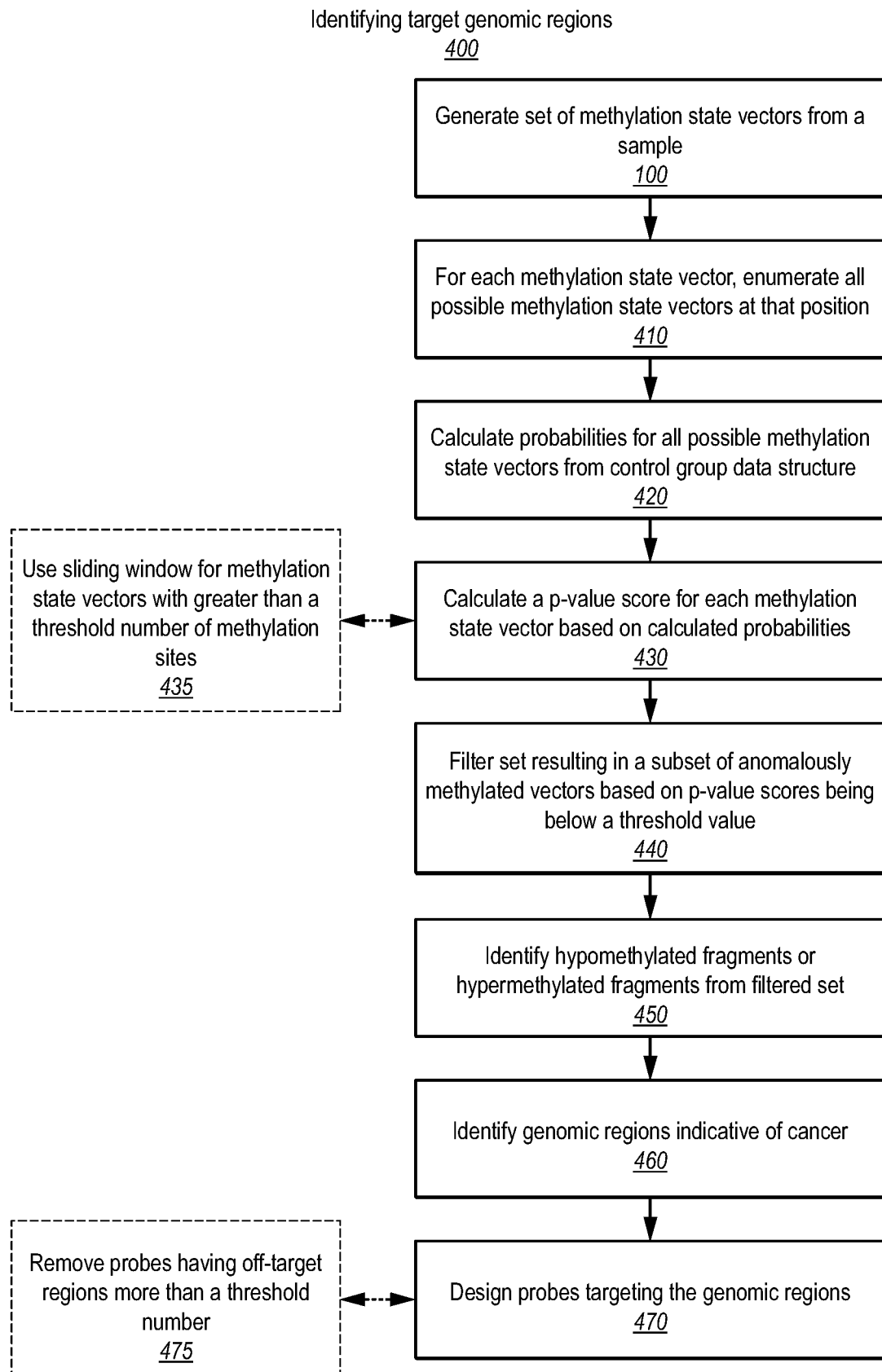
FIG. 4 is a flowchart describing a process for selecting genomic regions for designing probes for a cancer assay panel, according to an embodiment.

Anomalously methylated fragments having abnormal methylation patterns are selected as target genomic regions, according to an embodiment as outlined in FIG. 4. An exemplary process of selected anomalously methylated fragments 440 is visually illustrated in FIG. 5, and is further described below the description of FIG. 4. In process 400, the analytics system generates 100 methylation state vectors from cfDNA fragments of the sample. The analytics system handles each methylation state vector as follows.

In some embodiments, the analytics system filters 405 fragments having indeterminate states at one or more CpG sites. In such embodiments, the analytics system implements a prediction model to identify fragments not likely to have an anomalous methylation pattern for filtering. For a sample fragment, the prediction model calculates a sample probability that the sample fragment's methylation state vector occurs in comparison to the healthy control group data structure. The prediction model randomly samples a subset of possible methylation state vectors encompassing the CpG sites in the sample fragment's methylation state vector. The prediction model calculates a probability corresponding to each of the sampled possible methylation state vectors. Probability calculations for the fragment's methylation state vector and the sampled possible methylation state vectors can be calculated according to a Markov chain model as will be described below in Section 6.4.2.1 ("P-Value Score Calculation"). The prediction model calculates a proportion of the sampled possible methylation state vectors corresponding to probabilities less than or equal to the sample probability. The prediction model generates an estimated p-value score for the fragment based on the calculated proportion. The prediction model may filter fragments corresponding to p-value scores above a threshold and retain fragments corresponding to p-value scores below the threshold. Again, see e.g., U.S. application Ser. No. 16/352,602, published as U.S. Publ. No. 2019/0287652, which is hereby incorporated by reference in its entirety.

In additional embodiments, the prediction model may calculate a confidence probability that is used by the prediction model to determine when to continue or when to terminate sampling. The confidence probability describes how likely it is that a fragment's true p-value score is below a threshold based on the estimated p-value score and the probabilities of the sampled possible methylation state vectors. The prediction model may sample one or more possible additional methylation state vectors while iteratively calculating the estimated p-value score and the confidence probability. The prediction model may then terminate sampling when the confidence probability is above a confidence threshold.

For a given methylation state vector, the analytics system enumerates 410 all possible methylation state vectors having the same starting CpG site and same length (i.e., set of CpG sites) as the methylation state vector. There are only two possible states at each CpG site, methylated or unmethylated, and thus the count of distinct possibilities of methylation state vectors depends on a power of 2, such that a methylation state vector of length n would be associated with $2^n$ possible of methylation state vectors. With methylation state vectors inclusive of indeterminate states for one or more CpG sites, the analytics system may enumerate 410 possibilities of methylation state vectors considering only CpG sites that have observed states.

The analytics system calculates 420 the probability of observing each possible methylation state vector for the identified starting CpG site/methylation state vector length by accessing the healthy control group data structure. In one embodiment, calculating the probability of observing a given possibility uses Markov chain probability to model the joint probability calculation which will be described in greater detail with respect to FIG. 5. In other embodiments, calculation methods other than Markov chain probabilities are used to determine the probability of observing each possible methylation state vector.

The analytics system calculates 430 a p-value score for the methylation state vector using the calculated probabilities for each possibility. In one embodiment, this includes determining the calculated probability corresponding to the possibility that matches the methylation state vector in question. Specifically, this is the probability of having the same set of CpG sites, or the same starting CpG site, length and methylation status as the methylation state vector. The analytics system sums the calculated probabilities of any possibilities having probabilities less than or equal to the identified probability to generate the p-value score.

This p-value represents the probability of observing the methylation state vector of the fragment or other methylation state vectors even less probable in the healthy control group. A low p-value score, thereby, generally corresponds to a methylation state vector which is rare in a healthy subject, and which causes the fragment to be labeled anomalously methylated, relative to the healthy control group. A high p-value score generally relates to a methylation state vector is expected to be present, in a relative sense, in a healthy subject. If the healthy control group is a non-cancerous group, for example, a low p-value indicates that the fragment is anamolously methylated relative to the non-cancer group, and therefore possibly indicative of the presence of cancer in the test subject.

As above, the analytics system calculates p-value scores for each of a plurality of methylation state vectors, each representing a cfDNA and/or ctDNA fragment in the test sample. To identify which of the fragments are anomalously methylated, the analytics system may filter 440 the set of methylation state vectors based on their p-value scores. In one embodiment, filtering is performed by comparing the p-values scores against a threshold and keeping only those fragments below the threshold. This threshold p-value score could be on the order of 0.1, 0.01, 0.001, 0.0001, or similar.

6.4.2.1. P-Value Score Calculation

Figure 5:
FIG. 5 is an illustration of an example p-value score calculation, according to an embodiment.

FIG. 5 is an illustration 500 of an example p-value score calculation, according to an embodiment. To calculate a p-value score given a test methylation state vector 505, the analytics system takes that test methylation state vector 505 and enumerates 410 possibilities of methylation state vectors. In this illustrative example, the test methylation state vector 505 is $<M_{23}, M_{24}, M_{25}, U_{26}>$. As the length of the test methylation state vector 505 is 4, there are $2^4$ possibilities of methylation state vectors encompassing CpG sites 23-26. In a generic example, the number of possibilities of methylation state vectors is $2^n$, where n is the length of the test methylation state vector or alternatively the length of the sliding window (described further below).

The analytics system calculates 420 probabilities 515 for the enumerated possible methylation state vectors. As methylation is conditionally dependent on methylation state of nearby CpG sites, one way to calculate the probability of observing a given methylation state vector possibility is to use a Markov chain model. Generally, a methylation state vector such as $<S_1, S_2, S_n>$, where S denotes the methylation state whether methylated (denoted as M), unmethylated (denoted as U), or indeterminate (denoted as I), has a joint probability that can be expanded using the chain rule of probabilities as:

$$P(<S_1,S_2,\ldots,S_n>)=P(S_n|S_1,\ldots,S_{n-1})*$$
$$P(S_{n-1}|S_1,\ldots,S_{n-2})* \ldots *P(S_2|S_1)*P(S_1).$$

A Markov chain model can be used to calculate the conditional probabilities of each possibility more efficiently. In one embodiment, the analytics system selects a Markov chain order k which corresponds to how many prior CpG sites in the vector (or window) to consider in the conditional probability calculation, such that the conditional probability is modeled as $P(S_n|S_1, \ldots S_{n-1}) \sim P(S_n|S_{n-k-2}, \ldots, S_{n-1})$.

To calculate each Markov modeled probability for a possibility of methylation state vector, the analytics system accesses the control group's data structure, specifically the counts of various strings of CpG sites and states. To calculate $P(M_n\ S_{n-k-2}, \ldots, S_{n-1})$, the analytics system takes a ratio of the stored count of the number of strings from the data structure matching $<S_{n-k-2}, \ldots, S_{n-1}, M_n>$ divided by the sum of the stored count of the number of strings from the data structure matching $<S_{n-k-2}, \ldots, S_{n-1}, M_n>$ and $<S_{n-k-2}, \ldots, S_{n-1}, U_n>$. Thus, $P(M_n|S_{n-k-2}, \ldots, S_{n-1})$, is calculated ratio having the form:

$$\frac{\#\ of\ <S_{n-k-2,\ldots},S_{n-1},M_n>}{\#\ of\ <S_{n-k-2,\ldots},S_{n-1},M_n> + \#\ of\ <S_{n-k-2,\ldots},S_{n-1},U_n>}.$$

The calculation may additionally implement a smoothing of the counts by applying a prior distribution. In one embodiment, the prior distribution is a uniform prior as in Laplace smoothing. As an example of this, a constant is added to the numerator and another constant (e.g., twice the constant in the numerator) is added to the denominator of the above equation. In other embodiments, an algorithmic technique such as Knesser-Ney smoothing is used.

In the illustration, the above denoted formulas are applied to the test methylation state vector 505 covering sites 23-26. Once the calculated probabilities 515 are completed, the analytics system calculates 430 a p-value score 525 that sums the probabilities that are less than or equal to the probability of possibility of methylation state vector matching the test methylation state vector 505.

In embodiments with indeterminate states, the analytics system may calculate a p-value score summing out CpG sites with indeterminates states in a fragment's methylation state vector. The analytics system identifies all possibilities that have consensus with all methylation states of the methylation state vector, excluding the indeterminate states. The analytics system may assign the probability to the methylation state vector as a sum of the probabilities of the identified possibilities. As an example, the analytics system calculates a probability of a methylation state vector of $<M_1, I_2, U_3>$ as a sum of the probabilities for the possibilities of methylation state vectors of $<M_1, M_2, U_3>$ and $<M_1, U_2, U_3>$ since methylation states for CpG sites 1 and 3 are observed and in consensus with the fragment's methylation states at CpG sites 1 and 3. This method of summing out CpG sites with indeterminate states uses calculations of probabilities of possibilities up to $2^i$, wherein i denotes the number of indeterminate states in the methylation state vector. In additional embodiments, a dynamic programming algorithm may be implemented to calculate the probability of a methylation state vector with one or more indeterminate states. Advantageously, the dynamic programming algorithm operates in linear computational time.

In one embodiment, the computational burden of calculating probabilities and/or p-value scores may be further reduced by caching at least some calculations. For example, the analytic system may cache in transitory or persistent memory calculations of probabilities for possibilities of methylation state vectors (or windows thereof). If other fragments have the same CpG sites, caching the possibility probabilities allows for efficient calculation of p-value scores without needing to re-calculate the underlying possibility probabilities. Equivalently, the analytics system may calculate p-value scores for each of the possibilities of methylation state vectors associated with a set of CpG sites from vector (or window thereof). The analytics system may cache the p-value scores for use in determining the p-value scores of other fragments including the same CpG sites.

Generally, the p-value scores of possibilities of methylation state vectors having the same CpG sites may be used to determine the p-value score of a different one of the possibilities from the same set of CpG sites.

6.4.2.2. Sliding Window

In one embodiment, the analytics system uses 435 a sliding window to determine possibilities of methylation state vectors and calculate p-values. Rather than enumerating possibilities and calculating p-values for entire methylation state vectors, the analytics system enumerates possibilities and calculates p-values for only a window of sequential CpG sites, where the window is shorter in length (of CpG sites) than at least some fragments (otherwise, the window would serve no purpose). The window length may be static, user determined, dynamic, or otherwise selected.

In calculating p-values for a methylation state vector larger than the window, the window identifies the sequential set of CpG sites from the vector within the window starting from the first CpG site in the vector. The analytic system calculates a p-value score for the window including the first CpG site. The analytics system then "slides" the window to the second CpG site in the vector, and calculates another p-value score for the second window. Thus, for a window size l and methylation vector length m, each methylation state vector will generate m−l+1 p-value scores. After completing the p-value calculations for each portion of the vector, the lowest p-value score from all sliding windows is taken as the overall p-value score for the methylation state vector. In another embodiment, the analytics system aggregates the p-value scores for the methylation state vectors to generate an overall p-value score.

Using the sliding window helps to reduce the number of enumerated possibilities of methylation state vectors and their corresponding probability calculations that would otherwise need to be performed. Example probability calculations are shown in FIG. 5, but generally the number of possibilities of methylation state vectors increases exponentially by a factor of 2 with the size of the methylation state vector. To give a realistic example, it is possible for fragments to have upwards of 54 CpG sites. Instead of computing probabilities for $2^{54}$ (~$1.8\times10^{16}$) possibilities to generate a single p-score, the analytics system can instead use a window of size 5 (for example) which results in 50 p-value calculations for each of the 50 windows of the methylation state vector for that fragment. Each of the 50 calculations enumerates $2^5$ (32) possibilities of methylation state vectors, which total results in $50\times2^5$ ($1.6\times10^3$) probability calculations. This results in a vast reduction of calculations to be performed, with no meaningful hit to the accurate identification of anomalous fragments. This additional step can also be applied when validating 240 the control group with the validation group's methylation state vectors.

6.4.3. Analysis of Hyper or Hypomethylated Fragments

In some embodiments, an additional filtration step can be performed to identify genomic regions that can be targeted for detection of cancer, a cancer tissue of origin, or a type of cancer.

Figure 6:
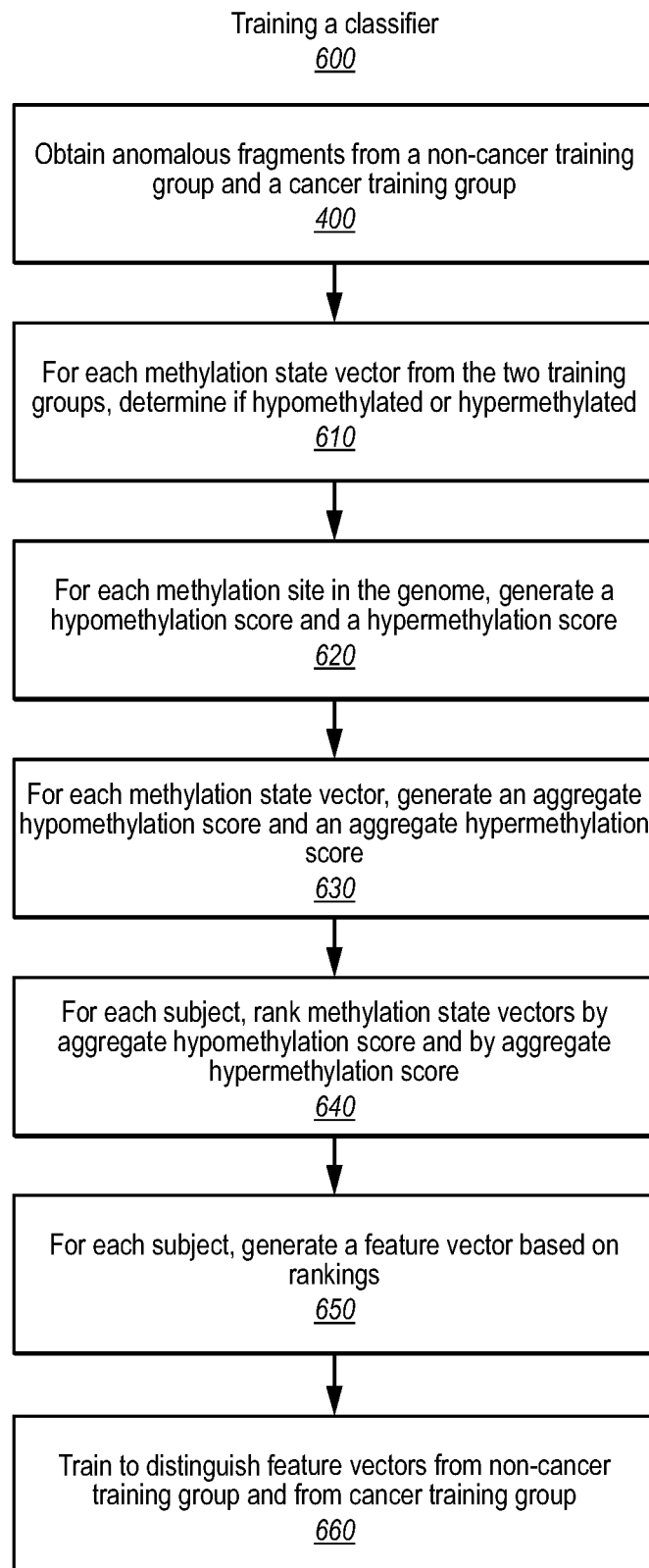
FIG. 6 is a flowchart describing a process of training a classifier based on the methylation statuses of fragments, according to an embodiment.

The analytics system may perform any variety and/or possibility of additional analyses with the set of anomalously methylated fragments. One additional analysis identifies 450 hypomethylated fragments or hypermethylated fragments from the filtered set. Fragments that are hypomethylated or hypermethylated can be defined as fragments of a certain length of CpG sites (e.g., more than 3, 4, 5, 6, 7, 8, 9, 10, etc.) with a high percentage of methylated CpG sites (e.g., more than 80%, 85%, 90%, or 95%, or any other percentage within the range of 50%-100%) or a high percentage of unmethylated CpG sites (e.g., more than 80%, 85%, 90%, or 95%, or any other percentage within the range of 50%-100%), respectively. FIG. 6, described below, illustrates an exemplary process for identifying these anomalously hypermethylated or hypomethylated portions of a genome based on the set of anomalously methylated fragments.

An alternate analysis applies 460 a trained classification model on the set of anomalous fragments. The trained classification model can be trained to identify any condition of interest that can be identified from the methylation state vectors. In one embodiment, the trained classification model is a binary classifier trained based on methylation states for cfDNA fragments obtained from a subject cohort with cancer, and optionally based on methylation states for cfDNA fragments obtained from a healthy subject cohort without cancer, and is then used to classify a test subject probability of having cancer, or not having cancer, based on anomalously methylation state vectors. In further embodiments, different classifiers may be trained using subject cohorts known to have particular cancer (e.g., breast, lung, prostrate, etc.) to predict whether a test subject has those specific cancers.

In one embodiment, the classifier is trained based on information about hyper/hypo methylated regions from the process 450 and as described with respect to FIG. 6 below.

FIG. 6 is a flowchart describing a process 600 of training a classifier based on methylation status of cfDNA fragments, according to an embodiment. An analytics system may be used to perform the process 600. The process accesses two training groups of samples—a non-cancer group and a cancer group—and obtains 400 a non-cancer set of methylation state vectors and a cancer set of methylation state vectors comprising the anomalous fragments of the samples in each group. The anomalous fragments may be identified according to the process of FIG. 4, for example.

The analytics system determines 610, for each methylation state vector, whether the methylation state vector is hypomethylated or hypermethylated. Here, the hypermethylated or hypomethylated label is assigned if at least some number of CpG sites have a particular state (methylated or unmethylated, respectively) and/or have a threshold percentage of sites that are the particular state (again, methylated or unmethylated, respectively). In one example, cfDNA fragments are identified as hypomethylated or hypermethylated, respectively, if the fragment overlaps at least 5 CpG sites, and at least 80%, 90% or 100% of its CpG sites are methylated or at least 80%, 90%, or 100% are unmethylated.

In an alternate embodiment, the analytics system considers portions of the methylation state vector and determines whether the portion is hypomethylated or hypermethylated, and may distinguish that portion to be hypomethylated or hypermethylated. This alternative resolves missing methylation state vectors which are large in size but contain at least one region of dense hypomethylation or hypermethylation. This process of defining hypomethylation and hypermethylation can be applied in step 450 of FIG. 4.

In one embodiment, the analytics system generates 620 a hypomethylation score ($P_{hypo}$) and a hypermethylation score ($P_{hyper}$) per CpG site in the genome. To generate either score at a given CpG site, the classifier takes four counts at that CpG site—(1) count of (methylations state) vectors of the cancer set labeled hypomethylated that overlap the CpG site; (2) count of vectors of the cancer set labeled hypermethylated that overlap the CpG site; (3) count of vectors of the non-cancer set labeled hypomethylated that overlap the CpG site; and (4) count of vectors of the non-cancer set labeled hypermethylated that overlap the CpG site. Additionally the process may normalize these counts for each group to account for variance in group size between the non-cancer group and the cancer group.

In one embodiment, the hypomethylation score at a given CpG site is defined as a log of a ratio of (1) over (3). Similarly the hypermethylation score is calculated as a log of a ratio of (2) over (4). Additionally these ratios may be calculated with an additional smoothing technique as discussed above.

In another embodiment, the hypomethylation score is defined as a ratio of (1) over (1) summed with (3). The hypermethylation score is defined as a ratio of (2) over (2) summed with (4). Similar to the embodiment above, smoothing techniques may be implemented into the ratios.

The analytics system generates 630 an aggregate hypomethylation score and an aggregate hypermethylation score for each anomalous methylation state vector. The aggregate hyper and hypo methylation scores, are determined based on the hyper and hypo methylation scores of the CpG sites in the methylation state vector. In one embodiment, the aggregate hyper and hypo methylation scores are assigned as the largest hyper and hypo methylation scores of the sites in each state vector, respectively. However, in alternate embodiments, the aggregate scores could be based on means, medians, or other calculations that use the hyper/hypo methylation scores of the sites in each vector. In one embodiment, the analytics system assigns the greater of the aggregate hypomethylation score and the aggregate hypermethylation score to the anomalous methylation state vector.

The analytics system then ranks 640 all of that subject's methylation state vectors by their aggregate hypomethylation score and by their aggregate hypermethylation score, resulting in two rankings per subject. The process selects aggregate hypomethylation scores from the hypomethylation ranking and aggregate hypermethylation scores from the hypermethylation ranking. With the selected scores, the classifier generates 650 a single feature vector for each subject. In one embodiment, the scores selected from either ranking are selected with a fixed order that is the same for each generated feature vector for each subject in each of the training groups. As an example, in one embodiment the classifier selects the first, the second, the fourth, the eighth, the sixteenth, the thirty-second, and the sixty-fourth aggregate hyper methylation score, and similarly for each aggregate hypo methylation score, from each ranking and writes those scores in the feature vector for that subject (totaling 14 features in the feature vector). In additional embodiments, to adjust for sample sequencing depth, the analytics system adjusts ranks in linear proportion to relative sample depth. For example, if the relative sample depth was x, interpolated scores were taken at x*the original ranks (i.e. x=1.1, we take scores computed at ranks 1.1, 2.2, ..., x*2i). The analytics system may then define the feature vector based on the adjusted ranks to be used in further classification.

The analytics system trains 660 a binary classifier to distinguish feature vectors between the cancer and non-cancer training groups. The analytics system may group the training samples into sets of one or more training samples for iterative batch training of the binary classifier. After inputting all sets of training samples including their training feature vectors and adjusting the classification parameters, the binary classifier is sufficiently trained to label test samples according to their feature vector within some margin of error.

In one embodiment, the classifier is a non-linear classifier. In a specific embodiment, the classifier is a non-linear classifier utilizing a L2-regularized kernel logistic regression with a Gaussian radial basis function (RBF) kernel. Specifically, a regularized kernel logistic regression classifier (KLR) was trained using the isotropic radial basis function (power exponential 2) as the kernel with scale parameter gamma and L2 regularization parameter lambda. Gamma and lambda were optimized for holdout log-loss using internal cross-validation within specified training data, and were optimized using grid-search in multiplicative steps, starting at the maximum value and halving the parameter each step. In other embodiments, the classifier can include other types of classifiers, such as a random forest classifier, a mixture model, a convolutional neural network, or an autoencoder model.

In some embodiments, calculation is performed with respect to each CpG site. Specifically a first count is determined that is the number of cancerous samples (cancer_count) that include a fragment overlapping that CpG, and a second count is determined that is the total number of samples containing fragments overlapping that CpG (total) in the set. Genomic regions can be selected based on the numbers, for example, based on criteria positively correlated to the number of cancerous samples (cancer_count) that include a fragment overlapping that CpG, and inversely correlated to the total number of samples containing fragments overlapping that CpG (total) in the set. Specifically, in one embodiment, the number of non-cancer samples ($n_{non-cancer}$) and the number of cancer samples ($n_{cancer}$) having a fragment overlapping a CpG site are counted. Then the probability that a sample is cancer is estimated as $(n_{cancer}+1)/(n_{cancer}+n_{non-cancer}+2)$. CpG sites by this metric were ranked and greedily added to a panel until the panel size budget is exhausted.

In some cases, additional analysis calculates the log-odds ratio that the anomalous fragments from a subject are indicative of cancer generally. The log-odds ratio can be calculated by taking the log of a ratio of a probability of being cancerous over a probability of being non-cancerous (i.e., one minus the probability of being cancerous), both as determined by the applied classification model.

6.4.4. Off-Target Genomic Regions

In some embodiments, probes targeting selected genomic regions are further filtered 465 based on the number of their off-target regions. This is for screening probes that pull down too many cfDNA fragments containing off-target genomic regions. Exclusion of probes having many off-target regions can be valuable by decreasing off-target rates and increasing target coverage for a given amount of sequencing.

An off-target genomic region is a genomic region that has sufficient homology to a target genomic region to be bound and pulled down by a probe designed to target the target genomic region. An off-target genomic region can be a genomic region (or a converted sequence of that same region) that aligns to a probe along at least 35 bp, 40 bp, 45 bp, 50 bp, 60 bp, 70 bp, or 80 bp with at least an 80%, 85%, 90%, 95%, or 97% match rate. In one embodiment, an off-target genomic region is a genomic region (or a converted sequence of that same region) that aligns to a probe along at least 45 bp with at least a 90% match rate. Various methods known in the art can be adopted to screen off-target genomic regions.

Exhaustively searching the genome to find all off-target genomic regions can be computationally challenging. In one embodiment, a k-mer seeding strategy (which can allow one or more mismatches) is combined to local alignment at the seed locations. In this case, exhaustive searching of good alignments can be guaranteed based on k-mer length, number of mismatches allowed, and number of k-mer seed hits at a particular location. This requires doing dynamic programing local alignment at a large number of locations, so this approach is highly optimized to use vector CPU instructions (e.g., AVX2, AVX512) and also can be parallelized across many cores within a machine and also across many machines connected by a network. A person of ordinary skill will recognize that modifications and variations of this approach can be implemented for the purpose of identifying off-target genomic regions.

In some embodiments, probes having off-target genomic regions more than a threshold number are excluded. For example, probes having more than 30, more than 25, more than 20, more than 18, more than 15, more than 12, more than 10, or more than 5 are excluded.

In some embodiments, probes are divided into 2, 3, 4, 5, 6, or more separate groups depending on the numbers of off-target regions. For example, probes having no off-target regions are assigned to high-quality group, probes having 1-19 off-target regions are assigned to low-quality group, and probes having more than 19 off-target regions are assigned to poor-quality group. Other cut-off values can be used for the grouping.

In some embodiments, probes in the lowest quality group are excluded. In some embodiments, probes in groups other than the highest-quality group are excluded. In some embodiments, separate panels are made for the probes in each group. In some embodiments, all the probes are put on the same panel, but separate analysis is performed based on the assigned groups.

In some embodiments, a panel comprises a larger number of high-quality probes than the number of probes in lower groups. In some embodiments, a panel comprises a smaller number of poor-quality probes than the number of probes in other group. In some embodiments, more than 95%, 90%, 85%, 80%, 75%, or 70% of probes in a panel are high-quality probes. In some embodiments, less than 35%, 30%, 20%, 10%, 5%, 4%, 3%, 2% or 1% of the probes in a panel are low-quality probes. In some embodiments, less than 5%, 4%, 3%, 2% or 1% of the probes in a panel are poor-quality probes. In some embodiments, no poor-quality probes are included in a panel.

In some embodiments, probes having below 50%, below 40%, below 30%, below 20%, below 10% or below 5% are excluded. In some embodiments, probes having above 30%, above 40%, above 50%, above 60%, above 70%, above 80%, or above 90% are selectively included in a panel.

6.5. Methods of Using Cancer Assay Panel

In yet another aspect, methods of using a cancer assay panel are provided. The methods can comprise steps of bisulfite treatment cfDNA fragments to convert unmethylated cytosines to uracils, applying the samples to the cancer assay panel and sequencing cfDNA fragments that bind to the probes in the panel. The sequence reads can be further compared to a reference genome. This assay can allow identification of methylation states at CpG sites within the fragments and thus provide information relevant to diagnosis of cancer.

6.5.1. Sample Processing

Figure 7A:
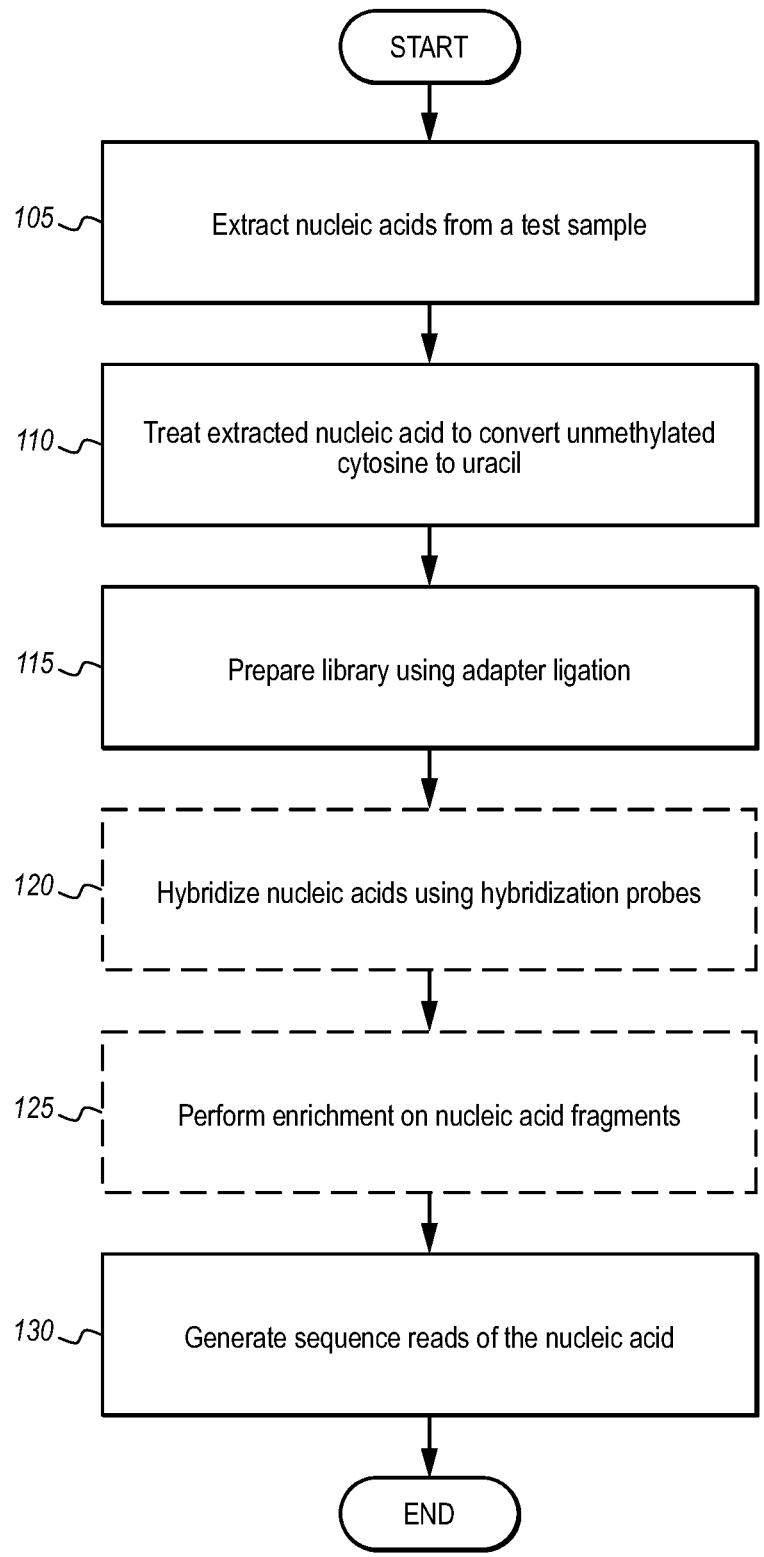
FIG. 7A is a flowchart describing a process of sequencing a fragment of cell-free DNA (cfDNA), according to an embodiment.

FIG. 7A is a flowchart of a method for preparing a nucleic acid sample for analysis according to one embodiment. The method includes, but is not limited to, the following steps. For example, any step of the method may comprise a quantitation sub-step for quality control or other laboratory assay procedures known to one skilled in the art.

In step 105, a nucleic acid sample (DNA or RNA) is extracted from a subject. In the present disclosure, DNA and RNA may be used interchangeably unless otherwise indicated. That is, the embodiments described herein may be applicable to both DNA and RNA types of nucleic acid sequences. However, the examples described herein may focus on DNA for purposes of clarity and explanation. The sample may be any subset of the human genome, including the whole genome. The sample may include blood, plasma, serum, urine, fecal, saliva, other types of bodily fluids, or any combination thereof. In some embodiments, methods for drawing a blood sample (e.g., syringe or finger prick) may be less invasive than procedures for obtaining a tissue biopsy, which may require surgery. The extracted sample may comprise cfDNA and/or ctDNA. For healthy individuals, the human body may naturally clear out cfDNA and other cellular debris. If a subject has a cancer or disease, cfDNA or ctDNA in an extracted sample may be present at a detectable level for diagnosis.

In step 110, the cfDNA fragments are treated to convert unmethylated cytosines to uracils. In one embodiment, the method uses a bisulfite treatment of the DNA which converts the unmethylated cytosines to uracils without converting the methylated cytosines. For example, a commercial kit such as the EZ DNA Methylation™—Gold, EZ DNA Methylation™—Direct or an EZ DNA Methylation™—Lightning kit (available from Zymo Research Corp (Irvine, Calif.)) is used for the bisulfite conversion. In another embodiment, the conversion of unmethylated cytosines to uracils is accomplished using an enzymatic reaction. For example, the conversion can use a commercially available kit for conversion of unmethylated cytosines to uracils, such as APOBEC-Seq (NEBiolabs, Ipswich, Mass.).

In step 115, a sequencing library is prepared. In a first step, a ssDNA adapter is added to the 3'-OH end of a bisulfite-converted ssDNA molecule using a ssDNA ligation reaction. In one embodiment, the ssDNA ligation reaction uses CircLigase II (Epicentre) to ligate the ssDNA adapter to the 3'-OH end of a bisulfite-converted ssDNA molecule, wherein the 5'-end of the adapter is phosphorylated and the bisulfite-converted ssDNA has been dephosphorylated (i.e., the 3' end has a hydroxyl group). In another embodiment, the ssDNA ligation reaction uses Thermostable 5' AppDNA/RNA ligase (available from New England BioLabs (Ipswich, Mass.)) to ligate the ssDNA adapter to the 3'-OH end of a bisulfite-converted ssDNA molecule. In this example, the first UMI adapter is adenylated at the 5'-end and blocked at the 3'-end. In another embodiment, the ssDNA ligation reaction uses a T4 RNA ligase (available from New England BioLabs) to ligate the ssDNA adapter to the 3'-OH end of a bisulfite-converted ssDNA molecule. In a second step, a second strand DNA is synthesized in an extension reaction. For example, an extension primer, that hybridizes to a primer sequence included in the ssDNA adapter, is used in a primer extension reaction to form a double-stranded bisulfate-converted DNA molecule. Optionally, in one embodiment, the extension reaction uses an enzyme that is able to read through uracil residues in the bisulfate-converted template strand. Optionally, in a third step, a dsDNA adapter is added to the double-stranded bisulfate-converted DNA molecule. Finally, the double-stranded bisulfate-converted DNA is amplified to add sequencing adapters. For example, PCR amplification using a forward primer that includes a P5 sequence and a reverse primer that includes a P7 sequence is used to add P5 and P7 sequences to the bisulfate-converted DNA. Optionally, during library preparation, unique molecular identifiers (UMI) may be added to the nucleic acid molecules (e.g., DNA molecules) through adapter ligation. The UMIs are short nucleic acid sequences (e.g., 4-10 base pairs) that are added to ends of DNA fragments during adapter ligation. In some embodiments, UMIs are degenerate base pairs that serve as a unique tag that can be used to identify sequence reads originating from a specific DNA fragment. During PCR amplification following adapter ligation, the UMIs are replicated along with the attached DNA fragment, which provides a way to identify sequence reads that came from the same original fragment in downstream analysis.

In step 120, targeted DNA sequences may be enriched from the library. This is used, for example, where a targeted panel assay is being performed on the samples. During enrichment, hybridization probes (also referred to herein as "probes") are used to target, and pull down, nucleic acid fragments informative for the presence or absence of cancer (or disease), or cancer status. For a given workflow, the probes may be designed to anneal (or hybridize) to a target (complementary) strand of DNA or RNA. The target strand may be the "positive" strand (e.g., the strand transcribed into mRNA, and subsequently translated into a protein) or the complementary "negative" strand. The probes may range in length from 10s, 100s, or 1000s of base pairs. Moreover, the probes may cover overlapping portions of a target region.

After a hybridization step 120, the hybridized nucleic acid fragments are captured and may also be amplified using PCR (enrichment 125). For example, the target sequences can be enriched to obtain enriched sequences that can be subsequently sequenced. In general, any known method in the art can be used to isolate, and enrich for, probe-hybridized target nucleic acids. For example, as is well known in the art, a biotin moiety can be added to the 5'-end of the probes (i.e., biotinylated) to facilitate isolation of target nucleic acids hybridized to probes using a streptavidin-coated surface (e.g., streptavidin-coated beads).

In step 130, sequence reads are generated from the enriched DNA sequences, e.g., enriched sequences. Sequencing data may be acquired from the enriched DNA sequences by known means in the art. For example, the method may include next generation sequencing (NGS) techniques including synthesis technology (Illumina), pyro-sequencing (454 Life Sciences), ion semiconductor technology (Ion Torrent sequencing), single-molecule real-time sequencing (Pacific Biosciences), sequencing by ligation (SOLiD sequencing), nanopore sequencing (Oxford Nanopore Technologies), or paired-end sequencing. In some embodiments, massively parallel sequencing is performed using sequencing-by-synthesis with reversible dye terminators.

6.5.2. Analysis of Sequence Reads

In some embodiments, the sequence reads may be aligned to a reference genome using known methods in the art to determine alignment position information. The alignment position information may indicate a beginning position and an end position of a region in the reference genome that corresponds to a beginning nucleotide base and end nucleotide base of a given sequence read. Alignment position information may also include sequence read length, which can be determined from the beginning position and end position. A region in the reference genome may be associated with a gene or a segment of a gene.

In various embodiments, a sequence read is comprised of a read pair denoted as $R_1$ and $R_2$. For example, the first read $R_1$ may be sequenced from a first end of a nucleic acid fragment whereas the second read $R_2$ may be sequenced from the second end of the nucleic acid fragment. Therefore, nucleotide base pairs of the first read $R_1$ and second read $R_2$ may be aligned consistently (e.g., in opposite orientations) with nucleotide bases of the reference genome. Alignment position information derived from the read pair $R_1$ and $R_2$ may include a beginning position in the reference genome that corresponds to an end of a first read (e.g., $R_1$) and an end position in the reference genome that corresponds to an end of a second read (e.g., $R_2$). In other words, the beginning position and end position in the reference genome represent the likely location within the reference genome to which the nucleic acid fragment corresponds. In one embodiment, the read pair $R_1$ and $R_2$ can be assembled into a fragment, and the fragment used for subsequent analysis and/or classification. An output file having SAM (sequence alignment map) format or BAM (binary alignment map) format may be generated and output for further analysis.

From the sequence reads, the location and methylation state for each of CpG site may be determined based on alignment to a reference genome. Further, a methylation state vector for each fragment may be generated specifying a location of the fragment in the reference genome (e.g., as specified by the position of the first CpG site in each fragment, or another similar metric), a number of CpG sites in the fragment, and the methylation state of each CpG site in the fragment whether methylated (e.g., denoted as M), unmethylated (e.g., denoted as U), or indeterminate (e.g., denoted as I). The methylation state vectors may be stored in temporary or persistent computer memory for later use and processing. Further, duplicate reads or duplicate methylation state vectors from a single subject may be removed. In an additional embodiment, it may be determined that a certain fragment has one or more CpG sites that have an indeterminate methylation status. Such fragments may be excluded from later processing or selectively included where downstream data model accounts for such indeterminate methylation statuses.

Figure 7B:
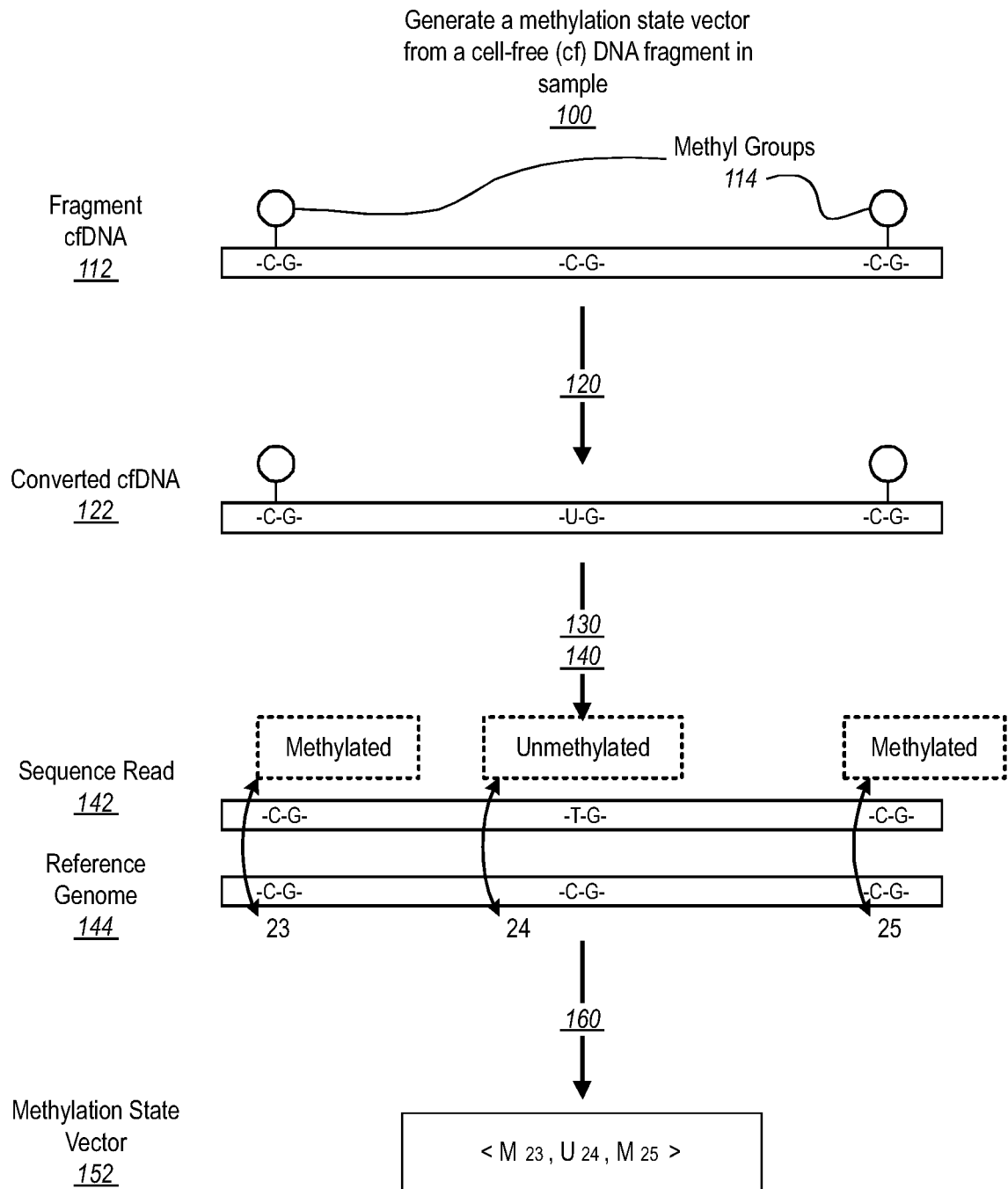
FIG. 7B is an illustration of the process of FIG. 7A of sequencing a fragment of cfDNA to obtain a methylation state vector (e.g., a methylation state for the fragment), according to an embodiment.

FIG. 7B is an illustration of the process 100 of FIG. 7A of sequencing a cfDNA fragment to obtain a methylation state vector, according to an embodiment. As an example, the analytics system takes a cfDNA fragment 112. In this example, the cfDNA fragment 112 contains three CpG sites. As shown, the first and third CpG sites of the cfDNA fragment 112 are methylated 114. During the treatment step 120, the cfDNA fragment 112 is converted to generate a converted cfDNA fragment 122. During the treatment 120, the second CpG site which was unmethylated has its cytosine converted to uracil. However, the first and third CpG sites are not converted.

After conversion, a sequencing library 130 is prepared and sequenced 140 generating a sequence read 142. The analytics system aligns 150 the sequence read 142 to a reference genome 144. The reference genome 144 provides the context as to what position in a human genome the fragment cfDNA originates from. In this simplified example, the analytics system aligns 150 the sequence read such that the three CpG sites correlate to CpG sites 23, 24, and 25 (arbitrary reference identifiers used for convenience of description). The analytics system thus generates information both on methylation status of all CpG sites on the cfDNA fragment 112 and which to position in the human genome the CpG sites map. As shown, the CpG sites on sequence read 142 which were methylated are read as cytosines. In this example, the cytosines appear in the sequence read 142 only in the first and third CpG site which allows one to infer that the first and third CpG sites in the original cfDNA fragment were methylated. Whereas, the second CpG site is read as a thymine (U is converted to T during the sequencing process), and thus, one can infer that the second CpG site was unmethylated in the original cfDNA fragment. With these two pieces of information, the methylation status and location, the analytics system generates 160 a methylation state vector 152 for the fragment cfDNA 112. In this example, the resulting methylation state vector 152 is $<M_{23}, U_{24}, M_{25}>$, wherein M corresponds to a methylated CpG site, U corresponds to an unmethylated CpG site, and the subscript number corresponds to a position of each CpG site in the reference genome.

FIGS. 9A & 9B show three graphs of data validating the consistency of sequencing from a control group. The first graph 170 shows conversion accuracy of conversion of unmethylated cytosines to uracil (step 120) on cfDNA fragment obtained from a test sample across subjects in varying stages of cancer—stage I, stage II, stage III, stage IV, and non-cancer. As shown, there was uniform consistency in converting unmethylated cytosines on cfDNA fragments into uracils. There was an overall conversion accuracy of 99.47% with a precision at ±0.024%. The second graph 180 shows mean coverage over varying stages of cancer. The mean coverage over all groups being ~34× mean across the genome coverage of DNA fragments, using only those confidently mapped to the genome are counted. The third graph 190 shows concentration of cfDNA per sample across varying stages of cancer.

6.5.3. Detection of Cancer

Sequence reads or fragments obtained by the methods provided herein can be analyzed by a medical professional, or further processed by an automated algorithms. For example, the analytics system is used to receive sequencing data from a sequencer and perform various aspects of processing as described herein. The analytics system can be one of a personal computer (PC), a desktop computer, a laptop computer, a notebook, a tablet PC, a mobile device. A computing device can be communicatively coupled to the sequencer through a wireless, wired, or a combination of wireless and wired communication technologies. Generally, the computing device is configured with a processor and memory storing computer instructions that, when executed by the processor, cause the processor to perform steps as described in the remainder of this document. Generally, the amount of genetic data and data derived therefrom is sufficiently large, and the amount of computational power required so great, so as to be impossible to be performed on paper or by the human mind alone.

The clinical interpretation of methylation status of targeted genomic regions is a process that includes classifying the clinical effect of each or a combination of the methylation status and reporting the results in ways that are meaningful to a medical professional. The clinical interpretation can be based on comparison of the sequence reads with a database specific to cancer or non-cancer subjects, and/or based on numbers and types of the cfDNA fragments having cancer-specific methylation patterns identified from a sample. In some embodiments, targeted genomic regions are ranked or classified based on their likeness to be differentially methylated in cancer samples, and the ranks or classifications are used in the interpretation process. The ranks and classifications can include (1) the type of clinical effect, (2) the strength of evidence of the effect, and (3) the size of the effect. Various methods for clinical analysis and interpretation of genome data can be adopted for analysis of the sequence reads. In some other embodiments, the clinical interpretation of the methylation states of such differentially methylated regions can be based on machine learning approaches that interpret a current sample based on a classification or regression method that was trained using the methylation states of such differentially methylated regions from samples from cancer and non-cancer patients with known cancer status, cancer type, cancer stage, tissue of origin, etc.

The clinically meaningful information can include the presence or absence of cancer generally, presence or absence of certain types of cancers, cancer stage, or presence or absence of other types of diseases. In some embodiments, the information relates to a presence or absence of one or more cancer types, selected from the group consisting of anorectal cancer, bladder and urothelial cancer, blood cancer, breast cancer (hormone receptor positive and hormone receptor negative), biliary tract cancer, cervical cancer, colorectal cancer, endometrial cancer, esophageal cancer, head and neck cancer, gastric cancer, hepatobiliary cancer, liver cancer, lung cancer, lymphoid neoplasm, gall bladder cancer, melanoma, multiple myeloma, ovarian cancer, pancreatic cancer, upper GI tract cancer, prostate cancer, renal cancer, sarcoma, thyroid cancer, bile duct cancer, urothelial cancer, and uterine cancer.

Cancer Classifier

To train a cancer type classifier, the analytics system obtains a plurality of training samples each having a set of hypomethylated and hypermethylated fragments indicative of cancer, e.g., identified via step 450 in the process 400, and a label of the training sample's cancer type. The analytics system determines, for each training sample, a feature vector based on the set of hypomethylated and hypermethylated fragments indicative of cancer. The analytics system calculates an anomaly score for each CpG site in the targeted genomic regions. In one embodiment, the analytics system defines the anomaly score for the feature vector as a binary scoring based on whether there is a hypomethylated or hypermethylated fragment from the set that encompasses the CpG site. Once all anomaly scores are determined for a training sample, the analytics system determines the feature vector as a vector of elements including, for each element, one of the anomaly scores associated with one of the CpG sites. The analytics system may normalize the anomaly scores of the feature vector based on a coverage of the sample, i.e., a median or average sequencing depth over all CpG sites.

With the feature vectors of the training samples, the analytics system can train the cancer classifier. In one embodiment, the analytics system trains a binary cancer classifier to distinguish between the labels, cancer and non-cancer, based on the feature vectors of the training samples. In this embodiment, the classifier outputs a prediction score indicating the likelihood of the presence or absence of cancer. In another embodiment, the analytics system trains a multiclass cancer classifier to distinguish between many cancer types (e.g., between head and neck cancer, liver/bileduct cancer, upper GI cancer, pancreatic/gallbladder cancer; colorectal cancer, ovarian cancer, lung cancer, multiple myeloma, lymphoid neoplasms, melanoma, sarcoma, breast cancer, and uterine cancer). In this multiclass cancer classifier embodiment, the cancer classifier is trained to determine a cancer prediction that comprises a prediction value for each of the cancer types being classified for. The prediction values may correspond to a likelihood that a given sample has each of the cancer types. For example, the cancer classifier returns a cancer prediction including a prediction value for breast cancer, lung cancer, and non-cancer. For example, the cancer classifier may return a cancer prediction for a test sample including a prediction score for breast cancer, lung cancer, and/or no cancer. In either embodiment, the analytics system trains the cancer classifier by inputting sets of training samples with their feature vectors into the cancer classifier and adjusting classification parameters so that a function of the classifier accurately relates the training feature vectors to their corresponding label. The analytics system may group the training samples into sets of one or more training samples for iterative batch training of the cancer classifier. After inputting all sets of training samples including their training feature vectors and adjusting the classification parameters, the cancer classifier is sufficiently trained to label test samples according to their feature vector within some margin of error. The analytics system may train the cancer classifier according to any one of a number of methods. As an example, the binary cancer classifier may be a L2-regularized logistic regression classifier that is trained using a log-loss function. As another example, the multi-cancer classifier may be a multinomial logistic regression. In practice either type of cancer classifier may be trained using other techniques. These techniques are numerous including potential use of kernel methods, machine learning algorithms such as multilayer neural networks, etc. In particular, methods as described in PCT/US2019/022122 and U.S. patent application Ser. No. 16/352,602 which are incorporated by reference in their entireties herein can be used for various embodiments.

In particular embodiments, a cancer classifier is trained by the process comprising the steps of: a. obtaining sequence information of training fragments from a plurality of training subjects; b. for each training fragment, determining whether that training fragment is hypomethylated or hypermethylated, wherein each of the hypomethylated and hypermethylated training fragments comprises at least a threshold number of CpG sites with at least a threshold percentage of the CpG sites being unmethylated or methylated, respectively, c. for each training subject, generating a training feature vector based on the hypomethylated training fragments and hypermethylated training fragments, and d. training the model with the training feature vectors from the one or more training subjects without cancer and the training feature vectors from the one or more training subjects with cancer. The training method can further comprise the steps of: a. obtaining sequence information of training fragments from a plurality of training subjects; b. for each training fragment, determining whether that training fragment is hypomethylated or hypermethylated, wherein each of the hypomethylated and hypermethylated training fragments comprises at least a threshold number of CpG sites with at least a threshold percentage of the CpG sites being unmethylated or methylated, respectively, c. for each of a plurality of CpG sites in a reference genome: quantifying a count of hypomethylated training fragments which overlap the CpG site and a count of hypermethylated training fragments which overlap the CpG site; and generating a hypomethylation score and a hypermethylation score based on the count of hypomethylated training fragments and hypermethylated training fragments; d. for each training fragment, generating an aggregate hypomethylation score based on the hypomethylation score of the CpG sites in the training fragment and an aggregate hypermethylation score based on the hypermethylation score of the CpG sites in the training fragment; e. for each training subject: ranking the plurality of training fragments based on aggregate hypomethylation score and ranking the plurality of training fragments based on aggregate hypermethylation score; and generating a feature vector based on the ranking of the training fragments; f. obtaining training feature vectors for one or more training subjects without cancer and training feature vectors for the one or more training subjects with cancer; and g. training the model with the feature vectors for the one or more training subjects without cancer and the feature vectors for the one or more training subjects with cancer. In some embodiments, the model comprises one of a kernel logistic regression classifier, a random forest classifier, a mixture model, a convolutional neural network, and an autoencoder model.

In some embodiments, quantifying a count of hypomethylated training fragments which overlap that CpG site and a count of hypermethylated training fragments which overlap that CpG site further comprises: a. quantifying a cancer count of hypomethylated training fragments from the one or more training subjects with cancer that overlap that CpG site and a non-cancer count of hypomethylated training fragments from the one or more training subjects without cancer that overlap that CpG site; and b. quantifying a cancer count of hypermethylated training fragments from the one or more training subjects with cancer that overlap that CpG site and a non-cancer count of hypermethylated training fragments from the one or more training subjects without cancer that overlap that CpG site. In some embodiments, generating a hypomethylation score and a hypermethylation score based on the count of hypomethylated training fragments and hypermethylated training fragments further comprises: a. for generating the hypomethylation score, calculating a hypomethylation ratio of the cancer count of hypomethylated training fragments over a hypomethylation sum of the cancer count of hypomethylated training fragments and the non-cancer count of hypomethylated training fragments; and b. for generating the hypermethylation score, calculating a hypermethylation ratio of the cancer count of hypermethylated training fragments over a hypermethylation sum of the cancer count of hypermethylated training fragments and the non-cancer count of hypermethylated training fragments.

During deployment, the analytics system obtains sequence reads from a test sample collected from a subject. Various sequencing methods available in the art can be used to obtain sequence reads. In some embodiments, the sequence reads are obtained from whole genome sequencing or targeted sequencing. In some embodiments, the sequence reads include a set of sequence reads of modified test fragments, wherein the modified test fragments are obtained by processing a set of nucleic acid fragments, wherein each of the nucleic acid fragments corresponds to or is derived from a plurality of genomic regions selected from any one of Lists 1-8. In some embodiments, the sequence reads are from the DNA samples enriched using the assay panel described herein.

The analytics system processes the sequence reads to obtain a test feature vector in a similar process as described for the training samples. In some embodiments, the test feature vector is obtained by the process comprising a. for each of the nucleic acid fragments, determining whether the nucleic acid fragment is hypomethylated or hypermethylated, wherein each of the hypomethylated and hypermethylated nucleic acid fragments comprises at least a threshold number of CpG sites with at least a threshold percentage of the CpG sites being unmethylated or methylated, respectively; b. for each of a plurality of CpG sites in a reference genome: quantifying a count of hypomethylated nucleic acid fragments which overlap the CpG site and a count of hypermethylated nucleic acid fragments which overlap the CpG site; and generating a hypomethylation score and a hypermethylation score based on the count of hypomethylated nucleic acid fragments and hypermethylated nucleic acid fragments; c. for each nucleic acid fragment, generating an aggregate hypomethylation score based on the hypomethylation score of the CpG sites in the nucleic acid fragment and an aggregate hypermethylation score based on the hypermethylation score of the CpG sites in the nucleic acid fragment; d. ranking the plurality of nucleic acid fragments based on aggregate hypomethylation score and ranking the plurality of nucleic fragments based on aggregate hypermethylation score; and e. generating the test feature vector based on the ranking of the nucleic acid fragments.

The analytics system then inputs the test feature vector into the trained cancer classifier to yield a cancer prediction, e.g., binary prediction (cancer or non-cancer) or multiclass cancer prediction (prediction score for each of a plurality of cancer types). In some embodiments, the analytics system outputs a cancer probability for the test sample. The cancer probability can be compared to a threshold probability to determine whether the test sample is from a subject with cancer or without cancer.

Exemplary Sequencer and Analytics System

FIG. 8A is a flowchart of systems and devices for sequencing nucleic acid samples according to one embodiment. This illustrative flowchart includes devices such as a sequencer 820 and an analytics system 800. The sequencer 820 and the analytics system 800 may work in tandem to perform one or more steps in the processes described herein.

In various embodiments, the sequencer 820 receives an enriched nucleic acid sample 810. As shown in FIG. 8A, the sequencer 820 can include a graphical user interface 825 that enables user interactions with particular tasks (e.g., initiate sequencing or terminate sequencing) as well as one more loading stations 830 for loading a sequencing cartridge including the enriched fragment samples and/or for loading necessary buffers for performing the sequencing assays. Therefore, once a user of the sequencer 820 has provided the necessary reagents and sequencing cartridge to the loading station 830 of the sequencer 820, the user can initiate sequencing by interacting with the graphical user interface 825 of the sequencer 820. Once initiated, the sequencer 820 performs the sequencing and outputs the sequence reads of the enriched fragments from the nucleic acid sample 810.

In some embodiments, the sequencer 820 is communicatively coupled with the analytics system 800. The analytics system 800 includes some number of computing devices used for processing the sequence reads for various applications such as assessing methylation status at one or more CpG sites, variant calling or quality control. The sequencer 820 may provide the sequence reads in a BAM file format to the analytics system 800. The analytics system 800 can be communicatively coupled to the sequencer 820 through a wireless, wired, or a combination of wireless and wired communication technologies. Generally, the analytics system 800 is configured with a processor and non-transitory computer-readable storage medium storing computer instructions that, when executed by the processor, cause the processor to process the sequence reads or to perform one or more steps of any of the methods or processes disclosed herein.

In some embodiments, the sequence reads may be aligned to a reference genome using known methods in the art to determine alignment position information, e.g., part of step 140 of the process 100 in FIG. 3A. Alignment position may generally describe a beginning position and an end position of a region in the reference genome that corresponds to a beginning nucleotide based and an end nucleotide base of a given sequence read. Corresponding to methylation sequencing, the alignment position information may be generalized to indicate a first CpG site and a last CpG site included in the sequence read according to the alignment to the reference genome. The alignment position information may further indicate methylation statuses and locations of all CpG sites in a given sequence read. A region in the reference genome may be associated with a gene or a segment of a gene; as such, the analytics system 800 may label a sequence read with one or more genes that align to the sequence read. In one embodiment, fragment length (or size) is determined from the beginning and end positions.

In various embodiments, for example when a paired-end sequencing process is used, a sequence read is comprised of a read pair denoted as R_1 and R_2. For example, the first read R_1 may be sequenced from a first end of a double-stranded DNA (dsDNA) molecule whereas the second read R_2 may be sequenced from the second end of the double-stranded DNA (dsDNA). Therefore, nucleotide base pairs of the first read R_1 and second read R_2 may be aligned consistently (e.g., in opposite orientations) with nucleotide bases of the reference genome. Alignment position information derived from the read pair R_1 and R_2 may include a beginning position in the reference genome that corresponds to an end of a first read (e.g., R_1) and an end position in the reference genome that corresponds to an end of a second read (e.g., R_2). In other words, the beginning position and end position in the reference genome represent the likely location within the reference genome to which the nucleic acid fragment corresponds. In one embodiment, the read pair $R_1$ and $R_2$ can be assembled into a fragment, and the fragment used for subsequent analysis and/or classification. An output file having SAM (sequence alignment map) format or BAM (binary) format may be generated and output for further analysis.

Referring now to FIG. 8B, FIG. 8B is a block diagram of an analytics system 800 for processing DNA samples according to one embodiment. The analytics system implements one or more computing devices for use in analyzing DNA samples. The analytics system 800 includes a sequence processor 840, sequence database 845, model database 855, models 850, parameter database 865, and score engine 860. In some embodiments, the analytics system 800 performs one or more steps in the processes 100 of FIG. 3A, 340 of FIG. 3B, 400 of FIG. 4, 500 of FIG. 5, 600 of FIG. 6A, or 680 of FIG. 6B and other process described herein.

The sequence processor 840 generates methylation state vectors for fragments from a sample. At each CpG site on a fragment, the sequence processor 840 generates a methylation state vector for each fragment specifying a location of the fragment in the reference genome, a number of CpG sites in the fragment, and the methylation state of each CpG site in the fragment whether methylated, unmethylated, or indeterminate via the process 100 of FIG. 3A. The sequence processor 840 may store methylation state vectors for fragments in the sequence database 845. Data in the sequence database 845 may be organized such that the methylation state vectors from a sample are associated to one another.

Further, multiple different models 850 may be stored in the model database 855 or retrieved for use with test samples. In one example, a model is a trained cancer classifier for determining a cancer prediction for a test sample using a feature vector derived from anomalous fragments. The training and use of the cancer classifier is discussed elsewhere herein. The analytics system 800 may train the one or more models 850 and store various trained parameters in the parameter database 865. The analytics system 800 stores the models 850 along with functions in the model database 855.

During inference, the score engine 860 uses the one or more models 850 to return outputs. The score engine 860 accesses the models 850 in the model database 855 along with trained parameters from the parameter database 865. According to each model, the score engine receives an appropriate input for the model and calculates an output based on the received input, the parameters, and a function of each model relating the input and the output. In some use cases, the score engine 860 further calculates metrics correlating to a confidence in the calculated outputs from the model. In other use cases, the score engine 860 calculates other intermediary values for use in the model.

Application

In some embodiments, the methods, analytic systems and/or classifier of the present invention can be used to detect the presence (or absence) of cancer, monitor cancer progression or recurrence, monitor therapeutic response or effectiveness, determine a presence or monitor minimum residual disease (MRD), or any combination thereof. In some embodiments, the analytic systems and/or classifier may be used to identify the tissue or origin for a cancer. For instance, the systems and/or classifiers may be used to identify a cancer as of any of the following cancer types: head and neck cancer, liver/bileduct cancer, upper GI cancer, pancreatic/gallbladder cancer; colorectal cancer, ovarian cancer, lung cancer, multiple myeloma, lymphoid neoplasms, melanoma, sarcoma, breast cancer, and uterine cancer. For example, as described herein, a classifier can be used to generate a likelihood or probability score (e.g., from 0 to 100) that a sample feature vector is from a subject with cancer. In some embodiments, the probability score is compared to a threshold probability to determine whether or not the subject has cancer. In other embodiments, the likelihood or probability score can be assessed at different time points (e.g., before or after treatment) to monitor disease progression or to monitor treatment effectiveness (e.g., therapeutic efficacy). In still other embodiments, the likelihood or probability score can be used to make or influence a clinical decision (e.g., diagnosis of cancer, treatment selection, assessment of treatment effectiveness, etc.). For example, in one embodiment, if the likelihood or probability score exceeds a threshold, a physician can prescribe an appropriate treatment.

Early Detection of Cancer

In some embodiments, the methods and/or classifier of the present invention are used to detect the presence or absence of cancer in a subject suspected of having cancer. For example, a classifier (as described herein) can be used to determine a likelihood or probability score that a sample feature vector is from a subject that has cancer.

In one embodiment, a probability score of greater than or equal to 60 can indicated that the subject has cancer. In still other embodiments, a probability score greater than or equal to 65, greater than or equal to 70, greater than or equal to 75, greater than or equal to 80, greater than or equal to 85, greater than or equal to 90, or greater than or equal to 95, indicated that the subject has cancer. In other embodiments, a probability score can indicate the severity of disease. For example, a probability score of 80 may indicate a more severe form, or later stage, of cancer compared to a score below 80 (e.g., a score of 70). Similarly, an increase in the probability score over time (e.g., at a second, later time point) can indicate disease progression or a decrease in the probability score over time (e.g., at a second, later time point) can indicate successful treatment.

In another embodiment, a cancer log-odds ratio can be calculated for a test subject by taking the log of a ratio of a probability of being cancerous over a probability of being non-cancerous (i.e., one minus the probability of being cancerous), as described herein. In accordance with this embodiment, a cancer log-odds ratio greater than 1 can indicate that the subject has cancer. In still other embodiments, a cancer log-odds ratio greater than 1.2, greater than 1.3, greater than 1.4, greater than 1.5, greater than 1.7, greater than 2, greater than 2.5, greater than 3, greater than 3.5, or greater than 4, indicated that the subject has cancer. In other embodiments, a cancer log-odds ratio can indicate the severity of disease. For example, a cancer log-odds ratio greater than 2 may indicate a more severe form, or later stage, of cancer compared to a score below 2 (e.g., a score of 1). Similarly, an increase in the cancer log-odds ratio over time (e.g., at a second, later time point) can indicate disease progression or a decrease in the cancer log-odds ratio over time (e.g., at a second, later time point) can indicate successful treatment.

According to aspects of the present invention, the methods and systems of the present invention can be trained to detect or classify multiple cancer indications. For example, the methods, systems and classifiers of the present invention can be used to detect the presence of one or more, two or more, three or more, five or more, or ten or more different types of cancer.

In some embodiments, the cancer is one or more of head and neck cancer, liver/bile duct cancer, upper GI cancer, pancreatic/gallbladder cancer; colorectal cancer, ovarian cancer, lung cancer, multiple myeloma, lymphoid neoplasms, melanoma, sarcoma, breast cancer, and uterine cancer. In some embodiments, the cancer is one or more of anorectal cancer, bladder or urothelial cancer, or cervical cancer.

Cancer and Treatment Monitoring

In some embodiments, the likelihood or probability score can be assessed at different time points (e.g., or before or after treatment) to monitor disease progression or to monitor treatment effectiveness (e.g., therapeutic efficacy). For example, the present disclosure provides methods that involve obtaining a first sample (e.g., a first plasma cfDNA sample) from a cancer patient at a first time point, determining a first likelihood or probability score therefrom (as described herein), obtaining a second test sample (e.g., a second plasma cfDNA sample) from the cancer patient at a second time point, and determine a second likelihood or probability score therefrom (as described herein).

In certain embodiments, the first time point is before a cancer treatment (e.g., before a resection surgery or a therapeutic intervention), and the second time point is after a cancer treatment (e.g., after a resection surgery or therapeutic intervention), and the method utilized to monitor the effectiveness of the treatment. For example, if the second likelihood or probability score decreases compared to the first likelihood or probability score, then the treatment is considered to have been successful. However, if the second likelihood or probability score increases compared to the first likelihood or probability score, then the treatment is considered to have not been successful. In other embodiments, both the first and second time points are before a cancer treatment (e.g., before a resection surgery or a therapeutic intervention). In still other embodiments, both the first and the second time points are after a cancer treatment (e.g., before a resection surgery or a therapeutic intervention) and the method is used to monitor the effectiveness of the treatment or loss of effectiveness of the treatment. In still other embodiments, cfDNA samples may be obtained from a cancer patient at a first and second time point and analyzed. e.g., to monitor cancer progression, to determine if a cancer is in remission (e.g., after treatment), to monitor or detect residual disease or recurrence of disease, or to monitor treatment (e.g., therapeutic) efficacy.

Those of skill in the art will readily appreciate that test samples can be obtained from a cancer patient over any desired set of time points and analyzed in accordance with the methods of the invention to monitor a cancer state in the patient. In some embodiments, the first and second time points are separated by an amount of time that ranges from about 15 minutes up to about 30 years, such as about 30 minutes, such as about 1, 2, 3, 4, 5, 6, 7, 8, 9, 10, 11, 12, 13, 14, 15, 16, 17, 18, 19, 20, 21, 22, 23, or about 24 hours, such as about 1, 2, 3, 4, 5, 10, 15, 20, 25 or about 30 days, or such as about 1, 2, 3, 4, 5, 6, 7, 8, 9, 10, 11, or 12 months, or such as about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5 or about 30 years. In other embodiments, test samples can be obtained from the patient at least once every 3 months, at least once every 6 months, at least once a year, at least once every 2 years, at least once every 3 years, at least once every 4 years, or at least once every 5 years.

Treatment

In still another embodiment, information obtained from any method described herein (e.g., the likelihood or probability score) can be used to make or influence a clinical decision (e.g., diagnosis of cancer, treatment selection, assessment of treatment effectiveness, etc.). For example, in one embodiment, if the likelihood or probability score exceeds a threshold, a physician can prescribe an appropriate treatment (e.g., a resection surgery, radiation therapy, chemotherapy, and/or immunotherapy). In some embodiments, information such as a likelihood or probability score can be provided as a readout to a physician or subject.

A classifier (as described herein) can be used to determine a likelihood or probability score that a sample feature vector is from a subject that has cancer. In one embodiment, an appropriate treatment (e.g., resection surgery or therapeutic) is prescribed when the likelihood or probability exceeds a threshold. For example, in one embodiment, if the likelihood or probability score is greater than or equal to 60, one or more appropriate treatments are prescribed. In another embodiments, if the likelihood or probability score is greater than or equal to 65, greater than or equal to 70, greater than or equal to 75, greater than or equal to 80, greater than or equal to 85, greater than or equal to 90, or greater than or equal to 95, one or more appropriate treatments are prescribed. In other embodiments, a cancer log-odds ratio can indicate the effectiveness of a cancer treatment. For example, an increase in the cancer log-odds ratio over time (e.g., at a second, after treatment) can indicate that the treatment was not effective. Similarly, a decrease in the cancer log-odds ratio over time (e.g., at a second, after treatment) can indicate successful treatment. In another embodiment, if the cancer log-odds ratio is greater than 1, greater than 1.5, greater than 2, greater than 2.5, greater than 3, greater than 3.5, or greater than 4, one or more appropriate treatments are prescribed.

In some embodiments, the treatment is one or more cancer therapeutic agents selected from the group consisting of a chemotherapy agent, a targeted cancer therapy agent, a differentiating therapy agent, a hormone therapy agent, and an immunotherapy agent. For example, the treatment can be one or more chemotherapy agents selected from the group consisting of alkylating agents, antimetabolites, anthracyclines, anti-tumor antibiotics, cytoskeletal disruptors (taxans), topoisomerase inhibitors, mitotic inhibitors, corticosteroids, kinase inhibitors, nucleotide analogs, platinum-based agents and any combination thereof. In some embodiments, the treatment is one or more targeted cancer therapy agents selected from the group consisting of signal transduction inhibitors (e.g. tyrosine kinase and growth factor receptor inhibitors), histone deacetylase (HDAC) inhibitors, retinoic receptor agonists, proteosome inhibitors, angiogenesis inhibitors, and monoclonal antibody conjugates. In some embodiments, the treatment is one or more differentiating therapy agents including retinoids, such as tretinoin, alitretinoin and bexarotene. In some embodiments, the treatment is one or more hormone therapy agents selected from the group consisting of anti-estrogens, aromatase inhibitors, progestins, estrogens, anti-androgens, and GnRH agonists or analogs. In one embodiment, the treatment is one or more immunotherapy agents selected from the group comprising monoclonal antibody therapies such as rituximab (RITUXAN) and alemtuzumab (CAMPATH), non-specific immunotherapies and adjuvants, such as BCG, interleukin-2 (IL-2), and interferon-alfa, immunomodulating drugs, for instance, thalidomide and lenalidomide (REVLIMID). It is within the capabilities of a skilled physician or oncologist to select an appropriate cancer therapeutic agent based on characteristics such as the type of tumor, cancer stage, previous exposure to cancer treatment or therapeutic agent, and other characteristics of the cancer.

6.6. Examples

The following examples are put forth so as to provide those of ordinary skill in the art with a complete disclosure and description of how to make and use the present description, and are not intended to limit the scope of what the inventors regard as their description nor are they intended to represent that the experiments below are all or the only experiments performed. Efforts have been made to ensure accuracy with respect to numbers used (e.g., amounts, temperature, etc.) but some experimental errors and deviations should be accounted for.

6.6.1. Example 1: Sequencing cfDNA from Individuals with Cancer and Non-Cancer Controls The Circulating Cell-free Genome Atlas Study ("CCGA"; Clinical Trial.gov identifier NCT02889978) is a prospective, multi-center, case-control, observational study with longitudinal follow-up. De-identified biospecimens were collected from approximately 15,000 participants from 142 sites. Samples were selected to ensure a prespecified distribution of cancer types and non-cancers across sites in each cohort, and cancer and non-cancer samples were frequency age-matched by gender. The STRIVE study is a prospective, multi-center, observational cohort study designed to validate an assay for the early detection of breast cancer and other invasive cancers (See Clinical Trail.gov Identifier: NCT03085888 (clinicaltrials.gov/ct2/show/NCT03085888)). As described below, additional non-cancer samples were selected from the STRIVE study and used for classifier training.

In some embodiments, whole-genome bisulfite sequencing (WGBS; 30× depth) of cfDNA isolated from plasma from the CCGA study subjects was employed for analysis of cfDNA. In other embodiments, as indicated below, a targeted bisulfite sequencing procedure was used for analysis of sample. Under the targeted bisulfite sequencing procedure, a probe set was used to enrich cfDNA molecules derived from a plurality of target genomic regions. For both processes, cfDNA was extracted from two tubes of plasma (up to a combined volume of 10 ml) per patient using a modified QIAamp Circulating Nucleic Acid kit (Qiagen; Germantown, Md.). Up to 75 ng of plasma cfDNA was subjected to bisulfite conversion using the EZ-96 DNA Methylation Kit (Zymo Research, D5003). Converted cfDNA was used to prepare dual indexed sequencing libraries using Accel-NGS Methyl-Seq DNA library preparation kits (Swift BioSciences; Ann Arbor, Mich.). The constructed libraries were quantified using the KAPA Library Quantification Kit for Illumina Platforms (Kapa Biosystems; Wilmington, Mass.). Four libraries along with 10% PhiX v3 library (Illumina, FC-110-3001) were pooled and clustered on an Illumina NovaSeq 6000 S2 flow cell followed by 150-bp paired-end sequencing (30×).

6.6.2. Example 2: Modeling the Methylation Status of Healthy Individuals

A statistical model and a data structure of typical cfDNA fragments were produced using an independent reference set of 108 non-smoking participants without cancer (age: 58±14 years, 79 [73%] women) (i.e., a reference genome) from the CCGA study. These samples were used to train a Markov-chain model (order 3) estimating the likelihood of a given sequence of CpG methylation statuses within a fragment as further described above in Section 6.4.2.1—P-Value Score Calculation. This model was demonstrated to be calibrated within the normal fragment range (p-value>0.001) and was used to reject fragments with a p-value from the Markov model of ≥0.001 as insufficiently unusual.

6.6.3. Example 3: Selection of Target Genomic Regions

Target genomic regions were selected using a database generated by sequencing bisulfite converted cfDNA fragments obtained from 1548 individuals who had been diagnosed with cancer and 1163 individuals who had not been diagnosed with cancer from the CCGA study.

The process for selecting target genomic regions began by identifying anomalous cfDNA fragments from among the bisulfite converted cfDNA fragment sequences from each individual. The fragments were aligned to the hg19 reference genome, and each CpG site within each fragment was scored as methylated or unmethylated, or indeterminate. Anomalous cfDNA fragments have three characteristics: (1) a bisulfite converted methylation pattern with a p-value of <0.001 according to the Markov-chain model, indicating that the methylation pattern would not be expected to occur in individuals without cancer; (2) five or more CpG sites; and (3) a hypermethylated or hypomethylated state wherein at least 80%, 90%, or 100% of the CpG sites are either methylated or unmethylated, respectively. Indeterminant sites were included in the total number of CpG sites when calculating the percentage of methylated or unmethylated CpG sites.

The second step in target selection was to determine a ranking score for each of the approximately 30 million CpG sites in the GRCh37/hg19 reference genome. For each CpG site, a count was made of cancer and non-cancer samples having at least one anomalous cfDNA fragment overlapping the CpG site. Hypermethylated anomalous fragments and hypermethylated anomalous fragments were counted separately. These counts were used to separately calculate scores for hypermethylated and hypomethylated fragments according to the following formula: $(n_{cancer}+1)/(n_{cancer}+n_{non-cancer}+2)$. Three pairs of scores were calculated for each CpG: a first pair for anomalous fragments having an 80% or more hypermethylation or hypomethylation state; a second pair for anomalous fragments having a 90% or more hypermethylation or hypomethylation state; and a third pair for anomalous fragments having a 100% hypermethylation or hypomethylation state. The highest of these six scores became the ranking score for the CpG site.

The third step in target selection was to define targeted regions within the genome. The first region added to the target list was a 30-base region extending 15 bases on either side of the center of the highest ranking CpG site. The list of target regions was then expanded in an iterative process. A 30-base region extending 15 bases on either side of the center of the next highest ranking CpG site was identified. If the new region was within 200 bases of an existing target site, the new region was merged with the existing one to form a larger region including the all bases between the new 30-base region and the old one. If the new region was not within 200 bases of an existing target site, it was simply added to the list of target regions. The list of target regions was iteratively expanded until it reached the desired panel size of 0.59 MB for Assay Panel 1, 1.19 MB for Assay Panel 2, 2.38 MB for Assay Panel 3, 4.96 MB for Assay Panel 4, and 8.53 MB for Assay Panel 5.

6.6.4. Example 4: Probe Design

Biotinylated probes were designed for the purpose of collecting bisulfite-converted anomalous cfDNA fragments that are derived from the genomic regions identified above. Each probe was 120 bases long and had a biotin moiety at its 5' end. Generally, probe sets were designed to include probes that target fragments from each of the CpG sites included within the start/stop ranges of any of the targeted regions included in any one of Lists 1-8.

To increase the probability of capturing anomalous cfDNA fragments derived from a target region (or a portion of a target region), including anomalous cfDNA fragments with partial target sequences at their 5' or 3' ends, probes were arranged in a tiled fashion so that two probes aligned to each base within a target region. Adjacent 120-base probes were designed to overlap by 60 bases. Target regions of 60 or fewer bases were initially targeted by three probes as illustrated in FIG. 1A. Additional probes were used for target regions of larger size (see e.g., FIG. 1B). For both size classes of target regions, the probes used to interrogate each region collectively extend beyond the target region (e.g., to include at least 60 bases of non-targeted sequence on either side of the target region due to the tiled arrangement; see FIG. 1A). Additionally, probes were designed to enrich DNA molecules derived from both strands of DNA from each target region, such that a single base pair of a target genomic region may be targeted by four probes: two for each strand.

Probe sequences were designed to be complementary to bisulfite-converted anomalous cfDNA fragments from each of the genomic regions, where every CpG site in a cfDNA fragment is either methylated or unmethylated. Thus, if the anomalous cfDNA fragments aligning with a target sequence are hypomethylated, all, or most of the CpG sites within the fragment would be expected to be converted to UpG sequences, and the corresponding probes would have CpA sequences for all, or most of the CpGs in the target. Conversely, if the anomalous cfDNA sequences aligning with a target sequence are hypermethylated, all, or most of the CpG sites within the fragment would be expected to be protected from conversion to UpG sequences, and the corresponding probes would have CpG sequences for all, or most of the CpGs in the target. Cytosines not located within a CpG site are generally not methylated. These bystander cytosines are therefore converted to uracil regardless of the methylation status of adjacent CpG sites. Probes matching a target site were designed to pull down hypomethylated cfDNA fragments or hypermethylated cfDNA fragments, but generally not both. This "semibinary" design contrasts with a "binary" design where cfDNA fragments from the same target region are targeted with two sets of probes, one designed to pull down hypomethylated cfDNA and the other designed to pull down hypermethylated cfDNA at the same region.

6.6.5. Example 5: Probe Quality Control

Poor quality probes likely to pull down a significant number off-target cfDNA fragments were excluded from the cancer assay panels.

To determine the characteristics of a poor-quality probe, an experiment was conducted to test how much overlap between a cfDNA fragment and a probe is required to achieve a non-negligible amount of pulldown.

Purified, bisulfite converted cfDNA was mixed with biotinylated probes in Hybridization Capture Buffer (Argonaut Technologies, Redwood City, Calif., Cat #310450) supplemented with 1 mM Tris, pH 8.0 in a 96-well plate, and processed in a Hamilton Star Liquid Handler (Hamilton, Reno, Nev., Cat #STAR AL 8/96 iSWAP) and a 96-well BioRad C1000 Touch Thermocycler (BiRad, Hercules, Calif., Cat #1851196). The temperature of the hybridization mix was raised to 95° C. for 10 minutes, and then gradually decreased by 2° C./min to 62° C., with 1-minute pauses at 93° C. and 91° C. Hybridization continued for 15.5-17.5 hours at 62° C. A second aliquot of probes was added, and the thermal cycling program was repeated. Captured cfDNA was captured on Streptavidin Magnetic Beads (Illumina, San Diego, Calif., Cat #20014367), amplified by PCR, and then sequenced.

Various overlap lengths were tested using preliminary assay panels (V1D3, V1D4, V1E2) designed to include probes having various overlaps ranging from 0 to 120 bases. Samples comprising 175 bp target DNA fragments were applied to the panel and washed, and then DNA fragments bound to the probes were collected. The amounts of the collected DNA fragments were measured, and then plotted as densities over the sizes of overlaps as provided in FIG. 10.

There was no significant binding and pull down of target DNA fragments when the overlap was less than 45 bp. These results indicate that, with the specified hybridization conditions, a fragment-probe overlap of at least 45 bp is generally required to maximize hybridization between the probe set and nucleic acids derived from the target genomic regions, and thus improve pulldown efficiency.

Furthermore, binding, and thus pulldown efficiency, is greatly disrupted when the percentage of mismatches between the probe and fragment sequences in the region of overlap is greater than 10%. It was therefore concluded that off-target pulldown may occur for probes having a sequence with a match rate of at least 90% to an off-target genomic region of at least 45 bp.

For each probe, we performed an exhaustive, bisulfate aware search of the entire reference genome for off-target regions having 45 bp alignments with a 90%+ match rate. Specifically, we combined a k-mer seeding strategy (which can allow one or more mismatches) with local alignment at the seed locations. This guaranteed against missing any good alignments based on k-mer length, number of mismatches allowed, and number of k-mer seed hits at a particular location. The search involved performing dynamic programming local alignment at a large number of locations, so the implementation was optimized to use vector CPU instructions (e.g., AVX2, AVX512) and parallelized across many cores within a machine and also across many machines connected by a network. This implementation allows for an exhaustive search, which is valuable in designing a high-performance panel (i.e., low off-target rate and high target coverage for a given amount of sequencing).

Following the exhaustive search, each probe was scored based on its number of off-target regions. The best probes (high) have a score of 1, meaning they match only one genomic region—the target. Probes with an intermediate score of between 2-19 hits (intermediate) were accepted but probes with a poor score of 20 or more hits (poor) were discarded. Table 1 presents a summary of the probes in Assay Panels 3-5, including the numbers and percentages of probes retained after eliminating low quality probes with potential off-target effects. The probe region is larger than the target region because some probes extend beyond the ends of target regions.

TABLE 1

Probe numbers and target region sizes before and after probe quality control

|  | Original probes | Final probes | Final probe target (MB) | Final target region (Mb) | Fraction of original target |
|---|---|---|---|---|---|
| Assay Panel 3 | 127,734 | 102,013 | 3.798 | 2.12 | 88.1% |
| Assay Panel 4 | 256,988 | 189,155 | 7.013 | 4.15 | 83.5% |
| Assay Panel 5 | 449,088 | 303,262 | 11.35 | 6.71 | 78.5% |

Additionally, numbers of high quality, intermediate quality, and poor-quality probes were counted among probes targeting hypermethylated genomic regions or hypomethylated genomic regions. As shown in FIG. 11, probes targeting hypermethylated genomic regions tend to have significantly less off-target matches.

6.6.6. Example 4: Characterization of Target Genomic Regions

Lists 1 to 8 (see Table 2 below) present Assay Panels of various sizes representing the portion of targeted genomic regions for which probes were designed to enrich DNA molecules derived from these targeted genomic regions. Assay Panels 1-5 are arranged from small to large according to the size budget used to select their target genomic regions. These Assay Panels were filtered to exclude certain CpG sites and genomic regions. Assay Panel 6, which defines a larger genomic region than any of Assay Panels 1-5, includes all of the CpG sites and genomic regions that were filtered out to produce each of Assay Panels 1-5. Assay Panels 3A and 4A present subsets of the target genomic regions in Assay Panels 3 and 4, respectively, excluding genomic regions that are also described in PCT/US2019/025358.

TABLE 2

Correspondence between Assay Panels, Lists, and SEQ ID NOs

| Name | List | SEQ ID NO range |
|---|---|---|
| Assay Panel 1 | List 1 | 1-1644 |
| Assay Panel 2 | List 2 | 1645-5270 |
| Assay Panel 3 | List 3 | 5271-16837 |
| Assay Panel 3A | List 4 | 16838-25984 |
| Assay Panel 4 | List 5 | 25985-46929 |
| Assay Panel 4A | List 6 | 46930-67335 |
| Assay Panel 5 | List 7 | 67336-101617 |
| Assay Panel 6 | List 8 | 101618-131822 |

The sequence listing includes the following information: (1) SEQ ID NO, (2) a sequence identifier that identifies (a) a chromosome or contig on which the CpG site is located and (b) a start and stop position of the region, (3) the sequence corresponding to (2) and (4) whether the region was included based on its hypermethylation or hypomethylation score. The chromosome numbers and the start and stop positions are provided relative to a known human reference genome, GRCh37/hg19. The sequence of GRCh37/hg19 is available from the National Center for Biotechnology Information (NCBI), the Genome Reference Consortium, and the Genome Browser provided by Santa Cruz Genomics Institute.

Generally, a probe can be designed to target any of the CpG sites included within the start/stop ranges of any of the targeted regions included in Lists 1-8. Alternatively stated, in some embodiments, probes can be designed to hybridize to any CpG site in fragments derived from any of the targeted regions, such as converted fragments from the target region.

The Assay Panels were analyzed to understand their features. The sizes of target genomic regions of the Assay Panels, prior to filtering out off-target probes, are shown in Table 10. The number of CpG sites per target genomic region, for each of various assay panels (prior to filtering out off-target probes), is plotted in FIG. 12A as a function of density. The per probe G/C content of various assay panels is presented in FIG. 12.B.

TABLE 10

Target genomic region sizes

| Region size | Assay Panel 1 | Assay Panel 2 | Assay Panel 3 | Assay Panel 4 | Assay Panel 6 |
|---|---|---|---|---|---|
| Smallest | 15 | 15 | 15 | 15 | 15 |
| Median | — | — | 95 | 94 | 82 |
| Mean | — | — | 207 | 229 | 220 |
| Largest | 2593 | 3374 | 3374 | 4368 | 6820 |

Target genomic regions within the Assay Panels were next aligned to a reference genome to evaluate their locations. Target genomic regions were positioned in introns, exons, intergenic regions, 5'UTRs, 3'UTRs, or controlling regions such as promoters or enhancers. The number of target genomic regions that fall within each genomic annotation for Assay Panels 3-5 were counted and plotted in the graphs provided in FIG. 13. FIG. 13 also compares numbers of the selected target genomic regions (black bars) with numbers of randomly selected genomic regions (gray bars) that fall within each genomic annotation.

The analysis shows that the selected target genomic regions are not random in their genomic distributions. Functional elements such as promoters, 5'UTRs, exons, and intron/exon boundaries were more highly represented in the assay panels compared to randomly selected regions, while intergenic regions were underrepresented.

6.6.7. Example 7: Generation of a Mixture Model Classifier

To maximize performance, the predictive cancer models described in this Example were trained using sequence data obtained from a plurality of samples from known cancer types and non-cancers from both CCGA sub-studies (CCGA1 and CCGA22), a plurality of tissue samples for known cancers obtained from CCGA1, and a plurality of non-cancer samples from the STRIVE study (See Clinical Trail.gov Identifier: NCT03085888 (//clinicaltrials.gov/ct2/show/NCT03085888)). The STRIVE study is a prospective, multi-center, observational cohort study to validate an assay for the early detection of breast cancer and other invasive cancers, from which additional non-cancer training samples were obtained to train the classifier described herein. The known cancer types included from the CCGA sample set included the following: breast, lung, prostate, colorectal, renal, uterine, pancreas, esophageal, lymphoma, head and neck, ovarian, hepatobiliary, melanoma, cervical, multiple myeloma, leukemia, thyroid, bladder, gastric, and anorectal. As such, a model can be a multi-cancer model (or a multi-cancer classifier) for detecting one or more, two or more, three or more, four or more, five or more, ten or more, or 20 or more different types of cancer.

Classifier performance data shown below for Assay Panels 1-6, was reported out for a locked classifier trained on cancer and non-cancer samples obtained from the CCGA sub-study (CCGA2) and the STRIVE study. The individuals in the CCGA2 sub-study were different from the individuals in the CCGA1 sub-study whose cfDNA was used to select target genomes. From the CCGA2 study, blood samples were collected from individuals diagnosed with untreated cancer (including 20 tumor types and all stages of cancer) and healthy individuals with no cancer diagnosis (controls). For STRIVE, blood samples were collected from women within 28 days of their screening mammogram. Cell-free DNA (cfDNA) was extracted from each sample and treated with bisulfite to convert unmethylated cytosines to uracils. The bisulfite treated cfDNA was enriched for informative cfDNA molecules using hybridization probes designed to enrich bisulfite-converted nucleic acids derived from each of a plurality of targeted genomic regions in an assay panel comprising all of the genomic regions of Assay Panels 1-6. The enriched bisulfite-converted nucleic acid molecules were sequenced using paired-end sequencing on an Illumina platform (San Diego, Calif.) to obtain a set of sequence reads for each of the training samples, and the resulting read pairs were aligned to the reference genome, assembled into fragments, and methylated and unmethylated CpG sites identified.

Classifier performance was evaluated for Assay Panels 1-6, and reported in this Example and in FIGS. 14-27, over a set of training samples that included 3,053 samples (1,532 cancer samples and 1,521 non-cancer samples). All sample types used for evaluating classifier performance are shown below in Table 3.

TABLE 3

Cancer diagnoses of individuals whose cfDNA was used to train the classifier

| Cancer Type | Total | Stage | | | | Not Reported |
|---|---|---|---|---|---|---|
| | | I | II | III | IV | |
| Non-cancer | 1521 | — | — | — | — | — |
| Lung | 261 | 60 | 23 | 72 | 106 | 0 |
| Breast | 247 | 102 | 110 | 27 | 8 | 0 |
| Prostate | 188 | 39 | 113 | 19 | 17 | 0 |
| Lymphoid neoplasm | 147 | 15 | 27 | 27 | 39 | 39 |
| Colorectal | 121 | 13 | 22 | 41 | 45 | 0 |
| Pancreas and gallbladder | 95 | 15 | 15 | 19 | 46 | 0 |
| Uterine | 84 | 73 | 3 | 5 | 3 | 0 |
| Upper GI | 67 | 9 | 12 | 19 | 27 | 0 |
| Head and neck | 62 | 7 | 13 | 16 | 26 | 0 |
| Renal | 56 | 37 | 4 | 4 | 11 | 0 |
| Ovary | 37 | 4 | 2 | 25 | 6 | 0 |
| Multiple myeloma | 34 | 10 | 13 | 11 | 0 | 0 |
| Not reported | 29 | 8 | 5 | 7 | 6 | 3 |
| Liver bile duct | 29 | 5 | 7 | 7 | 10 | 0 |
| Sarcoma | 17 | 2 | 4 | 5 | 6 | 0 |
| Bladder and urothelial | 16 | 6 | 7 | 3 | 1 | 0 |
| Anorectal | 14 | 4 | 5 | 5 | 0 | 0 |
| Cervical | 11 | 8 | 1 | 2 | 0 | 0 |
| Melanoma | 7 | 3 | 1 | 0 | 3 | 0 |
| Myeloid neoplasm | 4 | 2 | 1 | 0 | 1 | 0 |
| Thyroid | 4 | 0 | 0 | 0 | 0 | 4 |
| Prediction only | 2 | 0 | 0 | 0 | 2 | 0 |

Mixture Model Based Featurization

For each cancer type (including non-cancer) a probabilistic mixture model was trained and utilized to assign a probability to each fragment from each cancer and non-cancer sample based on how likely it was that the fragment would be observed in a given sample type.

Briefly, for each sample type (cancer and non-cancer samples), for each region (where each region was 1 kb in length with a 50% overlap between adjacent regions), a probabilistic model was fit to the fragments derived from the training samples for each type or cancer and non-cancer. The probabilistic model trained for each sample type was a mixture model, where each of three mixture components was an independent-sites model in which methylation at each CpG is assumed to be independent of methylation at other CpGs. Fragments were excluded from the model if: they had a p-value greater than 0.01, were marked as duplicate fragments, the fragments had a bag size of greater than 1; they did not cover at least one CpG site; or if the fragment was greater than 1000 bases in length.

Each probabilistic model was fit using maximum-likelihood estimation to identify a set of parameters that maximized the log-likelihood of all fragments deriving from each sample type, subject to a regularization penalty.

Featurization

Features were extracted for each fragment from each training sample, for each cancer type and non-cancer sample, in each region. The extracted features were the tallies of outlier fragments (i.e., anomalously methylated fragments), which were defined as those whose log-likelihood under a first cancer model exceeded the log-likelihood under a second cancer model or non-cancer model by at least a threshold tier value. Outlier fragments were tallied separately for each genomic region, sample model (i.e., cancer type), and tier (for tiers 1, 2, 3, 4, 5, 6, 7, 8, and 9), yielding 9 features per region for each sample type.

Feature Ranking and Classifier Training

For each set of pairwise features, the features were ranked using mutual information based on their ability to distinguish the first cancer type (which defined the log-likelihood model from which the feature was derived) from the second cancer type or non-cancer. The top ranked 256 features from each pairwise comparison were identified and added to the final feature set for each cancer type and non-cancer. The features in the final feature set for each sample (cancer type and non-cancer) were binarized (any feature value greater than 0 was set to 1, so that all features were either 0 or 1). The training samples were then divided into distinct 5-fold cross-validation training sets and used to train a logistic regression classifier (for detecting the presence of cancer) and a multiclass logistic regression classifier (for determining cancer tissue of origin). During the classifier training process, the cross-validated scores assigned to the training set were collected.

Once the binary cancer/non-cancer classifier was trained, a probability score was determined from the classifier for each of the training samples. Training samples with a probability score that exceeded a threshold were called as positive for cancer. This threshold was prespecified to target a desired specificity level, based on the distribution of cross-validated scores assigned to the training set. For example, if the desired specificity level was 99.4%, the threshold would be set to the 99.4th percentile of the cross-validated cancer detection probability scores assigned to the non-cancer samples in the training set. A tissue of origin or cancer type assessment was subsequently made for each training sample determined to be positive for cancer from the multiclass classifier. First, the multiclass logistic regression classifier assigned a set of probability scores, one for each prospective cancer type, to each sample. Next, the confidence of these scores was assessed as the difference between the highest and second-highest scores. A threshold was prespecified as the minimum value such that, of the cancer samples in the training set with a top-two score differential exceeding the threshold, 90% had been assigned the correct TOO label as their highest score. For prediction on new samples, samples with a top-two score differential lower than this threshold received an assignment of "indeterminate cancer"; those whose score differential exceeded the threshold were assigned the cancer label to which the multiclass classifier assigned the highest score.

6.6.8. Example 8: Classifier Performance

As a proxy for testing different probe sets (bait sets), classifier performance was determined for each of Assay Panels 1-6 by constraining the data set and only considering the methylation status of CpG sites within fragments that would be enriched for by the specified Assay Panels.

The results of the classifier performance analysis are provided in Tables 11 to 18. For each set of genomic regions (i.e., Assay Panels 1-6), the Detection column of the tables indicates the performance of the classifier over the indicated Assay Panels. Here, Detection is the sensitivity for all cancer types included in the CCGA2 study stratified by cancer stage at 99% specificity. The Tissue of Origin column indicates the accuracy of a tissue of origin classification at 99% specificity only for individuals diagnosed with cancer and when sufficient methylation data was available to assign a tissue of origin. Values indicate mean accuracy, with a 95% confidence interval in brackets and the number correctly assigned divided by the total in the category in parenthesis.

TABLE 11

Classification accuracy using the genomic regions of Assay Panel 1

| Stage | Detection* | Tissue of Origin* |
|---|---|---|
| I | 16.1% [12.7-20] (68/422) | 76.9% [63.2-87.5] (40/52) |
| II | 40.5% [35.5-45.5] (157/388) | 89.6% [83.1-94.2] (120/134) |
| III | 75.7% [70.6-80.4] (237/313) | 90.2% [85.5-93.9] (194/215) |
| IV | 89.3% [85.6-92.2] (324/363) | 91.9% [88.3-94.8] (274/298) |
| All | 52.2% [49.6-54.7] (799/1532) | 89.9% [87.4-92] (640/712) |

TABLE 12

Classification accuracy using the genomic regions of Assay Panel 2

| Stage | Detection* | Tissue of Origin* |
|---|---|---|
| I | 19.2% [15.5-23.3] (81/422) | 68.9% [55.7-80.1] (42/61) |
| II | 43.3% [38.3-48.4] (168/388) | 86.4% [79.8-91.5] (127/147) |
| III | 78% [72.9-82.4] (244/313) | 91.4% [87-94.8] (203/222) |
| IV | 90.1% [86.5-93] (327/363) | 94.3% [91-96.6] (280/297) |
| All | 54.6% [52-57.1] (836/1532) | 89.8% [87.3-91.8] (666/742) |

TABLE 13

Classification accuracy using the genomic regions of Assay Panel 3

| Stage | Detection* | Tissue of Origin* |
|---|---|---|
| I | 19.2% [15.5-23.3] (81/422) | 76.3% [63.4-86.4] (45/59) |
| II | 43.6% [38.6-48.7] (169/388) | 86.3% [79.8-91.3] (132/153) |
| III | 79.9% [75-84.2] (250/313) | 91% [86.6-94.4] (213/234) |
| IV | 90.6% [87.2-93.4] (329/363) | 92.6% [89.1-95.3] (289/312) |
| All | 55.4% [52.9-57.9] (849/1532) | 89.7% [87.3-91.8] (697/777) |

TABLE 14

Classification accuracy using the genomic regions of Assay Panel 4

| Stage | Detection* | Tissue of Origin* |
|---|---|---|
| I | 22% [18.2-26.3] (93/422) | 71.6% [59.3-82] (48/67) |
| II | 44.3% [39.3-49.4] (172/388) | 86.2% [79.7-91.2] (131/152) |
| III | 81.2% [76.4-85.3] (254/313) | 91.7% [87.3-94.9] (209/228) |
| IV | 90.4% [86.8-93.2] (328/363) | 93.4% [90-95.9] (284/304) |
| All | 56.8% [54.3-59.3] (870/1532) | 89.6% [87.3-91.7] (691/771) |

TABLE 15

Classification accuracy using the genomic regions of Assay Panel 5

| Stage | Detection* | Tissue of Origin* |
|---|---|---|
| I | 21.8% [18-26] (92/422) | 75.4% [63.5-84.9] (52/69) |
| II | 43.3% [38.3-48.4] (168/388) | 89.1% [83.1-93.5] (139/156) |
| III | 82.4% [77.8-86.5] (258/313) | 92.2% [88-95.3] (214/232) |
| IV | 90.4% [86.8-93.2] (328/363) | 91.7% [88-94.5] (286/312) |
| All | 56.7% [54.2-59.2] (869/1532) | 89.6% [87.3-91.7] (709/791) |

TABLE 16

Classification accuracy using the genomic regions of Assay Panel 6

| Stage | Detection* | Tissue of Origin* |
|---|---|---|
| I | 22% [18.2-263] (93/422) | 75.3% [63.9-84.7] (55/73) |
| II | 45.6% [40.6-50.7] (177/388) | 87.3% [81.3-92] (145/166) |
| III | 81.8% [77.1-85.9] (256/313) | 91.7% [87.5-94.9] (222/242) |

TABLE 16-continued

Classification accuracy using the genomic regions of Assay Panel 6

| Stage | Detection* | Tissue of Origin* |
|---|---|---|
| IV | 90.1% [86.5-93] (327/363) | 92.1% [88.6-94.8] (292/317) |
| All | 57.1% [54.6-59.6] (875/1532) | 89.5% [87.2-91.5] (733/819) |

TABLE 17

Classification accuracy using the genomic regions of Assay Panel 3A

| Stage | Detection* | Tissue of Origin* |
|---|---|---|
| I | 16.1% [12.7-20] (68/422) | 71.7% [57.7-83.2] (38/53) |
| II | 40.2% [35.3-45.3] (156/388) | 87% [80.4-92] (127/146) |
| III | 74.8% [69.6-79.5] (234/313) | 92% [87.5-95.3] (195/212) |
| IV | 88.2% [84.4-91.3] (320/363) | 91.8% [88.1-94.7] (269/293) |
| All | 52.2% [49.6-54.7] (799/1532) | 89.3% [86.9-91.5] (645/722) |

TABLE 18

Classification accuracy using the genomic regions of Assay Panel 4A

| Stage | Detection* | Tissue of Origin* |
|---|---|---|
| I | 17.3% [13.8-21.3] (73/422) | 74.1% [60.3-85] (40/54) |
| II | 40.7% [35.8-45] (158/388) | 88.5% [82.2-93.2] (131/148) |
| III | 79.2% [74.3-83.6] (248/313) | 89.7% [85-93.3] (208/232) |
| IV | 89% [53-92] (323/363) | 92.3% [88.7-95] (286/310) |
| All | 53.7% [51.1-56.2] (822/1532) | 89.4% [87-91.5] (682/763) |

These results show that the accuracy of detection and tissue of origin determination is higher for later stage cancers than early stage cancers. Additionally, larger panels apparently provide more accurate cancer detection for stage I and stage II cancers.

Part A of FIGS. 14-21 presents receiver operator curves (ROC curves) for Assay Panels 1-6 and 3A and 4A from the binary logistic regression classifier using mixture model based featurization described above. The ROC curve results were similar for all Assay Panels, showing an area under the curves (AUC) falling within a narrow range of 0.80 to 0.83. Part B of FIGS. 14-21 presents confusion matrices showing tissue of origin (TOO) accuracy determined for the multi-class logistic regression classifier trained using mixture model-based features, as described above. As shown in FIGS. 14-21, TOO precision ranged from 89.9% to 91.1% across Assay Panels 1-6.

The classification performance for random subsets of the markers in Assay Panels 3-5, at 99% specificity, are presented in Tables 19-24.

TABLE 19

Classification accuracy using a randomly selected subset of 40% of the genomic regions of Assay Panel 3 (subset a)

| Stage | Detection* | Tissue of Origin* |
|---|---|---|
| I | 18.5% [14.9-22.5] (78/422) | 73.2% [59.7-84.2] (41/56) |
| II | 42% [37-47.1] (163/388) | 87.9% [81.3-92.8] (123/140) |
| III | 79.6% [74.7-83.9] (249/313) | 92.6% [88.2-95.7] (200/216) |
| IV | 89.5% [859-92.5] (325/363) | 91% [87.2-94] (274/301) |
| All | 54.4% [51.9-57] (834/1532) | 89.6% [87.1-91.7] (654/730) |

TABLE 20

Classification accuracy using a randomly selected subset of 40% of the genomic regions of Assay Panel 3 (subset b)

| Stage | Detection* | Tissue of Origin* |
|---|---|---|
| I | 17.8% [14.2-21.8] (75/422) | 75% [61.6-85.6] (42/56) |
| II | 41.5% [36.5-46.6] (161/388) | 85.9% [79.1-91.2] (122/142) |
| III | 77.6% [72.6-82.1] (243/313) | 92.3% [88-95.5] (205/222) |
| IV | 89.3% [85.6-92.2] (324/363) | 91.7% [88.1-94.6] (278/303) |
| All | 53.6% [51.1-56.1] (821/1.532) | 89.5% [87-91.6] (663/741) |

TABLE 21

Classification accuracy using a randomly selected subset of 40% of the genomic regions of Assay Panel 3 (subset c)

| Stage | Detection* | Tissue of Origin* |
|---|---|---|
| I | 16.8% [13.4-20.7] (71/422) | 79.6% [66.5-89.4] (43/54) |
| II | 42.5% [37.6-47.6] (165/388) | 85% [78.2-90.4] (125/147) |
| III | 77.3% [72.3-81.8] (242/313) | 91.8% [87.2-95.2] (191/208) |
| IV | 89.5% [85.9-92.5] (325/363) | 92.3% [88.6-95] (275/298) |
| All | 53.7% [51.2-56.2] (823/1532) | 89.7% [87.2-91.8] (650/725) |

TABLE 22

Classification accuracy using a randomly selected subset of 60% of the genomic regions of Assay Panel 3

| Stage | Detection* | Tissue of Origin* |
|---|---|---|
| I | 18% [14.5-22] (76/422) | 71.4% [57.8-82.7] (40/56) |
| II | 41.2% [36.3-46.3] (160/388) | 86% [79.2-91.2] (123/143) |
| III | 78.6% [73.6-83] (246/313) | 91.1% [86.6-94.5] (205/225) |
| IV | 89.5% [85.9-92.5] (325/363) | 91.6% [87.8-94.5] (272/297) |
| All | 54% [51.5-56.6] (828/1532) | 88.7% [86.2-90.9] (658/742) |

TABLE 23

Classification accuracy using a randomly selected subset of 50% of the genomic regions of Assay Panel 4

| Stage | Detection* | Tissue of Origin* |
|---|---|---|
| I | 18.5% [14.9-22.5] (78/422) | 80.7% [68.1-90] (46/57) |
| II | 44.3% [39.3-49.4] (172/388) | 82.9% [76-88.5] (126/152) |
| III | 78.9% [74-83.3] (247/313) | 91.7% [87.3-95] (200/218) |
| IV | 90.4% [86.8-93.2] (328/363) | 92.4% [88.9-95.1] (281/304) |
| All | 55.3% [52.8-57.8] (847/1532) | 89.5% [87-91.6] (670/749) |

TABLE 24

Classification accuracy using a randomly selected subset of 50% of the genomic regions of Assay Panel 5

| Stage | Detection* | Tissue of Origin* |
|---|---|---|
| I | 20.4% [16.6-24.5] (86/422) | 73.8% [61.5-84] (48/65) |
| II | 43.3% [38.3-48.4] (168/388) | 87% [80.7-91.9] (134/154) |
| III | 80.2% [75.3-84.5] (251/313) | 90.7% [86.2-94.2] (206/227) |
| IV | 89% [53-92] (323/363) | 92.7% [89.2-95.4] (281/303) |
| All | 55.4% [52.8-57.9] (848/1532) | 89.4% [87-91.5] (686/767) |

Part A of FIGS. 22-27 presents receiver operator curves (ROC curves) for randomly selected subsets of Assay Panels 3-4 from the trained binary logistic regression classifier using mixture model based featurization, as described above. Classifier performance results for the same random subsets the markers are also shown in Tables 19-24. As shown, the areas under the curve (AUC) for these receiver operator curves (ROC curves) were similar to each other and similar to the areas under the curve (AUC) for the complete assay panels. A summary of the area under the curve results (AUC) for each Assay Panel is presented in Table 25. Part B of FIGS. 22-27 presents confusion matrices showing tissue of origin (TOO) accuracy determined for the multi-class logistic regression classifier described above. As shown in FIGS. 22-27, TOO precision ranged from 90.4% to 90.7% for the randomly selected subsets of Assay Panels 3-4.

TABLE 25

Areas under the curves for cancer classification.

| Assay Panel | AUC |
| --- | --- |
| 1 | 0.81 |
| 2 | 0.82 |
| 3 | 0.82 |
| 4 | 0.83 |
| 5 | 0.83 |
| 6 | 0.83 |
| 3A | 0.80 |
| 4A | 0.82 |
| 3 Random 40% a | 0.81 |
| 3 Random 40% b | 0.82 |
| 3 Random 40% c | 0.82 |
| 3 Random 60% | 0.82 |
| 4 Random 50% | 0.82 |
| 5 Random 50% | 0.78 |

Table 26 shows tissue of origin accuracy for each cancer type at a specificity of 0.994 for Assay Panels 1, 3A and 5. Each column shows TOO precision with a 95% confidence interval in brackets and in parenthesis the number correctly assigned divided by the total number of samples correctly detected as having cancer under the binary logistic regression classifier described above.

TABLE 26

TOO precision for Assay Panels 1, 3A, and 5

| Cancer Type | Assay Panel 1 | Assay Panel 3A | Assay Panel 5 |
| --- | --- | --- | --- |
| Lung | 97% [93.2-99] (163/168) | 97% [93.2-99] (163/168) | 97.3% [93.7-99.1] (178/183) |
| Colorectal | 97.8% [92.2-99.7] (88/90) | 97.7% [91.9-99.7] (84/86) | 98.9% [94.3-100] (94/95) |
| Lymphoid neoplasm | 100% [95.4-100] (79/79) | 100% [95.9-100] (89/89) | 100% [96-100] (90/90) |

TABLE 26-continued

TOO precision for Assay Panels 1, 3A, and 5

| Cancer Type | Assay Panel 1 | Assay Panel 3A | Assay Panel 5 |
| --- | --- | --- | --- |
| Breast | 98.6% [92.3-100] (69/70) | 98.6% [92.2-100] (68/69) | 98.8% [93.5-100] (82/83) |
| Pancreas Gallbladder | 87.7% [77.2-94.5] (57/65) | 90.9% [81.3-96.6] (60/66) | 90.5% [81.5-96.1] (67/74) |
| Head and Neck | 89.8% [77.8-96.6] (44/49) | 85.1% [71.7-93.8] (40/47) | 88.2% [76.1-95.6] (45/51) |
| Upper GI | 80.9% [66.7-90.9] (38/47) | 89.8% [77.8-96.6] (44/49) | 86.5% [74.2-94.4] (45/52) |
| Ovary | 86.4% [65.1-97.1] (19/22) | 91.3% [72-98.9] (21/23) | 88.9% [70.8-97.6] (24/27) |
| Liver/Bile Duct | 77.8% [52.4-93.6] (14/18) | 70.8% [48.9-87.4] (17/24) | 77.3% [54.6-92.2] (17/22) |
| Uterine | 100% [75.3-100] (13/13) | 92.9% [66.1-99.8] (13/14) | 95.2% [76.2-99.9] (20/21) |
| Prostate | 92.3% [64-99.8] (12/13) | 87.5% [61.7-98.4] (14/16) | 94.4% [72.7-99.9] (17/18) |
| Multiple Myeloma | 92.3% [64-99.8] (12/13) | 94.7% [74-99.9] (18/19) | 91.3% [72-98.9] (21/23) |
| Renal | 100% [69.2-100] (10/10) | 100% [66.4-100] (9/9) | 100% [73.5-100] (12/12) |
| Anorectal | 0% [0-45.9] (0/6) | 0% [0-33.6] (0/9) | 12.5% [0.3-52.7] (1/8) |
| Bladder and urothelia | 0% [0-60.2] (0/4) | 40% [5.3-85.3] (2/5) | 50% [11.8-88.2] (3/6) |
| Sarcoma | 66.7% [9.4-99.2] (2/3) | 25% [0.6-80.6] (1/4) | 50% [6.8-93.2] (2/4) |
| Cervical | 0% [0-97.5] (0/1) | 100% [15.8-100] (2/2) | 25% [0.6-80.6] (1/4) |
| Melanoma | 100% [2.5-100] (1/1) | 66.7% [9.4-99.2] (2/3) | 100% [29.2-100] (3/3) |

Tables 27-29 show classifier performance for the binary logistic regression classifier described above for Assay Panels 1, 3A and 5. Each tables shows the sensitivity for each cancer type, stratified by stage, at a specificity of 0.994. Each column also shows the 95% confidence interval in brackets and in parenthesis the number correctly detected divided by the total number of samples in the data set for each cancer type, at stages I through IV.

TABLE 27

Classifier performance by cancer type and stage for Assay Panel 1

| Cancer Type | I | II | III | IV | All Stages |
| --- | --- | --- | --- | --- | --- |
| Lung | 16.7% [8.3-28.5] (10/60) | 78.3% [56.3-92.5] (18/23) | 83.3% [72.7-91.1] (60/72) | 86.8% [78.8-92.6] (92/106) | 69% [63-74.5] (180/261) |
| Prostate | 0% [0-9] (0/39) | 0.9% [0-4.8] (1/113) | 10.5% [1.3-33.1] (2/19) | 76.5% [50.1-93.2] (13/17) | 8.5% [4.9-13.5] (16/188) |
| Breast HR positive | 2.3% [0.3-8.1] (2/87) | 20% [11.4-31.3] (14/70) | 71.4% [41.9-91.6] (10/14) | 100% [54.1-100] (6/6) | 18.1% [12.7-24.6] (32/177) |
| Lymphoid neoplasm | 20% [4.3-48.1] (3/15) | 74.1% [53.7-88.9] (20/27) | 70.4% [49.8-86.2] (19/27) | 76.9% [60.7-88.9] (30/39) | 56.5% [48-64.6] (83/147) |

TABLE 27-continued

Classifier performance by cancer type and stage for Assay Panel 1

| Cancer Type | I | II | III | IV | All Stages |
|---|---|---|---|---|---|
| Colorectal | 41.2% [18.4-67.1] (7/17) | 66.7% [46-83.5] (18/27) | 80.4% [66.1-90.6] (37/46) | 93.3% [81.7-98.6] (42/45) | 77% [69-83.8] (104/135) |
| Pancreas | 58.3% [27.7-84.8] (7/12) | 71.4% [41.9-91.6] (10/14) | 81.2% [54.4-96] (13/16) | 92.9% [80.5-98.5] (39/42) | 82.1% [72.3-89.6] (69/84) |
| Endometrial carcinoma | 13.7% [6.8-23.8] (10/73) | 33.3% [0.8-90.6] (1/3) | 60% [14.7-94.7] (3/5) | 66.7% [9.4-99.2] (2/3) | 19% [11.3-29.1] (16/84) |
| Breast HR negative | 0% [0-21.8] (0/15) | 62.5% [45.8-77.3] (25/40) | 100% [75.3-100] (13/13) | 100% [15.8-100] (2/2) | 57.1% [44.7-68.9] (40/70) |
| Head and Neck | 85.7% [42.1-99.6] (6/7) | 76.9% [46.2-95] (10/13) | 87.5% [61.7-98.4] (14/16) | 88.5% [69.8-97.6] (23/26) | 85.5% [74.2-93.1] (53/62) |
| Renal | 0% [0-9.5] (0/37) | 0% [0-60.2] (0/4) | 50% [6.8-93.2] (2/4) | 81.8% [48.2-97.7] (9/11) | 19.6% [10.2-32.4] (11/56) |
| Ovary | 25% [0.6-80.6] (1/4) | 0% [0-84.2] (0/2) | 68% [46.5-85.1] (17/25) | 100% [54.1-100] (6/6) | 64.9% [47.5-79.8] (24/37) |
| Multiple Myeloma | 20% [2.5-55.6] (2/10) | 23.1% [5-53.8] (3/13) | 90.9% [58.7-99.8] (10/11) | — | 44.1% [27.2-62.1] (15/34) |
| Esophagus | 16.7% [0.4-64.1] (1/6) | 75% [34.9-96.8] (6/8) | 82.4% [56.6-96.2] (14/17) | 100% [82.4-100] (19/19) | 80% [66.3-90] (40/50) |
| Multiple myeloma | 20% [2.5-55.6] (2/10) | 23.1% [5-53.8] (3/13) | 90.9% [58.7-99.8] (10/11) | — | 44.1% [27.2-62.1] (15/34) |
| Biliary tract | 25% [0.6-80.6] (1/4) | 80% [28.4-99.5] (4/5) | 60% [14.7-94.7] (3/5) | 100% [69.2-100] (10/10) | 75% [53.3-90.2] (18/24) |
| Gastric | 0% [0-70.8] (0/3) | 75% [19.4-99.4] (3/4) | 100% [15.8-100] (2/2) | 100% [63.1-100] (8/8) | 76.5% [50.1-93.2] (13/17) |
| Hepatocellular | 25% [0.6-80.6] (1/4) | 66.7% [9.4-99.2] (2/3) | 100% [47.8-100] (5/5) | 100% [39.8-100] (4/4) | 75% [47.6-92.7] (12/16) |
| Sarcoma | 100% [2.5-100] (1/1) | 0% [0-60.2] (0/4) | 20% [0.5-71.6] (1/5) | 66.7% [22.3-95.7] (4/6) | 37.5% [15.2-64.6] (6/16) |
| Bladder | 60% [14.7-94.7] (3/5) | 66.7% [9.4-99.2] (2/3) | 50% [1.3-98.7] (1/2) | 0% [0-97.5] (0/1) | 54.5% [23.4-83.3] (6/11) |
| Cervical | 12.5% [0.3-52.7] (1/8) | 100% [2.5-100] (1/1) | 100% [15.8-100] (2/2) | — | 36.4% [10.9-69.2] (4/11) |
| Melanoma | 0% [0-70.8] (0/3) | 0% [0-97.5] (0/1) | — | 100% [29.2-100] (3/3) | 42.9% [9.9-81.6] (3/7) |
| Renal Pelvis Urothelial | 100% [2.5-100] (1/1) | 50% [6.8-93.2] (2/4) | — | — | 60% [14.7-94.7] (3/5) |
| Uterine sarcoma | 100% [2.5-100] (1/1) | — | — | — | 100% [2.5-100] (1/1) |
| Myeloid neoplasm | — | — | — | — | 0% [0-60.2] (0/4) |
| Thyroid | 0% [0-84.2] (0/2) | 0% [0-97.5] (0/1) | — | 0% [0-97.5] (0/1) | 0% [0-60.2] (0/4) |

TABLE 28

Classifier performance by cancer type and stage for Assay Panel 3A

| Cancer Type | I | II | III | IV | All Stages |
|---|---|---|---|---|---|
| Lung | 13.3% [5.9-24.6] (8/60) | 73.9% [51.6-89.8] (17/23) | 79.2% [68-87.8] (57/72) | 86.8% [78.8-92.6] (92/106) | 66.7% [60.6-72.4] (174/261) |

TABLE 28-continued

Classifier performance by cancer type and stage for Assay Panel 3A

| Cancer Type | I | II | III | IV | All Stages |
|---|---|---|---|---|---|
| Prostate | 0%<br>[0-9]<br>(0/39) | 1.8%<br>[0.2-6.2]<br>(2/113) | 10.5%<br>[1.3-33.1]<br>(2/19) | 76.5%<br>[50.1-93.2]<br>(13/17) | 9%<br>[5.4-14.1]<br>(17/188) |
| Breast HR positive | 2.3%<br>[0.3-8.1]<br>(2/87) | 18.6%<br>[10.3-29.7]<br>(13/70) | 71.4%<br>[41.9-91.6]<br>(10/14) | 83.3%<br>[35.9-99.6]<br>(5/6) | 16.9%<br>[11.7-23.3]<br>(30/177) |
| Lymphoid neoplasm | 26.7%<br>[7.8-55.1]<br>(4/15) | 81.5%<br>[61.9-93.7]<br>(22/27) | 70.4%<br>[49.8-86.2]<br>(19/27) | 74.4%<br>[57.9-87]<br>(29/39) | 61.9%<br>[53.5-69.8]<br>(91/147) |
| Colorectal | 35.3%<br>[14.2-61.7]<br>(6/17) | 51.9%<br>[31.9-71.3]<br>(14/27) | 78.3%<br>[63.6-89.1]<br>(36/46) | 93.3%<br>[81.7-98.6]<br>(42/45) | 72.6%<br>[64.3-79.9]<br>(98/135) |
| Pancreas | 33.3%<br>[9.9-65.1]<br>(4/12) | 71.4%<br>[41.9-91.6]<br>(10/14) | 75%<br>[47.6-92.7]<br>(12/16) | 92.9%<br>[80.5-98.5]<br>(39/42) | 77.4%<br>[67-85.8]<br>(65/84) |
| Endometrial carcinoma | 15.1%<br>[7.8-25.4]<br>(11/73) | 33.3%<br>[0.8-90.6]<br>(1/3) | 60%<br>[14.7-94.7]<br>(3/5) | 33.3%<br>[0.8-90.6]<br>(1/3) | 19%<br>[11.3-29.1]<br>(16/84) |
| Breast HR negative | 0%<br>[0-21.8]<br>(0/15) | 65%<br>[48.3-79.4]<br>(26/40) | 100%<br>[75.3-100]<br>(13/13) | 100%<br>[15.8-100]<br>(2/2) | 58.6%<br>[46.2-70.2]<br>(41/70) |
| Head and Neck | 85.7%<br>[42.1-99.6]<br>(6/7) | 84.6%<br>[54.6-98.1]<br>(11/13) | 81.2%<br>[54.4-96]<br>(13/16) | 88.5%<br>[69.8-97.6]<br>(23/26) | 85.5%<br>[74.2-93.1]<br>(53/62) |
| Renal | 0%<br>[0-9.5]<br>(0/37) | 25%<br>[0.6-80.6]<br>(1/4) | 50%<br>[6.8-93.2]<br>(2/4) | 72.7%<br>[39-94]<br>(8/11) | 19.6%<br>[10.2-32.4]<br>(11/56) |
| Ovary | 25%<br>[0.6-80.6]<br>(1/4) | 0%<br>[0-84.2]<br>(0/2) | 72%<br>[50.6-87.9]<br>(18/25) | 100%<br>[54.1-100]<br>(6/6) | 67.6%<br>[50.2-82]<br>(25/37) |
| Multiple Myeloma | 40%<br>[12.2-73.8]<br>(4/10) | 46.2%<br>[19.2-74.9]<br>(6/13) | 100%<br>[71.5-100]<br>(11/11) | — | 61.8%<br>[43.6-77.8]<br>(21/34) |
| Esophagus | 16.7%<br>[0.4-64.1]<br>(1/6) | 75%<br>[34.9-96.8]<br>(6/8) | 82.4%<br>[56.6-96.2]<br>(14/17) | 94.7%<br>[74-99.9]<br>(18/19) | 78%<br>[64-88.5]<br>(39/50) |
| Multiple myeloma | 40%<br>[12.2-73.8]<br>(4/10) | 46.2%<br>[19.2-74.9]<br>(6/13) | 100%<br>[71.5-100]<br>(11/11) | — | 61.8%<br>[43.6-77.8]<br>(21/34) |
| Biliary tract | 25%<br>[0.6-80.6]<br>(1/4) | 80%<br>[28.4-99.5]<br>(4/5) | 60%<br>[14.7-94.7]<br>(3/5) | 100%<br>[69.2-100]<br>(10/10) | 75%<br>[53.3-90.2]<br>(18/24) |
| Gastric | 0%<br>[0-70.8]<br>(0/3) | 100%<br>[39.8-100]<br>(4/4) | 100%<br>[15.8-100]<br>(2/2) | 100%<br>[63.1-100]<br>(8/8) | 82.4%<br>[56.6-96.2]<br>(14/17) |
| Hepatocellular | 50%<br>[6.8-93.2]<br>(2/4) | 100%<br>[29.2-100]<br>(3/3) | 100%<br>[47.8-100]<br>(5/5) | 100%<br>[39.8-100]<br>(4/4) | 87.5%<br>[61.7-98.4]<br>(14/16) |
| Sarcoma | 0%<br>[0-97.5]<br>(0/1) | 0%<br>[0-60.2]<br>(0/4) | 20%<br>[0.5-71.6]<br>(1/5) | 50%<br>[11.8-88.2]<br>(3/6) | 25%<br>[7.3-52.4]<br>(4/16) |
| Bladder | 40%<br>[5.3-85.3]<br>(2/5) | 66.7%<br>[9.4-99.2]<br>(2/3) | 50%<br>[1.3-98.7]<br>(1/2) | 0%<br>[0-97.5]<br>(0/1) | 45.5%<br>[16.7-76.6]<br>(5/11) |
| Cervical | 12.5%<br>[0.3-52.7]<br>(1/8) | 100%<br>[2.5-100]<br>(1/1) | 100%<br>[15.8-100]<br>(2/2) | — | 36.4%<br>[10.9-69.2]<br>(4/11) |
| Melanoma | 0%<br>[0-70.8]<br>(0/3) | 0%<br>[0-97.5]<br>(0/1) | — | 100%<br>[29.2-100]<br>(3/3) | 42.9%<br>[9.9-81.6]<br>(3/7) |
| Renal Pelvis Urothelial | 100%<br>[2.5-100]<br>(1/1) | 25%<br>[0.6-80.6]<br>(1/4) | — | — | 40%<br>[5.3-85.3]<br>(2/5) |
| Uterine sarcoma | 100%<br>[2.5-100]<br>(1/1) | — | — | — | 100%<br>[2.5-100]<br>(1/1) |
| Myeloid neoplasm | — | — | — | — | 0%<br>[0-60.2]<br>(0/4) |
| Thyroid | 0%<br>[0-84.2]<br>(0/2) | 0%<br>[0-97.5]<br>(0/1) | — | 0%<br>[0-97.5]<br>(0/1) | 0%<br>[0-60.2]<br>(0/4) |

TABLE 29

Classifier performance by cancer type and stage for Assay Panel 5

| Cancer Type | I | II | III | IV | All Stages |
|---|---|---|---|---|---|
| Lung | 20% | 78.3% | 86.1% | 91.5% | 72.4% |
|  | [10.8-32.3] | [56.3-92.5] | [75.9-93.1] | [84.5-96] | [66.6-77.7] |
|  | (12/60) | (18/23) | (62/72) | (97/106) | (189/261) |
| Prostate | 2.6% | 4.4% | 10.5% | 76.5% | 11.2% |
|  | [0.1-13.5] | [1.5-10] | [1.3-33.1] | [50.1-93.2] | [7-16.6] |
|  | (1/39) | (5/113) | (2/19) | (13/17) | (21/188) |
| Breast HR positive | 4.6% | 25.7% | 71.4% | 100% | 21.5% |
|  | [1.3-11.4] | [16-37.6] | [41.9-91.6] | [54.1-100] | [15.7-28.3] |
|  | (4/87) | (18/70) | (10/14) | (6/6) | (38/177) |
| Lymphoid neoplasm | 26.7% | 74.1% | 77.8% | 79.5% | 62.6% |
|  | [7.8-55.1] | [53.7-88.9] | [57.7-91.4] | [63.5-90.7] | [54.2-70.4] |
|  | (4/15) | (20/27) | (21/27) | (31/39) | (92/147) |
| Colorectal | 47.1% | 70.4% | 82.6% | 93.3% | 79.3% |
|  | [23-72.2] | [49.8-86.2] | [68.6-92.2] | [81.7-98.6] | [71.4-85.8] |
|  | (8/17) | (19/27) | (38/46) | (42/45) | (107/135) |
| Pancreas | 58.3% | 71.4% | 87.5% | 95.2% | 84.5% |
|  | [27.7-84.8] | [41.9-91.6] | [61.7-98.4] | [83.8-99.4] | [75-91.5] |
|  | (7/12) | (10/14) | (14/16) | (40/42) | (71/84) |
| Endometrial carcinoma | 20.5% | 33.3% | 60% | 66.7% | 25% |
|  | [12-31.6] | [0.8-90.6] | [14.7-94.7] | [9.4-99.2] | [16.2-35.6] |
|  | (15/73) | (1/3) | (3/5) | (2/3) | (21/84) |
| Breast HR negative | 6.7% | 72.5% | 100% | 100% | 64.3% |
|  | [0.2-31.9] | [56.1-85.4] | [75.3-100] | [15.8-100] | [51.9-75.4] |
|  | (1/15) | (29/40) | (13/13) | (2/2) | (45/70) |
| Head and Neck | 100% | 84.6% | 87.5% | 88.5% | 88.7% |
|  | [59-100] | [54.6-98.1] | [61.7-98.4] | [69.8-97.6] | [78.1-95.3] |
|  | (7/7) | (11/13) | (14/16) | (23/26) | (55/62) |
| Renal | 0% | 50% | 50% | 81.8% | 23.2% |
|  | [0-9.5] | [6.8-93.2] | [6.8-93.2] | [48.2-97.7] | [13-36.4] |
|  | (0/37) | (2/4) | (2/4) | (9/11) | (13/56) |
| Ovary | 25% | 0% | 88% | 100% | 78.4% |
|  | [0.6-80.6] | [0-84.2] | [68.8-97.5] | [54.1-100] | [61.8-90.2] |
|  | (1/4) | (0/2) | (22/25) | (6/6) | (29/37) |
| Multiple Myeloma | 40% | 46.2% | 100% | — | 61.8% |
|  | [12.2-73.8] | [19.2-74.9] | [71.5-100] |  | [43.6-77.8] |
|  | (4/10) | (6/13) | (11/11) |  | (21/34) |
| Esophagus | 25% | 80% | 60% | 100% | 75% |
|  | [0.6-80.6] | [28.4-99.5] | [14.7-94.7] | [69.2-100] | [53.3-90.2] |
|  | (1/4) | (4/5) | (3/5) | (10/10) | (18/24) |
| Multiple myeloma | 0% | 100% | 100% | 100% | 82.4% |
|  | [0-70.8] | [39.8-100] | [15.8-100] | [63.1-100] | [56.6-96.2] |
|  | (0/3) | (4/4) | (2/2) | (8/8) | (14/17) |
| Biliary tract | 50% | 100% | 100% | 100% | 87.5% |
|  | [6.8-93.2] | [29.2-100] | [47.8-100] | [39.8-100] | [61.7-98.4] |
|  | (2/4) | (3/3) | (5/5) | (4/4) | (14/16) |
| Gastric | 0% | 0% | 20% | 50% | 25% |
|  | [0-97.5] | [0-60.2] | [0.5-71.6] | [11.8-88.2] | [7.3-52.4] |
|  | (0/1) | (0/4) | (1/5) | (3/6) | (4/16) |
| Hepatocellular | 40% | 66.7% | 50% | 0% | 45.5% |
|  | [5.3-85.3] | [9.4-99.2] | [1.3-98.7] | [0-97.5] | [16.7-76.6] |
|  | (2/5) | (2/3) | (1/2) | (0/1) | (5/11) |
| Sarcoma | 12.5% | 100% | 100% | — | 36.4% |
|  | [0.3-52.7] | [2.5-100] | [15.8-100] |  | [10.9-69.2] |
|  | (1/8) | (1/1) | (2/2) |  | (4/11) |
| Bladder | 0% | 0% | — | 100% | 42.9% |
|  | [0-70.8] | [0-97.5] |  | [29.2-100] | [9.9-81.6] |
|  | (0/3) | (0/1) |  | (3/3) | (3/7) |
| Cervical | 100% | 25% | — | — | 40% |
|  | [2.5-100] | [0.6-80.6] |  |  | [5.3-85.3] |
|  | (1/1) | (1/4) |  |  | (2/5) |
| Melanoma | 100% | — | — | — | 100% |
|  | [2.5-100] |  |  |  | [2.5-100] |
|  | (1/1) |  |  |  | (1/1) |
| Renal Pelvis Urothelial | — | — | — | — | 0% |
|  |  |  |  |  | [0-60.2] |
|  |  |  |  |  | (0/4) |
| Uterine sarcoma | 0% | 0% | — | 0% | 0% |
|  | [0-84.2] | [0-97.5] |  | [0-97.5] | [0-60.2] |
|  | (0/2) | (0/1) |  | (0/1) | (0/4) |
| Myeloid neoplasm | 40% | 46.2% | 100% | — | 61.8% |
|  | [12.2-73.8 ] | [19.2-74.9] | [71.5-100] |  | [43.6-77.8] |
|  | (4/10) | (6/13) | (11/11) |  | (21/34) |
| Thyroid | 25% | 80% | 60% | 100% | 75% |
|  | [0.6-80.6] | [28.4-99.5] | [14.7-94.7] | [69.2-100] | [53.3-90.2] |
|  | (1/4) | (4/5) | (3/5) | (10/10) | (18/24) |

7. INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

8. EQUIVALENTS

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. The described operations and their associated modules may be embodied in software, firmware, hardware, or any combinations thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment, thereby providing a framework for various possibilities of described embodiments to function together.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

While various specific embodiments have been illustrated and described, the above specification is not restrictive. It will be appreciated that various changes can be made without departing from the spirit and scope of the description(s). Many variations will become apparent to those skilled in the art upon review of this specification.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11410750B2). An electronic copy of the "Sequence Listing" will also be available from the USPTO upon request and payment of the fee set forth in 37 CFR 1.19(b)(3).

What is claimed is:

1. A method of processing cell-free DNA fragments comprising:
   a) reacting cell-free DNA fragments from a biological sample with a deaminating agent to generate converted cell-free DNA fragments;
   b) contacting the converted cell-free DNA fragments or amplification products thereof with a panel of different oligonucleotide probes configured to hybridize to converted cell-free DNA fragments derived from at least 500 target genomic regions;
   c) enriching a subset of the converted cell-free DNA fragments or amplification products thereof, wherein the enriching comprises (i) separating probe-bound DNA from unbound DNA, and (ii) amplifying the separated probe-bound DNA using a plurality of primers; and
   d) sequencing the enriched subset to obtain a set of sequence reads;
   wherein each target genomic region of the at least 500 target genomic regions has an anomalous methylation pattern in cancerous samples, and
   wherein each of the at least 500 target genomic regions comprises a sequence with complementarity to at least a pair of probes in the panel, wherein each probe of a pair has a first portion and a second portion, wherein the first portions of a probe pair are complementary to the same sequence of at least 25 nucleotides in length, and wherein the second portions of a probe pair are complementary to different sequences at different ends of the sequence complementary to the respective first portions.

2. The method of claim 1, wherein each of the at least 500 target genomic regions is determined to be anomalously methylated in cancer training samples based on criteria comprising a number of cancer samples that comprise an anomalously methylated cfDNA fragment that overlaps the target genomic region, and wherein the target genomic region is determined to be anomalously methylated in cancer training samples relative to non-cancer training samples based on criteria comprising $N_{cancer}$ and $N_{non-cancer}$, wherein:

$N_{cancer}$, for each CpG, site is a number of cancer samples that include a cfDNA fragment covering the CpG site in the cfDNA fragment that (1) has at least 4 CpG sites, wherein at least 70% of the CpG sites are methylated or unmethylated and (2) has a p-value rarity in non-cancerous samples of below a threshold value; and $N_{non-cancer}$, for each CpG, site is a number of non-cancer samples that include a cfDNA fragment covering the CpG site in the cfDNA fragment that (1) has at least 4 CpG sites, wherein at least 70% of the sites are methylated or unmethylated and (2) has a p-value rarity in non-cancerous samples of below a threshold value.

3. The method of claim 2, wherein each of the at least 500 target genomic regions is determined to be anomalously methylated based on criteria positively correlated with $N_{cancer}$ and negatively correlated with $N_{non-cancer}$.

4. The method of claim 2, wherein each of the at least 500 target genomic regions is determined to be anomalously methylated based on a score, wherein the score is calculated as $(N_{cancer}+1)/(N_{cancer}+N_{non-cancer}+2)$.

5. The method of claim 1, wherein the at least 500 target genomic regions comprise all genomic regions identified in List 1.

6. The method of claim 1, wherein the at least 500 target genomic regions comprise at least 500 of genomic regions identified in List 1.

7. The method of claim 1, wherein the at least 500 target genomic regions comprise at least 500 of genomic regions identified in List 2.

8. The method of claim 1, wherein the at least 500 target genomic regions comprise at least 500 of genomic regions identified in List 3.

9. The method of claim 1, wherein the at least 500 target genomic regions comprise at least 500 of genomic regions identified in List 5.

10. The method of claim 1, wherein the at least 500 target genomic regions comprise at least 500 of genomic regions identified in List 8.

11. The method of claim 1, wherein the at least 500 target genomic regions comprise at least 500 genomic regions identified in List 4.

12. The method of claim 1, wherein the at least 500 target genomic regions comprise at least 500 genomic regions identified in List 6.

13. The method of claim 1, further comprising:
e) generating a set of test features from the set of sequence reads; and
f) applying the set of test features to a classifier configured to determine:
a presence or absence of cancer;
a stage of cancer; or
a type of cancer.

14. The method of claim 13, wherein the classifier comprises a model that is trained by a training process with a cancer set of training fragments from one or more training subjects with a cancer and a non-cancer set of training fragments from one or more training subjects without cancer, wherein both the cancer set of training fragments and the non-cancer set of training fragments comprise a plurality of training fragments.

15. The method of claim 14, wherein the one or more training subjects with a cancer comprise training subjects collectively having at least 5 cancer types selected from the group consisting of lung cancer, breast cancer, prostate cancer, lymphoid neoplasm, colorectal cancer, pancreas & gallbladder cancer, uterine cancer, upper gastrointestinal tract cancer, head & neck cancer, renal cancer, ovarian cancer, multiple myeloma, liver & bile duct cancer, sarcoma, bladder & urothelial cancer, anorectal cancer, cervical cancer, and melanoma, myeloid neoplasm and thyroid cancer.

16. The method of claim 14, wherein the training process comprises:
obtaining sequence information of training fragments from a plurality of training subjects;
for each training fragment, determining whether that training fragment is hypomethylated or hypermethylated, wherein each of the hypomethylated and the hypermethylated training fragments comprises at least five CpG sites with at least 80% of the CpG sites being unmethylated or methylated, respectively,
for each training subject, generating a training feature vector for each hypomethylated training fragment and each hypermethylated training fragment, and
training the model with the training feature vectors from the one or more training subjects without cancer and the training feature vectors from the one or more training subjects with a cancer.

17. The method of claim 14, wherein the model comprises a kernel logistic regression classifier, a random forest classifier, a mixture model, a convolutional neural network, or an autoencoder model.

18. The method of claim 13, wherein the classifier has an area under a receiver operating characteristic curve for detecting the presence or absence of cancer of greater than 0.75.

19. The method of claim 13, wherein at a specificity of 0.99, the classifier has a sensitivity for detecting the presence or absence of cancer of at least 40%.

20. The method of claim 13, wherein at a specificity of 0.994, the classifier has a sensitivity for one or more cancers selected from the group consisting of:
lung cancer, wherein the sensitivity for detecting lung cancer is at least 60%;
colorectal cancer, wherein the sensitivity for detecting colorectal cancer is at least 70%;
pancreatic or gallbladder cancer, wherein the sensitivity for detecting pancreatic or gallbladder cancer is at least 70%;
head and neck cancer, wherein the sensitivity for detecting head and neck cancer is at least 80%;
ovarian cancer, wherein the sensitivity for detecting lung ovarian cancer is at least 60%;
multiple myeloma, wherein the sensitivity for detecting multiple myeloma is at least 60%;
upper GI tract cancer, wherein the sensitivity for detecting upper GI tract cancer is at least 75%;

liver or bile duct cancer, wherein the sensitivity for detecting liver or bile duct cancer is at least 70%; and
lymphoid neoplasm, wherein the sensitivity for detecting lymphoid neoplasm is at least 60%.

21. The method of claim 13, wherein a presence of cancer is detected at a specificity of at least 0.99, and an accuracy of assigning a cancer type among at least 10 cancer types is at least 85%.

22. The method of claim 21, wherein the at least 10 cancer types are selected from lung cancer, colorectal cancer, lymphoid neoplasm, breast cancer, pancreas & gallbladder cancer, head & neck cancer, upper gastrointestinal tract cancer, ovarian cancer, liver & bile duct cancer, uterine cancer, prostate cancer, multiple myeloma, renal cancer, anorectal cancer, bladder & urothelial cancer, sarcoma, cervical cancer, and melanoma.

23. The method of claim 13, wherein a presence of cancer is detected at a specificity of 0.99, and an accuracy of assigning a cancer type for at least 10 cancer types, wherein the at least 10 cancer types are selected from the group consisting of:
  a cancer type of lung cancer, wherein the accuracy of assigning a cancer type of lung cancer is at least 90%;
  a cancer type of colorectal cancer, wherein the accuracy of assigning a cancer type of colorectal cancer is at least 90%;
  lymphoid neoplasm, wherein the accuracy of assigning a cancer type of lymphoid neoplasm is at least 90%;
  breast cancer, wherein the accuracy of assigning a cancer type of breast cancer is at least 90%;
  pancreas & gallbladder cancer, wherein the accuracy of assigning a cancer type of pancreas & gallbladder cancer is at least 85%
  head & neck cancer, wherein the accuracy of assigning a cancer type of head & neck cancer is at least 80%;
  upper gastrointestinal tract cancer, wherein the accuracy of assigning a cancer type of upper gastrointestinal tract cancer is at least 80%;
  ovarian cancer, wherein the accuracy of assigning a cancer type of ovarian cancer is at least 85%;
  liver & bile duct cancer, wherein the accuracy of assigning a cancer type of liver & bile duct cancer is at least 70%
  uterine cancer, wherein the accuracy of assigning a cancer type of uterine cancer is at least 90%;
  prostate cancer, wherein the accuracy of assigning a cancer type of prostate cancer is at least 85%;
  multiple myeloma, wherein the accuracy of assigning a cancer type of multiple myeloma is at least 90%; and
  renal cancer, wherein the accuracy of assigning a cancer type of renal cancer is at least 90%.

24. The method of claim 1, wherein for each probe of the pairs of probes, the first portion is at least 30 nucleotides in length, and the second portion is at least 15 nucleotides in length.

25. The method of claim 1, wherein for each probe of the pairs of probes, the second portion is at least 50 nucleotides in length.

26. The method of claim 24, wherein for each probe of the pairs of probes, the first portion and second portion together are at least 65 nucleotides in length.

27. The method of claim 24, wherein each probe of the pairs of probes is less than 300 nucleotides in length.

28. The method of claim 1, wherein the target genomic regions are human genomic regions, and further wherein at least one probe for each of the at least 500 target genomic regions (a) comprises a length of at least 45 bases, and (b) does not comprise a contiguous 45 bases with at least 90% sequence complementarity to 20 off-target regions in a GRCh37/hg19 genome.

* * * * *